US012150741B2

(12) United States Patent
Gopalakrishnan

(10) Patent No.: US 12,150,741 B2
(45) Date of Patent: Nov. 26, 2024

(54) FULLY NON-INVASIVE BLOOD SUGAR LEVEL MONITORING APPARATUS INTEGRATED WITH REAL-TIME HEALTH SUPPORT SYSTEM

(71) Applicant: Muralidharan Gopalakrishnan, Thane (IN)

(72) Inventor: Muralidharan Gopalakrishnan, Thane (IN)

(73) Assignee: Muralidharan Gopalakrishnan, Maharashtra (IN)

(*) Notice: Subject to any disclaimer, the term of this patent is extended or adjusted under 35 U.S.C. 154(b) by 1162 days.

(21) Appl. No.: 16/961,793

(22) PCT Filed: Jan. 13, 2019

(86) PCT No.: PCT/IB2019/050252
§ 371 (c)(1),
(2) Date: Jul. 13, 2020

(87) PCT Pub. No.: WO2019/138381
PCT Pub. Date: Jul. 18, 2019

(65) Prior Publication Data
US 2021/0074421 A1    Mar. 11, 2021

Related U.S. Application Data

(60) Provisional application No. 62/617,273, filed on Jan. 14, 2018.

(51) Int. Cl.
*A61B 5/0205*    (2006.01)
*A61B 5/00*      (2006.01)
(Continued)

(52) U.S. Cl.
CPC ........ *A61B 5/02055* (2013.01); *A61B 5/0002* (2013.01); *A61B 5/0022* (2013.01);
(Continued)

(58) Field of Classification Search
CPC ..... A61B 5/02055; A61B 5/24; A61B 5/0002; A61B 5/0022; A61B 5/0205; A61B 5/053;
(Continued)

(56) References Cited

U.S. PATENT DOCUMENTS

2017/0181678 A1* 6/2017 Newberry ............. A61B 5/743
2017/0292908 A1* 10/2017 Wilk .................... G01N 21/359
2017/0296178 A1* 10/2017 Miller .................. A61B 5/4869

* cited by examiner

*Primary Examiner* — Carl H Layno
*Assistant Examiner* — Aya Ziad Bakkar

(57) ABSTRACT

A non-invasive continuous blood sugar level monitoring apparatus integrated with a real-time health support system. The blood sugar levels and other vital physiological information of the user can also be tracked wirelessly through the apparatus. The apparatus has an integrated real-time alert and reminder feature for notifying the user during medication and unusual physiological conditions. An automated diet and lifestyle recommendation solution is integrated into the device to help the user maintain healthy blood sugar and blood pressure levels. The low-powered the telemetry device is used for communicating the stored physiological information of the user and the computed results between the network of devices.

24 Claims, 47 Drawing Sheets

(51) Int. Cl.
| | |
|---|---|
| A61B 5/053 | (2021.01) |
| A61B 5/11 | (2006.01) |
| A61B 5/145 | (2006.01) |
| A61B 5/1455 | (2006.01) |
| A61B 5/16 | (2006.01) |
| A61J 7/04 | (2006.01) |
| G01J 3/02 | (2006.01) |
| G01J 3/10 | (2006.01) |
| G01J 3/28 | (2006.01) |
| G01J 3/45 | (2006.01) |
| G01P 15/18 | (2013.01) |
| G05B 19/042 | (2006.01) |
| G06Q 50/00 | (2012.01) |
| G16H 10/65 | (2018.01) |
| G16H 20/10 | (2018.01) |
| G16H 20/60 | (2018.01) |
| G16H 20/70 | (2018.01) |
| G16H 40/20 | (2018.01) |
| G16H 40/40 | (2018.01) |
| G16H 40/67 | (2018.01) |
| G16H 50/20 | (2018.01) |
| G16H 50/30 | (2018.01) |
| G16H 50/50 | (2018.01) |
| G16H 50/70 | (2018.01) |
| G16H 70/20 | (2018.01) |
| A61B 5/01 | (2006.01) |
| A61B 5/021 | (2006.01) |
| A61B 5/024 | (2006.01) |
| G06F 3/01 | (2006.01) |
| G06F 3/0488 | (2022.01) |
| H02J 7/00 | (2006.01) |
| H02J 7/02 | (2016.01) |
| H02J 7/34 | (2006.01) |
| H02J 50/10 | (2016.01) |

(52) U.S. Cl.
CPC ............ *A61B 5/0205* (2013.01); *A61B 5/053* (2013.01); *A61B 5/1112* (2013.01); *A61B 5/14532* (2013.01); *A61B 5/14551* (2013.01); *A61B 5/14552* (2013.01); *A61B 5/165* (2013.01); *A61B 5/4809* (2013.01); *A61B 5/486* (2013.01); *A61B 5/4872* (2013.01); *A61B 5/6803* (2013.01); *A61B 5/681* (2013.01); *A61B 5/6816* (2013.01); *A61B 5/6826* (2013.01); *A61B 5/6831* (2013.01); *A61B 5/721* (2013.01); *A61B 5/7214* (2013.01); *A61B 5/7217* (2013.01); *A61B 5/7246* (2013.01); *A61B 5/7257* (2013.01); *A61B 5/7267* (2013.01); *A61B 5/742* (2013.01); *A61B 5/746* (2013.01); *A61B 5/747* (2013.01); *A61B 5/7475* (2013.01); *A61B 5/748* (2013.01); *A61J 7/04* (2013.01); *G01J 3/0286* (2013.01); *G01J 3/108* (2013.01); *G01J 3/2803* (2013.01); *G01J 3/45* (2013.01); *G01P 15/18* (2013.01); *G05B 19/042* (2013.01); *G06Q 50/01* (2013.01); *G16H 10/65* (2018.01); *G16H 20/10* (2018.01); *G16H 20/60* (2018.01); *G16H 20/70* (2018.01); *G16H 40/20* (2018.01); *G16H 40/40* (2018.01); *G16H 40/67* (2018.01); *G16H 50/20* (2018.01); *G16H 50/30* (2018.01); *G16H 50/50* (2018.01); *G16H 50/70* (2018.01); *G16H 70/20* (2018.01); *A61B 5/01* (2013.01); *A61B 5/021* (2013.01); *A61B 5/02141* (2013.01); *A61B 5/024* (2013.01); *A61B 5/02427* (2013.01); *A61B 5/02433* (2013.01); *A61B 2560/0214* (2013.01); *A61B 2560/0223* (2013.01); *A61B 2560/0238* (2013.01); *A61B 2560/0252* (2013.01); *A61B 2562/0219* (2013.01); *A61B 2562/0242* (2013.01); *A61B 2562/028* (2013.01); *A61B 2562/0285* (2013.01); *G05B 2219/2639* (2013.01); *G06F 3/017* (2013.01); *G06F 3/0488* (2013.01); *H02J 7/0045* (2013.01); *H02J 7/02* (2013.01); *H02J 7/345* (2013.01); *H02J 50/10* (2016.02)

(58) Field of Classification Search
CPC .............. A61B 5/1112; A61B 5/14532; A61B 5/14551; A61B 5/14552; A61B 5/486; A61B 5/4872; A61B 5/6826; A61B 5/721; A61B 5/7214; A61B 5/7217; A61B 5/7246; A61B 5/7257; A61B 5/746; A61B 5/747; A61B 5/7475; A61B 5/748; A61B 5/01; A61B 5/021; A61B 5/02427; A61B 5/02433; A61B 2560/0214; A61B 2560/0223; A61B 2560/0238; A61B 2560/0252; A61B 2562/0219; A61B 2562/0242; G16H 40/67; G16H 40/20; G16H 50/50; G16H 50/30; G16H 50/70; G16H 50/20; G16H 20/10; G16H 40/40; A61J 7/04; G01J 3/0286; G01J 3/108; G01J 3/2803; G01J 3/45; G05B 19/042; G05B 2219/2639; G06Q 50/01; H02J 50/10; H02J 7/0045; H02J 7/02; H02J 7/345; G06F 3/017; G06F 3/0488
See application file for complete search history.

FULLY NON-INVASIVE BLOOD SUGAR LEVEL MONITORING APPARATUS INTEGRATED WITH REAL-TIME HEALTH SUPPORT SYSTEM

TECHNICAL FIELD

The present invention relates to an intelligent telemetry instrumentation for non-invasively monitoring continuous blood sugar levels, blood pressure data, psychological stress and other physiological parameters. It is, in particular, related to clinical monitors, health management gadgets and wearable medical devices involving transmittive optical sensing design.

BACKGROUND OF THE INVENTION

Modern lifestyle and food habits have huge impact on our physiological and psychological health. In this fast-paced society, it has become a necessity to track and manage our health and activities. In fact, globally 1 in 11 of us are suffering from diabetic condition and 21% of the people in US are standing on the diabetic border. In the coming quarter century, this count is expected to raise by more than 200 million and the prevalence is expected to raise by over 25%. The current technology either offers painful periodic invasive monitoring solution or disposable microneedles based monitoring solution. The current continuous glucose tracking devices also fails to monitor blood sugar levels in prediabetic range and does not act as a management or prevention solution. Attempts have been made in the past by inventors and academic scholars to create a non-invasive technology, but their hardware and processing architecture proposals ignores underlying scientific principles of transmittive sensing and real-time processing techniques.

Hence, the invention is directed towards a transmittive apparatus design and real-time processing system that can intelligently overcome the barriers utilizing boundary angle conditions and other signal altering factors like dispersion effects. The disclosure describes an advanced portable continuous blood sugar monitoring solution for tracking blood glucose of both prediabetic and diabetic spectrum, which also has a real-time diet recommendation and lifestyle management system as an integrated prevention solution. The device also includes other health guidance components like blood pressure fluctuation tracking and hypertension management system, and emergency life-support system, etc.

What is needed is:
1. Transmittive sensing based accurate continuous blood sugar monitoring apparatus that can work for every segment of the population;
2. An intelligent blood sugar management solution that can act as an effective medical and well-being guidance system; and
3. An integrated general wellness solution for managing other physiological conditions such as hypertension and emotional stress.

SUMMARY OF THE INVENTION

The object of the invention is to present a totally non-invasive continuous blood glucose monitoring solution integrated with intelligent medical condition management and automated recommendation system. The apparatus can also be utilized to monitor and manage blood pressure and other health parameters.

First Aspect

In the first aspect, a transmittive configuration based near-infrared optical spectrometer is presented. The near-infrared (Near-IR) spectrometer comprises of a set Near-IR light sources arranged in transmittive configuration with a quantum distance of wavelength number ($k\lambda$) between them. An optical lens is placed after the near-infrared at signal probe end, which focuses and constructively interferes near-infrared radiation on the sensing spot. The transmitted optical response is captured and focused by the photodetector-end optical lens on the near-infrared photodetector. The transmitted response is recorded by the near-infrared photodetector. During stationary real-time sensing set-up, the spectrometer may be alternatively arranged in inverted configuration to reduce background noise.

Second Aspect

The second aspect of the invention presents a green optical spectrometer. The green optical spectrometer comprises of two green LED signal probes, of which one LED signal probe is placed at normal direction and the other LED is tilted at a critical angle ($\theta c$). Each LED signal probe has an optical lens placed after them, which focuses and transmits the green signal on the sensing spot in their corresponding direction. An optical lens and green photodetector set are placed in reflective configuration next to the tilted green LED to measure the response reflected by the coarse skin surface. An optical lens and green photodetector set is placed in the transmittive configuration with respect to the normal green LED signal probe to record the transmitted response. During stationary real-time sensing set-up, the spectrometer may be alternatively arranged in inverted configuration to minimize background noise.

Third Aspect

Red light based transmittive dispersion analyser is provided in the third aspect of the invention. The dispersion analyser comprises of a signal probe set of normal red LED and two adjacent red LEDs tilted at an angle and focused on the central photodetector system. The adjacent red LED signal probes are tilted in opposite direction and placed on the either side of the normal LED. A set of optical lenses are placed before the LED signal probes to concentrate and focus the light on the sensing spot. The dispersion analyser further comprises of a set of red photodetectors and corresponding optical lens placed at different response receiving positions. The signal difference between the response of central photodetector and response of other photodetectors are taken to analyse the dispersion effect. During stationary real-time sensing set-up, the spectrometer may be alternatively arranged in inverted configuration to cut-down the background noise.

Fourth Aspect

In the fourth aspect, infrared (IR) radiation dispersion analyser is provided. The dispersion analyser comprises of a signal probe set of normal IR LED and two adjacent IR LEDs tilted at an angle and focused on the central photodetector system. The adjacent IR LED signal probes are tilted in opposite direction and placed on the either side of the normal LED. A set of optical lenses are placed before the LED signal probes to concentrate and focus the light on the sensing spot. The dispersion analyser further comprises of a set of IR photodetectors and optical lens placed at different response receiving positions. The signal difference between the response of central photodetector and response of other photodetectors are taken to analyse the dispersion effect. During stationary real-time sensing set-up, the spectrometer may be alternatively arranged in inverted configuration to curtail background noise.

Fifth Aspect

The fifth aspect of the invention puts forth a low-powered hardware to implement the optical spectrometers.

The hardware comprises of optical signal probes of Near-IR light sources, IR LEDs, Red LEDs and Green LEDs, and photodetector probes of Near-IR photodetector, IR photodetectors, Red photodetectors and Green photodetectors with their respective optical elements. The LED signal probes, photodetector probes and their respective optical elements are arranged according to the spectrometer configurations. The input to the Near-IR LED signal probes are coherently driven through a tuneable BJT/FET based active current amplifier circuit and the set of resistors. A set of three micro-switches are used to alternatively drive the input to the red LEDs and infrared LEDs. The set of three switches are utilized before the red LED and IR LED circuit line to reduce the tracing efforts and component use. A set of resistors are used in the red LED and IR LED circuit line to distribute the input signal. A main micro-switch set is used as a low powered means to shift the input from the LED frontend to the green LEDs, red LED and IR LED circuit line and to the active current amplifier attached to the Near-IR LDs. The LED frontend comprises of LED driver, LED controller, PWM and clock controller, which tunes and sends the input signal through the main micro-switch set.

A BJT/FET based Darlington pair and small signal current source is attached to the Near-IR photodetector, which is used to amplify the low powered Near-IR response. The low power green response signals pass through the optical elements and the green photodetector probes, which are amplified by the Darlington pair and small current source attached to the respective photodetector. The small current sources attached to the photodetectors adds baseline to the response signals. The red response and IR response, recorded by the red photodetector-optical lens system and IR photodetector-optical lens system, are extracted alternatively by using a switch set. The central red-IR photodetector response is separately processed using a stabilizing buffer and circuit line of ADC, Ambient Noise cancellation IC and DAC. The responses of non-central photodetector are summed using an op-amp. The summed non-central signal response passes through the stabilizing buffer unit and circuit line of ADC, Ambient Noise cancellation IC and DAC. The red-IR response signals are extracted through two different circuit lines. One response line is utilized to analyse the total IR-red response and the other circuit line is utilized to extract the dispersion signal. An Instrumental Amplifier is attached to the response lines of summed non-central photodetector output and central photodetector output for extracting the dispersion information. The power line noise in the analysed dispersion signal is filtered through a power notch. The filtered dispersion signal is sent to the microprocessor through an ADC. The central photodetector signal and summed non-central photodetector signal are furthered aggregated using resistors and Transimpedance (TIA) amplifier of the photodetector frontend. The response signals of near-IR light, tilted green light, transmitted green light and red-IR light are processed and filtered using the photodetector frontend circuit elements of TIA amplifier, power notch, ADC and Noise cancellation IC. The processed output response of the individual spectrum is then sent to the microprocessor. A main micro-switch set is attached between the photodetector frontend and response line of different light spectrum, which shifts the output response to respective photodetector circuit based on the input signals. The photodetector-end switch set reduces the overall component use and power consumption. An additional switch set can be utilized to reduce the count of the power notch and Noise cancellation IC.

A non-contact MEMs/NEMs temperature biosensor, attached to the microprocessor, logs the body temperature response and thermal feedback. An ambient temperature sensor, attached to the microprocessor, records the environment temperature and temperature of the internal electronics system. The 9/6 axis MEMs/NEMs accelerometer of the hardware is utilized as a real-time feedback to remove motion noise from the bio-signal response. A set of wireless antennae of WLAN, BLE, GSM and GPS are either externally attached to the microprocessor or integrated inside the microprocessor. The set of wireless antennae communicates the data between the telemetry apparatus, and the set of external storage and computational devices like accessorial mobile devices, server, etc. The set of wireless antennae along with the accelerometer is used for tracking the real-time location and movement signals like phase, speed, steps taken, etc. The microprocessor is used for communicating commands and feedbacks with the internal electronic components of LED frontend, photodetector frontend, accelerometer, temperature biosensors, ambient temperature sensors, other sensors, wireless antennas, USB module, buttons, potentiometer integrated navigator, fancy LED, touch display and other electronics modules. The function of microprocessors also includes computing and storing the required information. A mini-touch display is attached to the hardware for viewing and accessing the real-time medical information, health data and on-device applications. The touch display is also used to calibrate and operate the instrumentation. The fancy LED flashes for displaying different device modes, device status and decorative applications. The buttons and potentiometer integrated navigator are used for operating and calibrating the device. The memory module attached to the microprocessor is utilized for internally storing the information.

Apart from the display unit, the hardware of the telemetry device is internally or externally attached to an additional user interaction system of consisting of mic and speaker. The set of user interaction hardware components is utilized by the user for interacting with the medical and health practitioners for clinical and health analysis. The professionals can send and receive the information, as well supervise the user through the user interaction system. The user interaction unit is also used as the means to perceive the recorded and computed information, and to operate the device and its in-built applications.

The hardware of the telemetry apparatus is attached to a power supply unit, which comprises of power management IC, supercapacitor-battery set, supercapacitor-renewable energy harvester set, wireless coil, USB module and negative voltage converter. The power management IC of the power supply unit, attached to the hardware and microprocessor, regulates the current flow and power supply. The negative voltage converter attached to the power management unit generates the negative reference signal. The USB module and supercapacitor-battery are utilized for powering the electronic circuit. The USB module is also used for communicating the data with the external devices and charging the battery of the internal circuit. The device is wirelessly recharged through the coil. The power supply unit includes an alternative and supplementary power supply unit containing renewable energy harvester and supercapacitor.

Sixth Aspect

The sixth aspect of the invention provides the method for device initialization and apparatus calibration. During the initial device start-up, the age, weight, gene info, BMI, Fat % and contact layer picture of the user is recorded. The recorded contact layer skin colour is processed on a scale of 1 to 10 and the contact picture is again recorded multiple times. The median values of the processed contact layer color are stored and utilized. On unavailability of the contact layer recording, the realistic profile picture of the user is processed, and the values are altered by an adjusting parameter to extract the realistic value of the contact layer skin color. Different blood sugar values, blood pressure values and other health parameters are recorded and processed for calibrating the device. The blood sugar values, blood pressure values and other vital health parameters are recorded during sitting position, standing position, relaxing position, fasting glucose, post-dinner, post-breakfast, post-lunch, post-morning sleep, post-exercise, before dinner, before breakfast, before lunch, before bed-time and also during the hypoglycaemic and hyperglycaemic conditions. If increasing value of hyperglycaemic and hypoglycaemic conditions are recognized, the device is re-calibrated. For diagnosed hyperglycaemic and hypoglycaemic conditions, the apparatus records and stores the blood sugar values, blood pressure values and vital information multiple times a day. If enough calibration values are available, the calibration process is skipped and if lesser number are values are available, then more calibration values are recorded. The Near-IR light sources, green LEDs, IR LEDs and red LEDs are initiated, and the values of the responses are recorded in their respective matrices. The recorded responses are normalized according to the light source area and power. The transmittive green response (GN) and reflective green response (GT) signals are analyzed for DC losses. The recorded red and IR response signals are analyzed to extract the Integrated signal response (Rtot-IRtot), Differential/Dispersion signal responses (Rdiff-IRdiff) and power response (RP-IRP). The body temperature (Btemp) and Ambient temperature response (Atemp) are recorded and the response signals are adjusted as per the temperature stats. Accelerometer is initiated to record movement data and to remove motion noise in the real-time signal. Wireless antennae are initiated and analysed for location and movement data.

Seventh Aspect

The seventh aspect of the invention provides the real-time system for monitoring continuous blood sugar levels. The recorded sensor signals are processed and correlated for extracting the real-time values. The real-time transmittive green sensor values and reflective green sensor values are analyzed using Fast-Fourier Series for DC losses of GTDC and GNDC due to coarse skin layer and normal skin layer. Fast Fourier analysis is applied to $GT(G-GT)/GN(G-GN)$ to detect the signal loss parameter (GPAR). For coarser skin, the green parameter is extracted in terms of tilted green sensor (GTDC) and transmittive green sensor (GNDC) i.e. (GNDC+GTDC)/2; else the processed value of transmittive green sensor (GNDC) is directly used. The Near-IR response signals are adjusted for body temperature values and ambient environment temperature values using statistical methods, and the different resonant values of the Near-IR signals are computed. The mean of different adjusted Near-IR values is computed using NIRT=(NIRA+NIRB+NIRC+ so on till NIRN)/N. Fast-Fourier series is applied to Rtot1 to derive oscillatory signal (Rosc). The oscillatory signal (Rosc) is adjusted for blood line de losses, and then it (Rosc) is adjusted for skin losses using the derived green signal parameter (GPAR). The oscillatory signal power (Rosc) is compensated from the Near-IR signal ($|NIRT1|_f=|NIRT|_f-X1.|Rosc|_f$). Then, NIRT1 is adjusted from the IRtot and IRdis for Near-IR dispersion due to other blood particles (NIRT2=NIRT1−X1IRdis−X2.IRtot). Then Near-IR value is adjusted for red differential/dispersion signal (NIR3=NIR2+X3.Rdif). Then, the green parameter is adjusted from Near-IR signal in variable constant form and variable coefficient dependent form (NIR4=NIR3−X4.ln(GPAR−X5)). Linear and non-linear correlation is applied to different processed Near-IR values (NIR4), Color indices (C) and different recorded blood sugar calibration values for calibrating the sensors. Then, real time value of continuous blood sugar (BSL) is computed from the calibrated sensor. The sensor is re-calibrated for recognized hyperglycemic and hypoglycemic conditions. The IR sensor, red sensor, current values and calibrated values are analyzed and learnt for tracking BSL, hypoglycemic and hyperglycemic conditions. The real-time values of the continuous blood sugar and blood sugar fluctuation data are stored and displayed. On recognizing the chronic and abnormal blood sugar conditions, the system automatically alerts the life-support network of the user.

Eighth Aspect

In the eighth aspect of the invention, a method to precisely calibrate the blood sugar monitoring is provided. Initially the computed blood sugar values are evaluated for boundary values and threshold fluctuation values. Different blood glucose states of fasting glucose, pre-meal values and post-meal values are evaluated against the boundary fluctuations, threshold values and different blood sugar ranges, and the device is recalibrated accordingly. Based on the detected blood sugar condition of pre-diabetes, hyperglycemia and hypoglycemia, an automated therapy and diet recommendation is presented to the user. The dispersion values are further analyzed and learnt to evaluate the response result.

Ninth Aspect

A method to extract the blood pressure and stress levels are provided in the ninth aspect of the invention. Initially, the red signals are compensated for skin losses using parametric analysis between the green response and red response signals. Fast Fourier analysis is applied to the total and oscillatory signals of the red sensor to extract the power values of the red signal. The analyzed and noise-free red sensor values are further analyzed using non-linear or linear analysis for deducing real-time blood pressure values. The real-time blood pressure values and fluctuations are analyzed to evaluate the blood pressure conditions of stage 1 hypertension, stage 2 hypertension, pre-hypertension and low blood pressure conditions. Based on the recognized blood pressure condition, the user is presented with physician consultation message, diet and health management techniques. The blood pressure values and the temporal fluctuations of the red signal are analyzed through different methods and parameters of user location, user state and user postures. The analyzed blood pressure values and the temporal fluctuations are utilized to evaluate the psychological stress levels of the user. During the state of psychological stress, the user is automatically presented with stress management methods. On recognizing severe blood pressure condition and state of psychological stress, the system automatically alerts the life-support network of the user.

Tenth Aspect

An automated sleep tracking system is presented in the tenth aspect of the invention. The accelerometer signals, body temperature, blood pressure data and blood sugar values are initially evaluated for state of sleep. The variations in blood pressure and blood sugar values are compared against the wake levels, and then derived HP1, HP2 and HP3 parameters are furthered analyzed for recognizing NREM sleep cycle and REM sleep cycle. The computed sleep cycle and time period of the respective sleep cycles are incremented and stored. The actimeter signals are evaluated to verify if the user's sleep is disrupted. On recognizing the state of disturbed sleep, the health and life-style recommendations are provided to the user. Further learning is applied to the signals to simplify the sleep recognition process.

Eleventh Aspect

The eleventh aspect provides a method and software device to calibrate the device. The user data of profile picture, age, BMI, fat %, gene info, weight and height are recorded through the telemetry apparatus or the accessorial mobile apparatus. A picture of the contact surface is recorded and processed through the aforementioned method. The blood sugar and blood pressure calibration values are recorded for different instances of fasting glucose values, before bedtime, before lunch, before dinner, after breakfast, after sleep, after dinner, after lunch, and after exercise. The user can also record information on the micro-nutrition and macro nutrition, and meal-information through the telemetry apparatus or the accessorial mobile apparatus. The real-time information and data trends on blood sugar levels, blood pressure levels, neural activity, pulse rate, oxygen saturation and body temperature are automatically displayed on the device along with health sense message. The device comprises of automated real-time reminder and alert system to notify the user during the instances of medication and chronic medical conditions. The device further comprises of recommendation system, which guides the user with health practices and diet management techniques for the diagnosed health condition.

Twelfth Aspect

The twelfth aspect shows an optimization method for estimating the health and calibration parameters from the previously recorded data of the user database. The color index, age, BMI, fat %, gene Info, sensor intensity, signal response and real-time calibration values of the user are matched with the previously recorded parameters in the database. The optimization parameters of color index, sensor calibration data, healthy H.R. index, performance index and progress index are learnt and derived from the central database. The optimization parameters are returned to the user device, which is used in processing the real-time biological information and other health parameters.

Thirteenth Aspect

In the thirteenth aspect, a parallel computational network is provided. The parallel computational network enables the computation with much higher speed and efficiency, while keeping the complexity low. The network of parallel computation network comprises of internal microprocessor, external server computers, accessorial mobiles devices, external computers and other synchronized devices. The external servers are used for executing computational process, and as well as for remotely storing the information. The accessorial mobile devices and other synchronized devices are also used to compute and store the information. The network of parallel computing devices are accessed through wireless methods of 'WLAN, BLE, GSM' and through other possible modes of communication. Whenever necessary, stored information and computed results are communicated between the telemetry apparatus and network of devices.

Fourteenth Aspect

An emergency response system is presented in the fourteenth aspect. On recognizing emergency trigger, the system validates the status of the wireless antennae and switches it on. The location data are recorded through the wireless antennae set, and the biometric and other vital information are recorded through the internal bio-sensors. The recorded information is transmitted to the central server, SOS network, support network and to the near-by mobile devices through the wireless methods. The devices are synchronized, and the next set data are transmitted. The wireless data transfer occurs directly or via medium of central server.

Fifteenth Aspect

The fifteenth aspect of the invention provides a single clipper based ring embodiment form of the telemetry apparatus and the optical spectrometer. The ring comprises of a main body frame and an extending clipper element. The signal probe set of Near-IR spectrum, Infrared spectrum, red spectrum, tilted green spectrum and transmittive green spectrum, and the set of Near-IR photodetector, Infrared photodetector, red photodetector and green photodetectors are packaged on the inner contact surface. The photodetectors are placed in the alignment with their corresponding signal probes for recording the optical response. A non-contact temperature sensor is placed on the inner contact surface, which is utilized to record the temperature response of the body. The inner surface of the ring comprises of a sponge base, which is used to reduce the contact vibrations during the real-time measurements. A micro-USB port is embedded on the side surface of the ring apparatus, which is utilized for charging the device and for data transfer purposes. A fancy LED is embedded inside the ring's frame, which is used for indicating different device operating modes and also for representing decorative applications. The device comprises of navigator crown and buttons, which are utilized to operate the telemetry apparatus. A coil is placed inside the device, which is utilized as a wireless means to power the device and charge the device battery. The speaker and mic are embedded on the device, which are used to attend the phone-calls, perceive different responses and operate the apparatus. The clipper element of the device comprises two clips and two hinges, which are used as a size-adjustable feature to fasten the device. The overall device is covered with a water-proof coating.

Sixteenth Aspect

In the sixteenth aspect, a dual clipper based ring embodiment form is provided. The ring comprises of optical spectrometers of green optical spectrometer, Near-IR spectrometer, red and IR spectrometer. A disposable foam base is placed near the sensors to reduce the movement errors in the real-time recording. The device comprises of button set and navigator, which are used to operate the device. The device is fastened to the user with the help of the holding clips. The holding clips are affixed on the upper and lower side of the ring through clip hinges. The holding clips has extender hinges in the middle of the holding clips, which are used to adjust the grip size.

Seventeenth Aspect

The seventeenth aspect of the invention presents a solar module powered portable telemetry monitoring embodiment form. A transmittive sensing spectrometer with foam base is embedded on the finger placement area of the apparatus. A set of buttons are embedded on the side surface of the device, which are used to operate the device. A USB port is attached on the side surface of the device, which is used to transfer data and to power the device battery. The device comprises of touch-screen, which is used as the means to access the information and operate the telemetry apparatus. The back surface of the device is attached to a solar module. The solar module has an actuatable module 1 and actuatable module 2, which are attached to each through an actuatable hinge. The actuator hinge along with an actuator automatically extends the solar module for absorbing more solar energy. The solar module is used as an auxiliary renewable powering unit. The device further comprises a wearable chord with molded extender clip and extender chord, which is used as a method to modify the size of the chord. The device is further coated with water proof coating.

Eighteenth Aspect

In the eighteenth aspect of the invention, an earphone based embodiment form is presented. The device has transmittive sensing spectrometer near earlobe attachment area. A fancy LED is embedded in the ear hook of the device, which emits light to represent different operating modes and device status. The music ear-buds are attached to the rear-end of the device. The ear-bud and ear-hook are used to fasten the device to the user.

Nineteenth Aspect

The nineteenth aspect of the invention presents a fancy LED apparatus. The fancy LED device comprises of multi-colored LED encased in a line of multiple optical tubes. The light emitted by the fancy LED is observed inside the multiple optical tubes.

BRIEF DESCRIPTION OF THE ARTWORK

Figure 10:
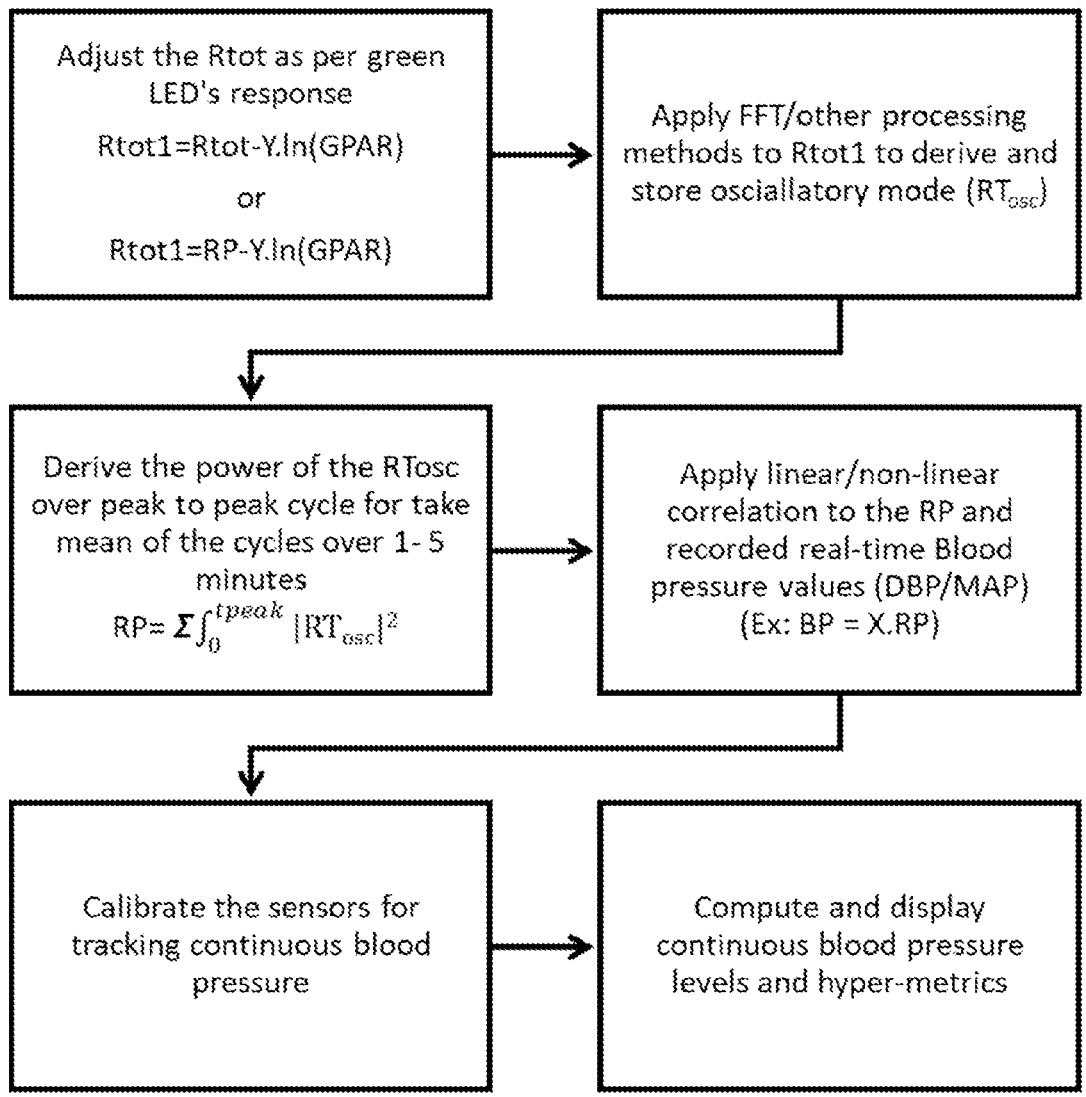
Figure 12:
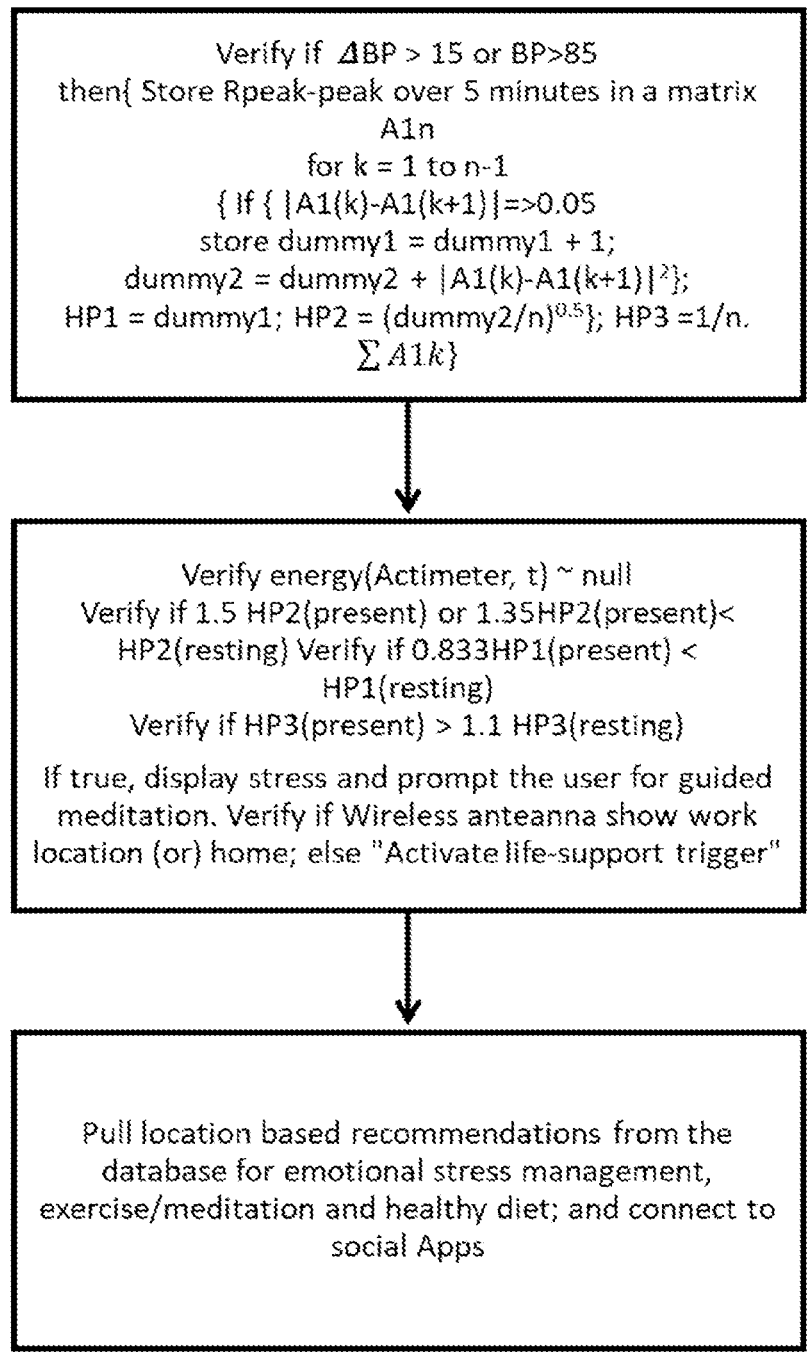
Figure 13:
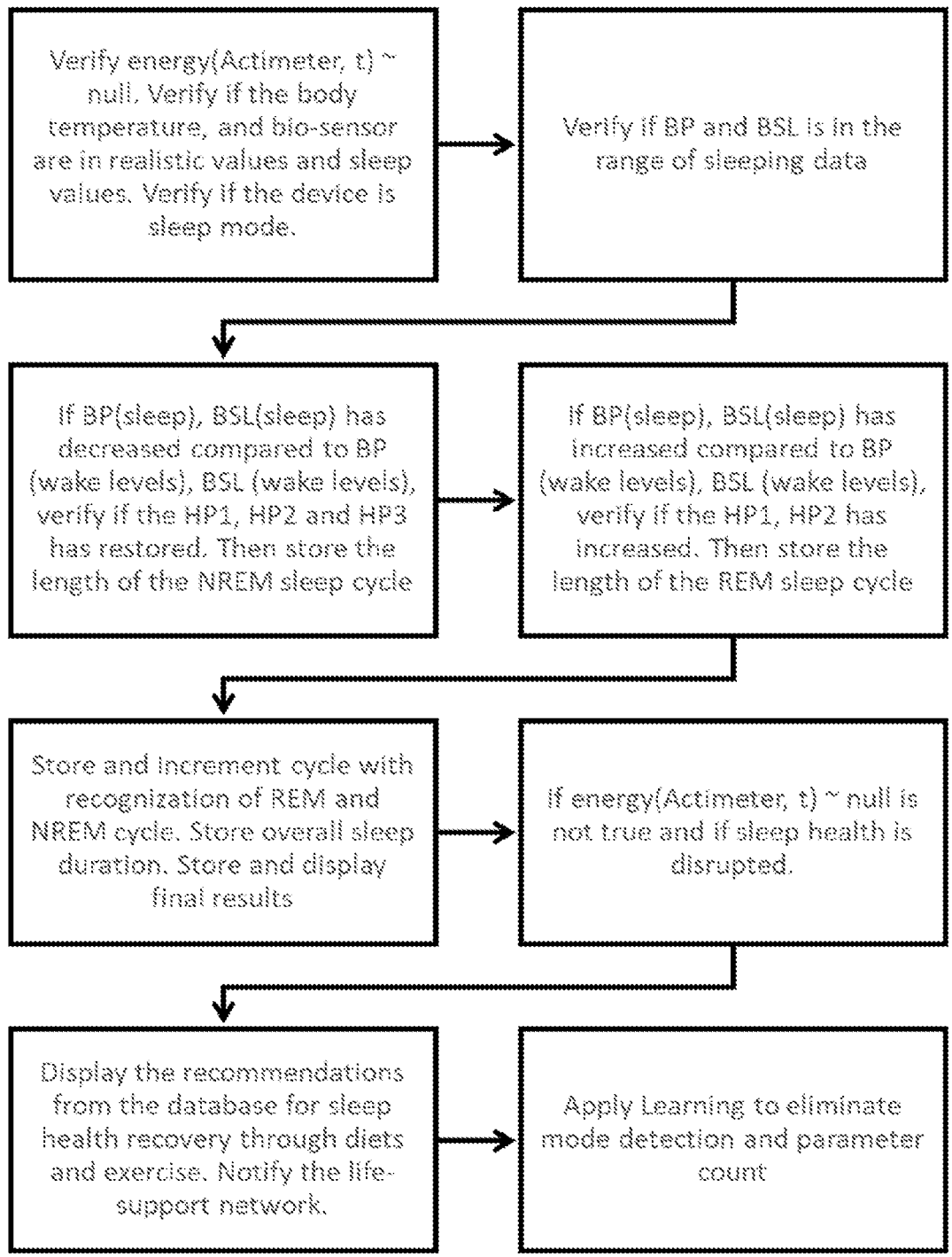
Figure 14:
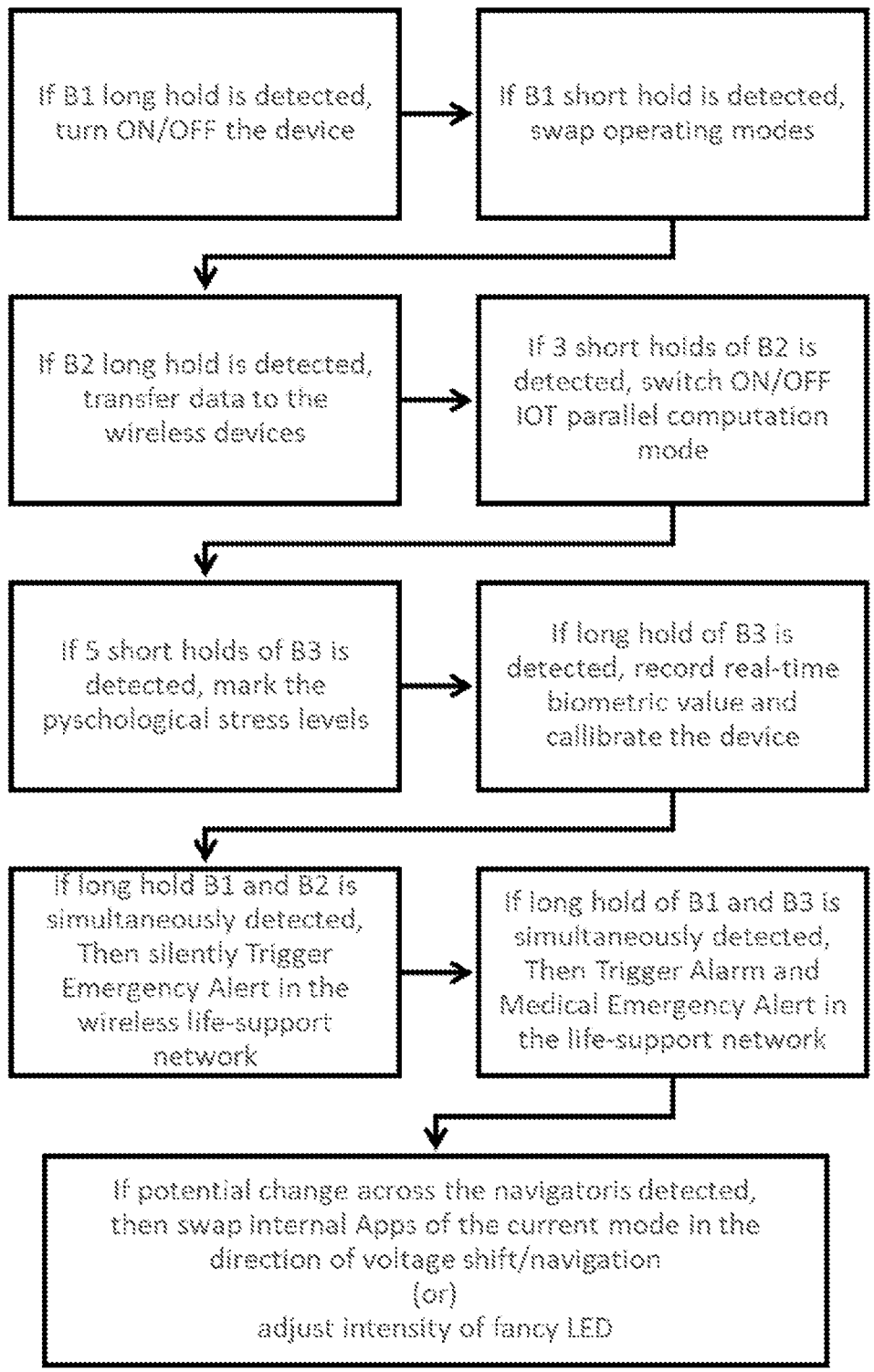
Figure 15:
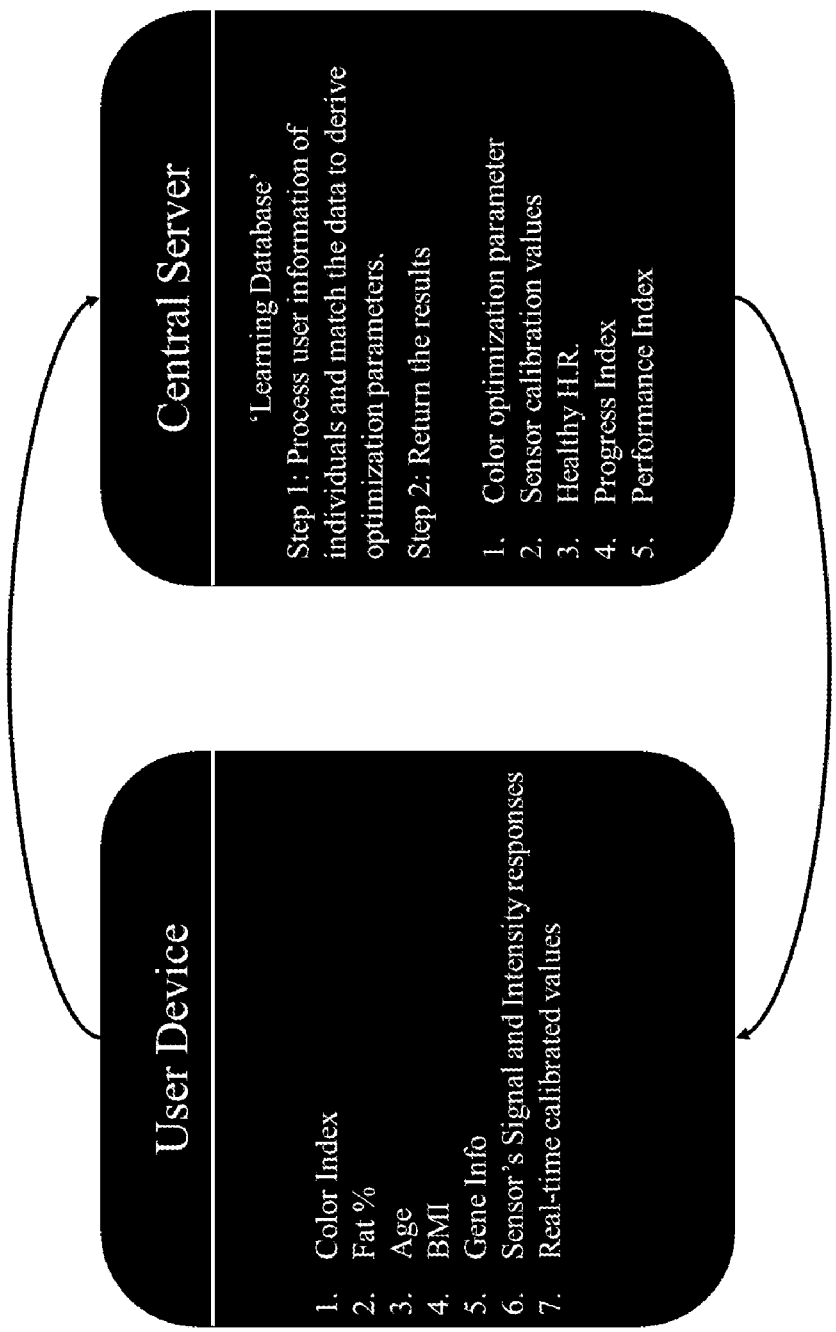
Figure 16:
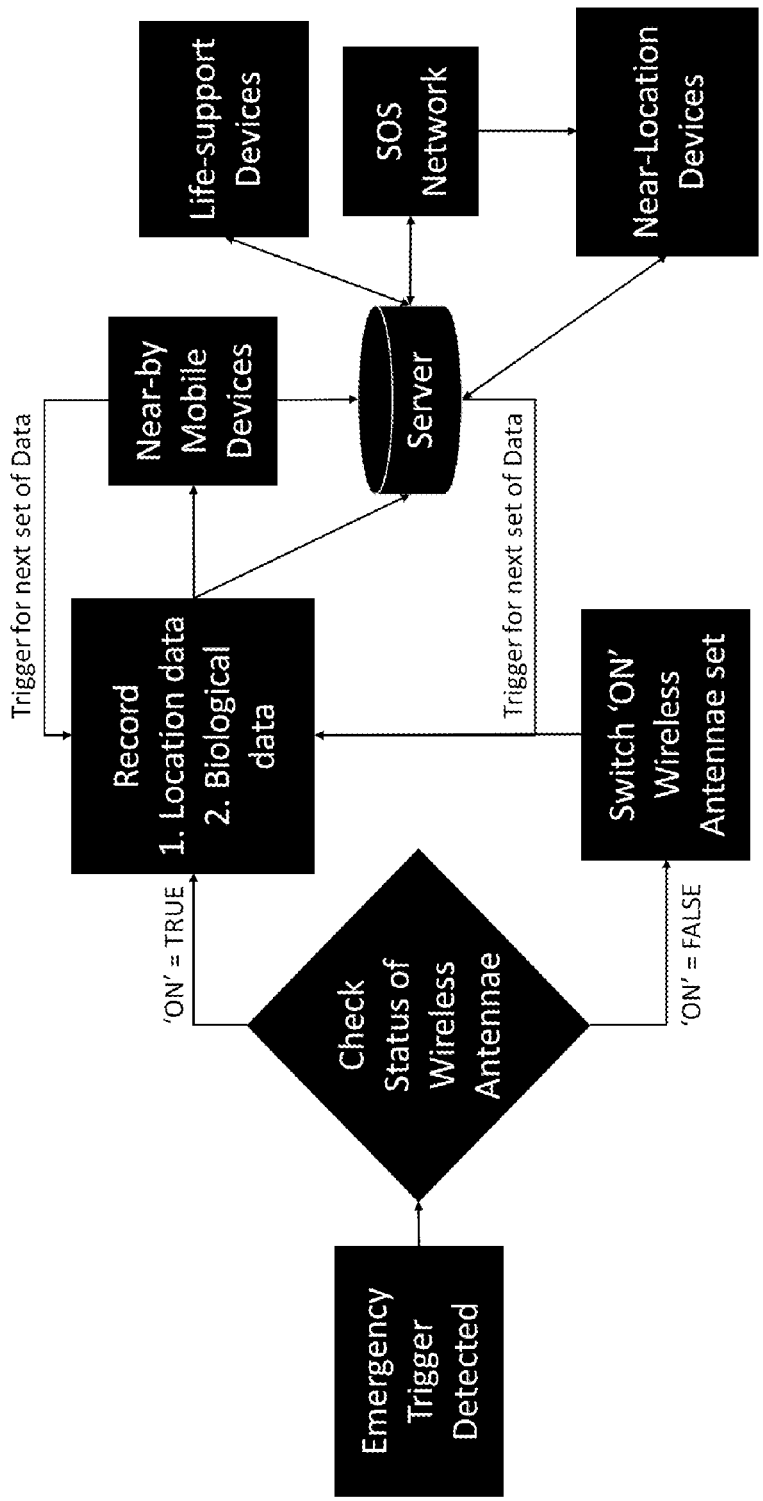
Figure 17:
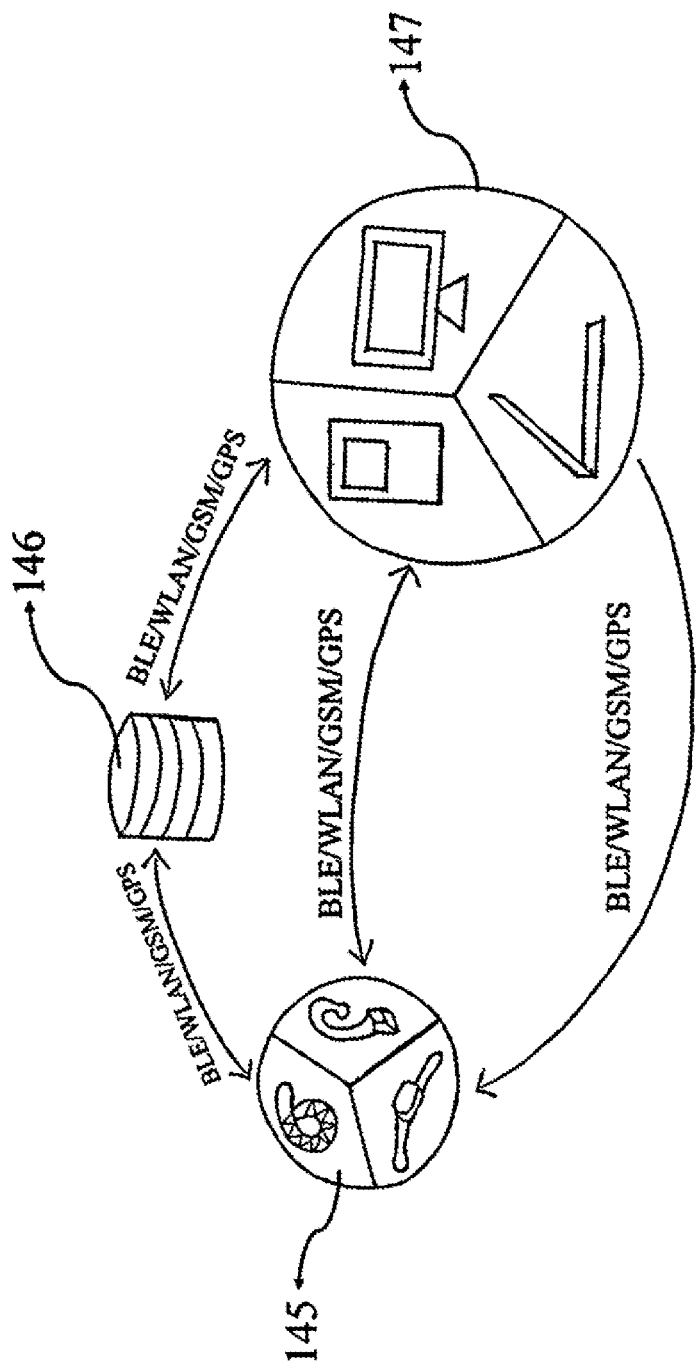
Figure 18:
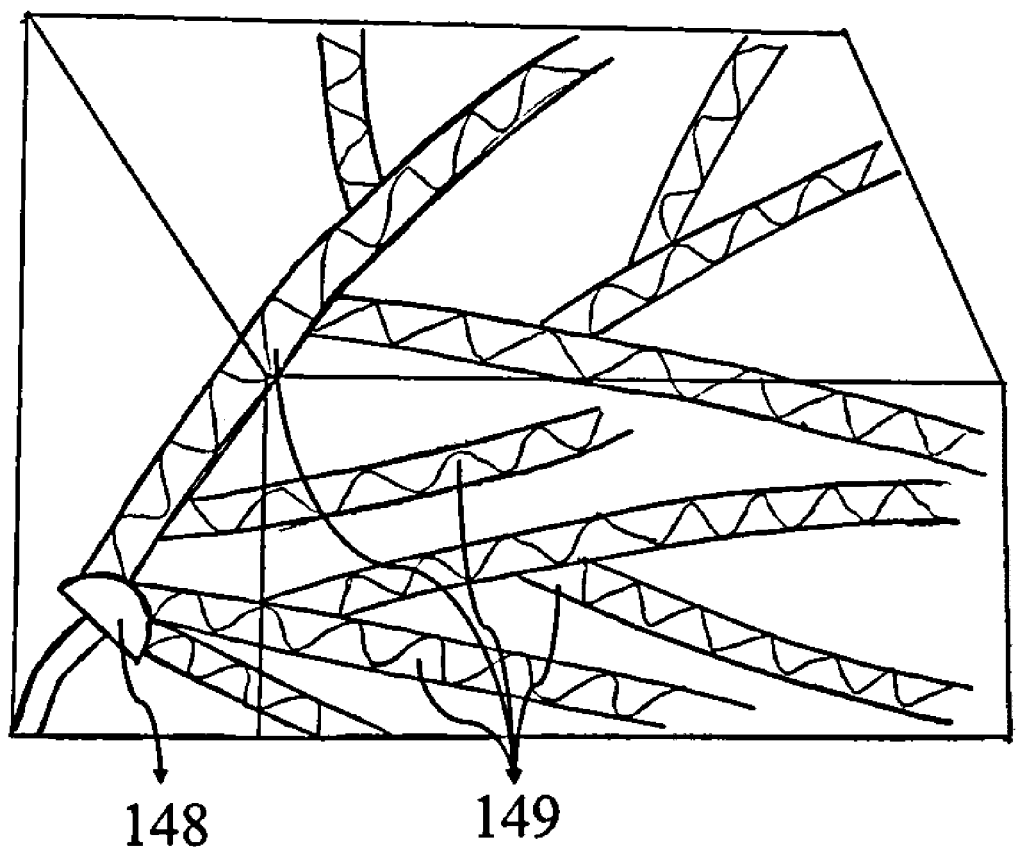
Figure 19A:
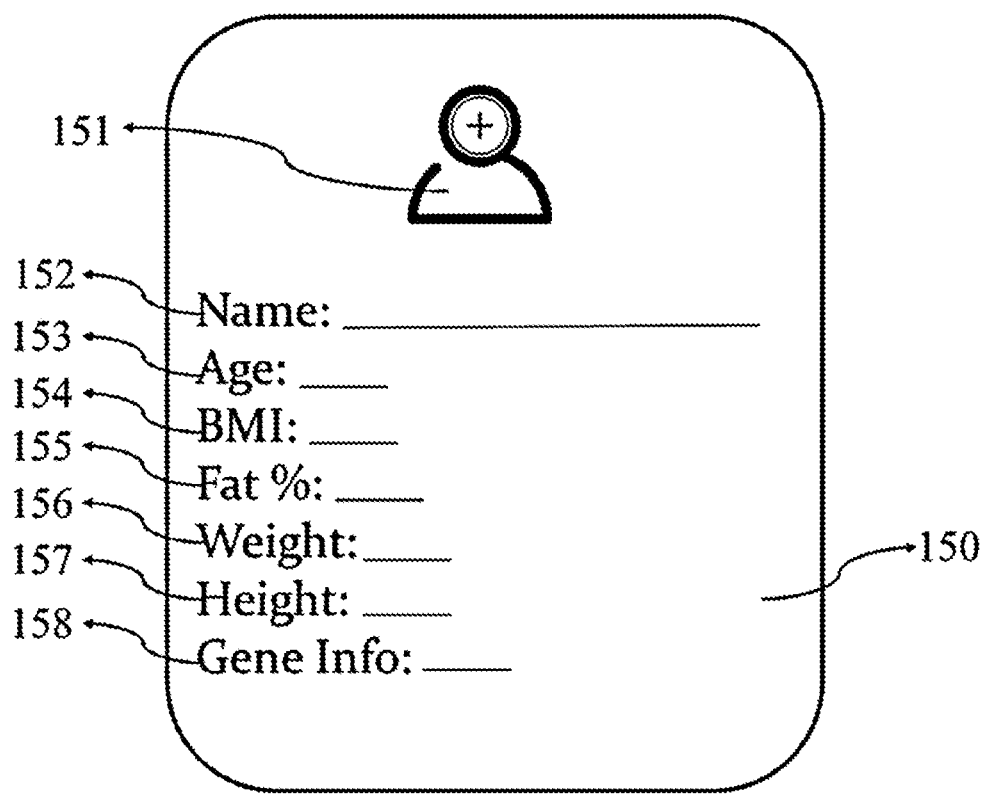
Figure 19B:
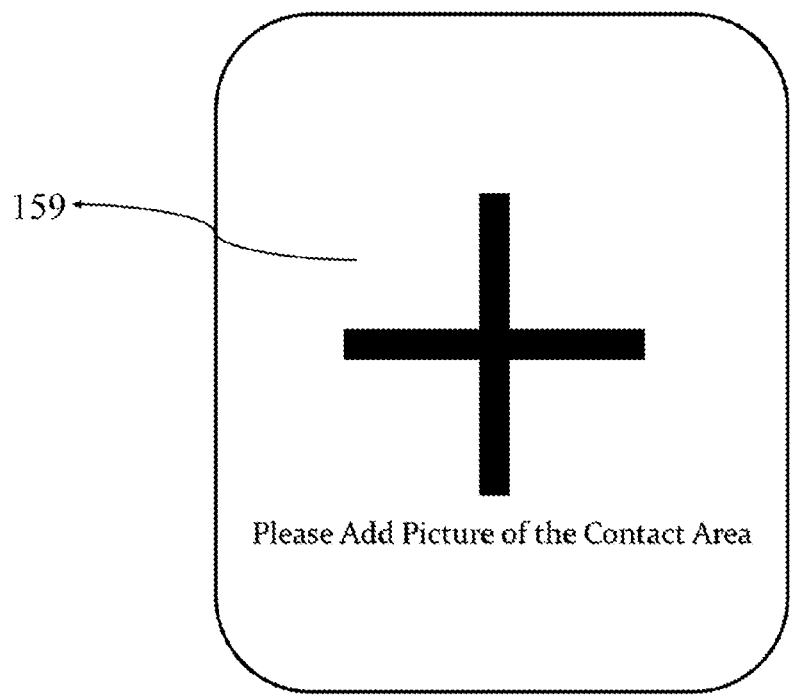
Figure 19C:
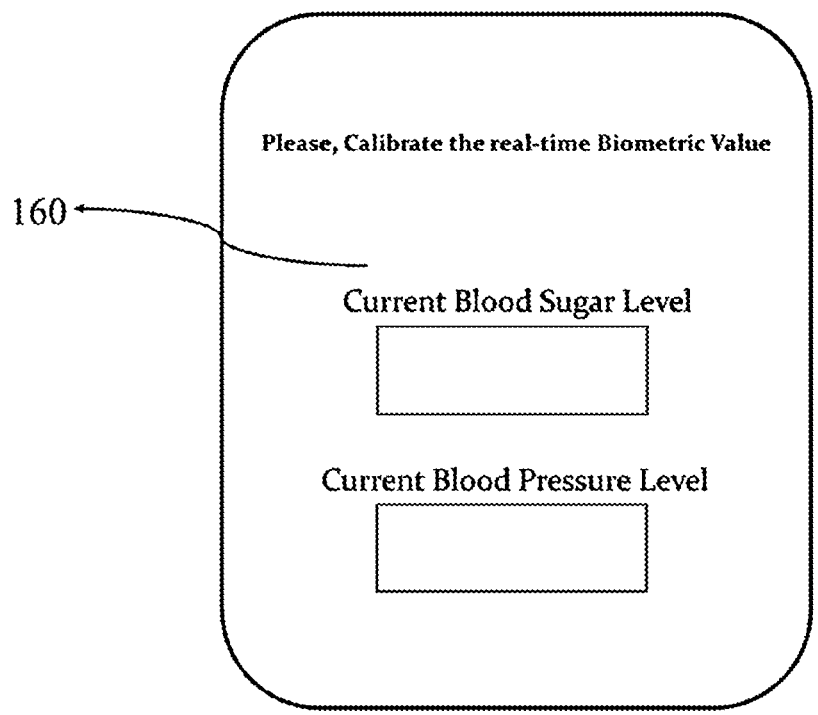
Figure 19D:
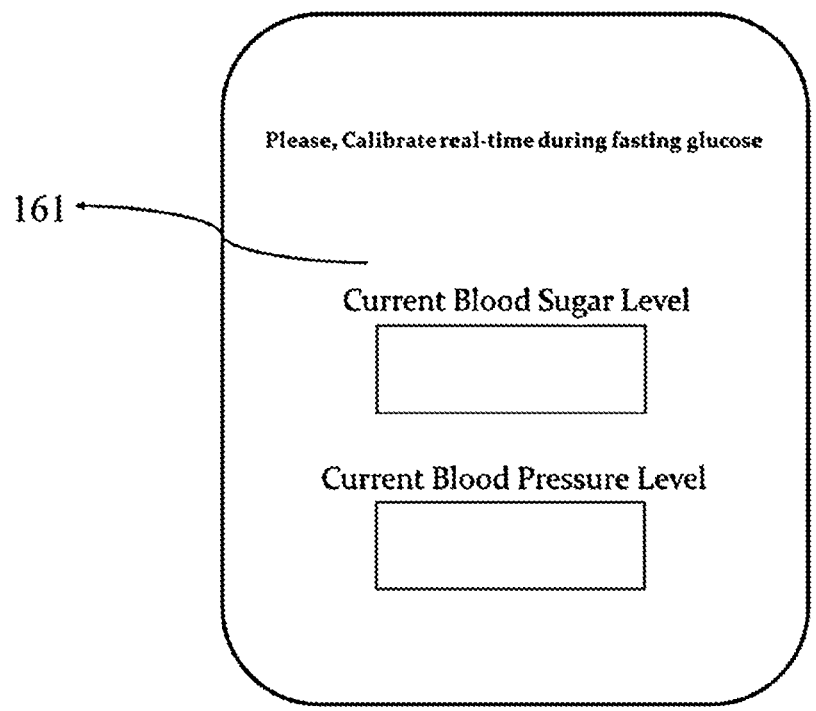
Figure 19E:
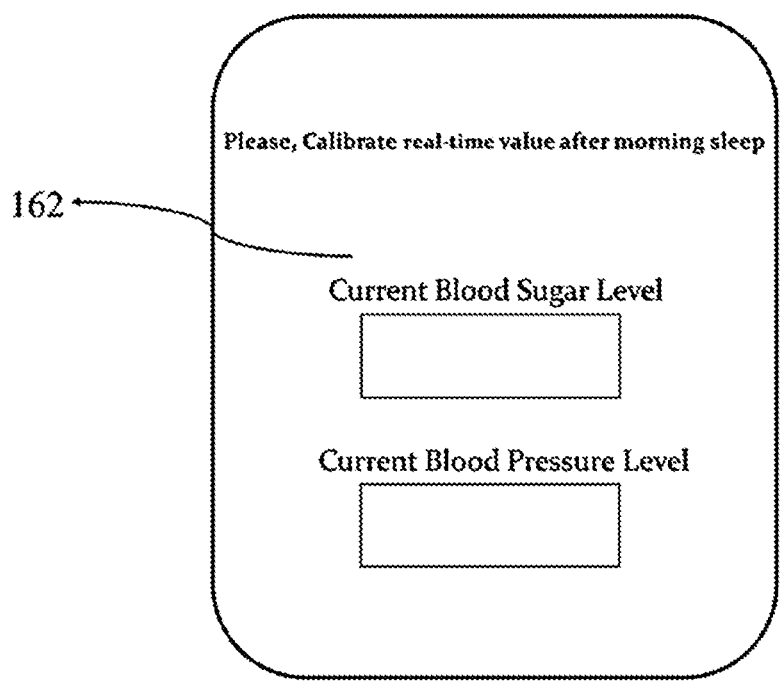
Figure 19F:
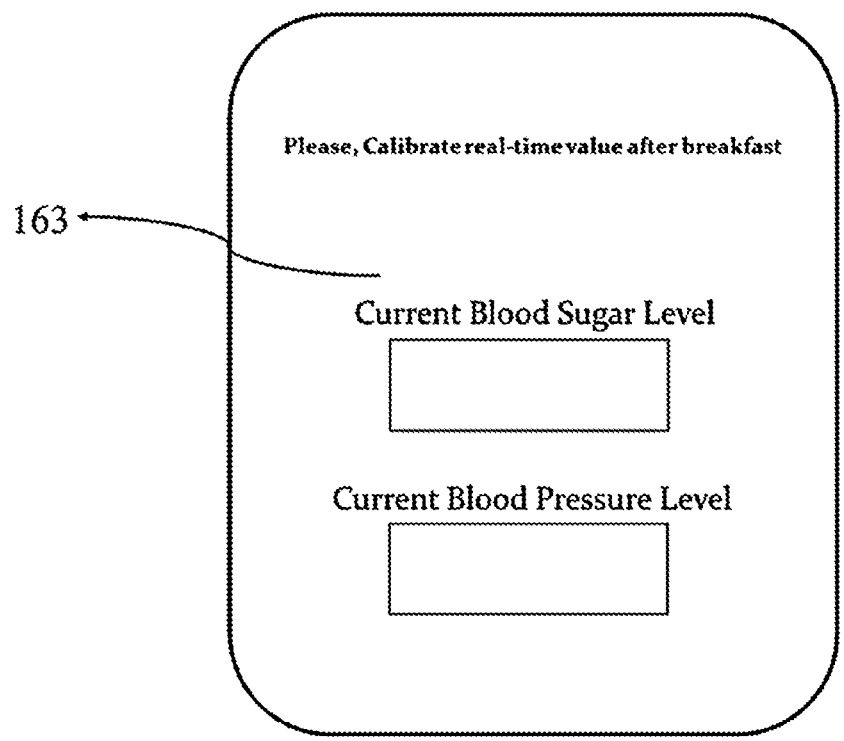
Figure 19G:
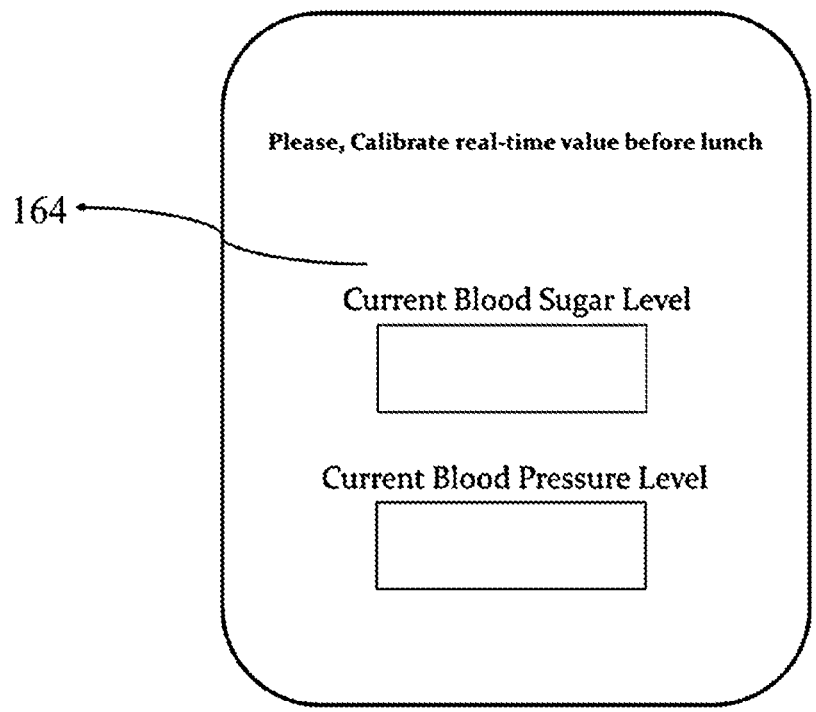
Figure 19H:
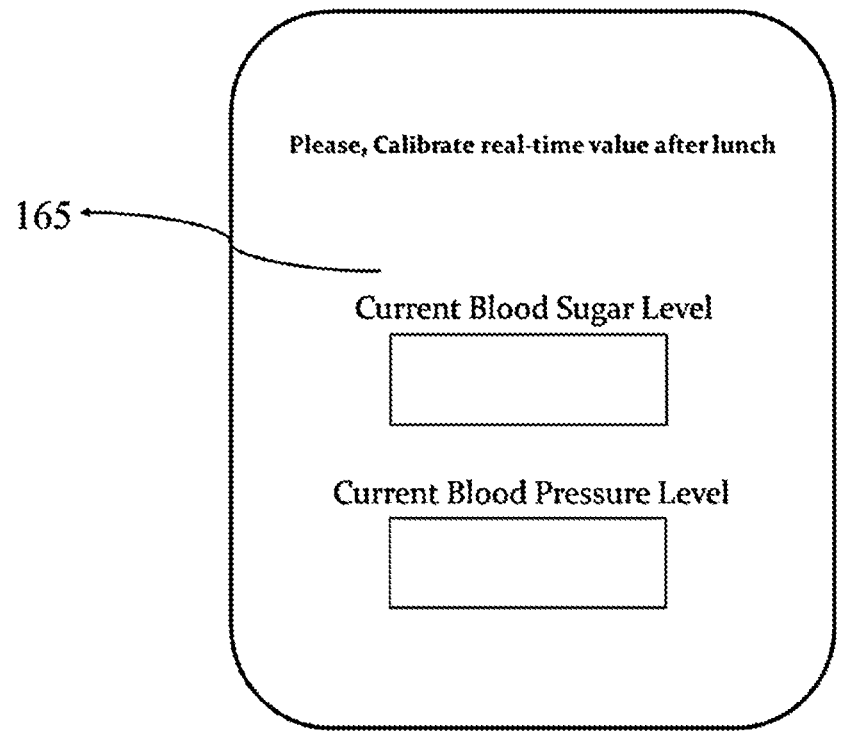
Figure 19I:
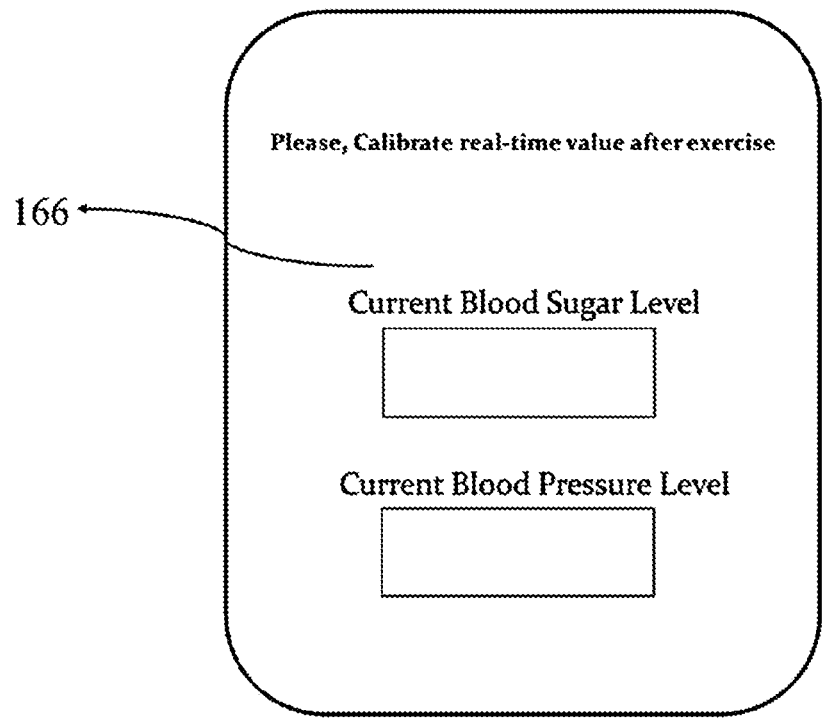
Figure 19J:
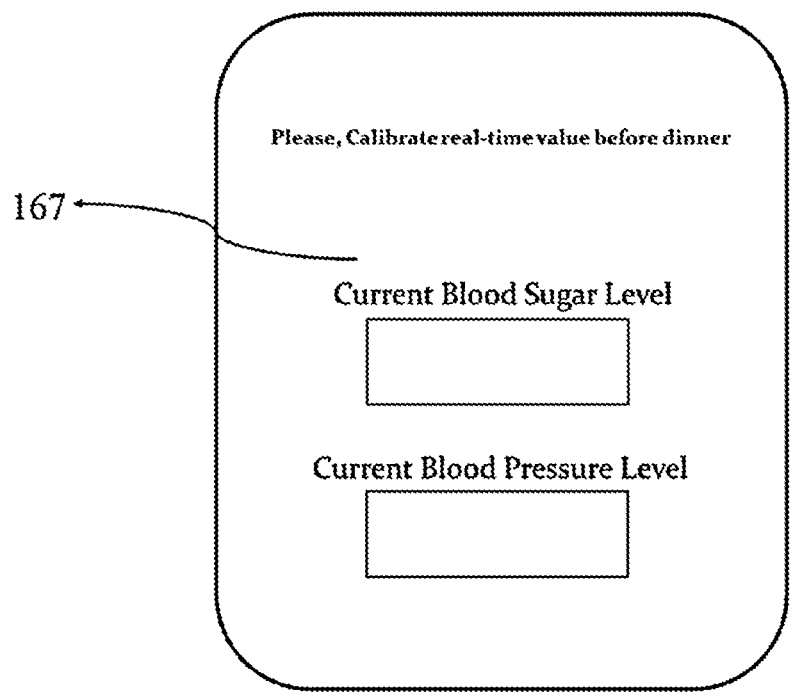
Figure 19K:
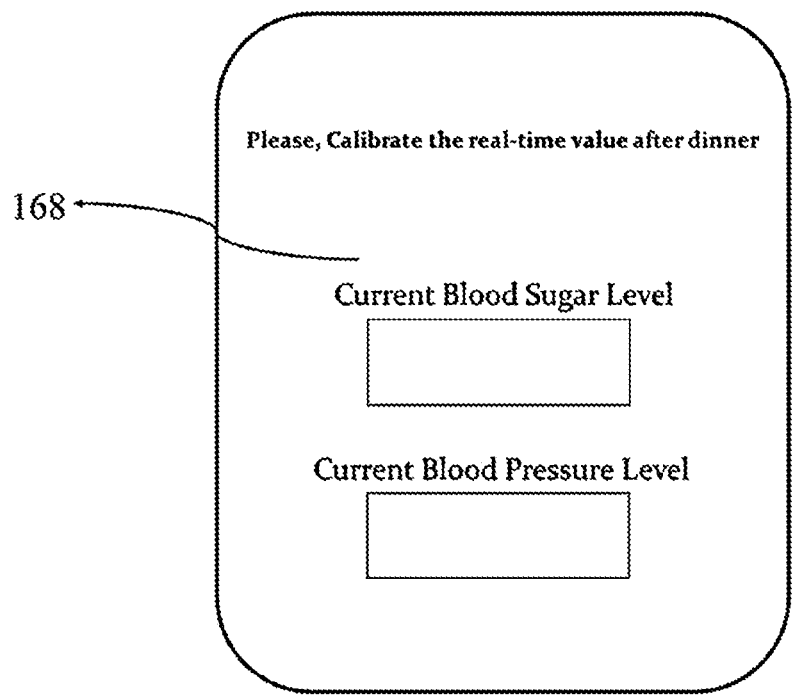
Figure 19L:
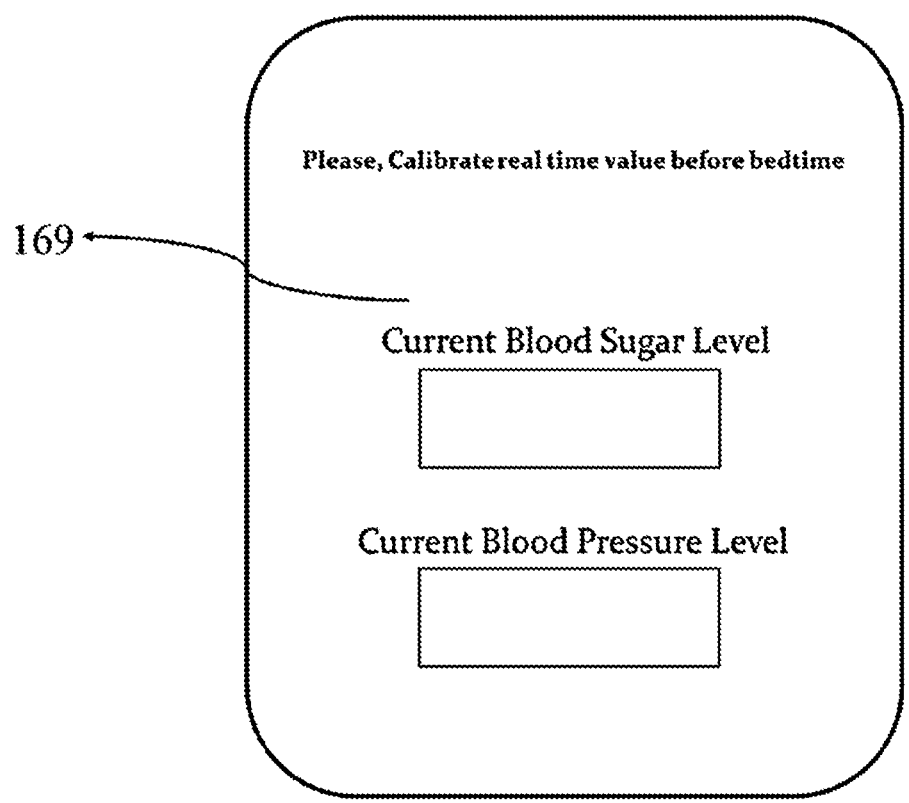
Figure 20:
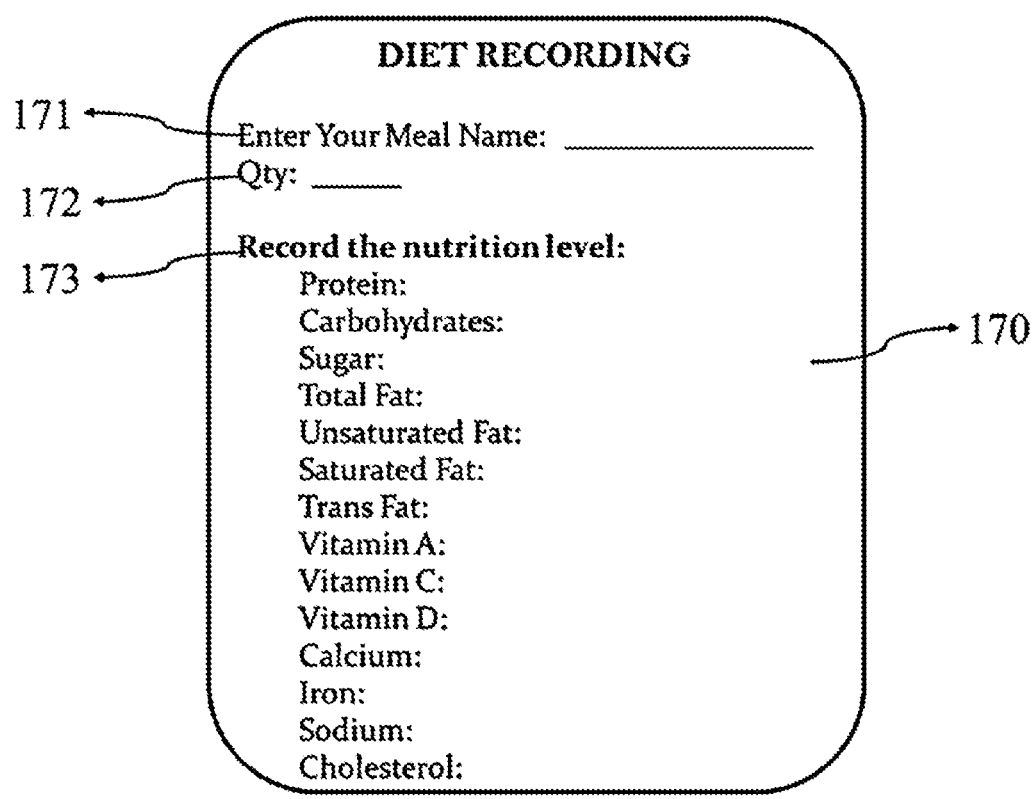
Figure 21A:
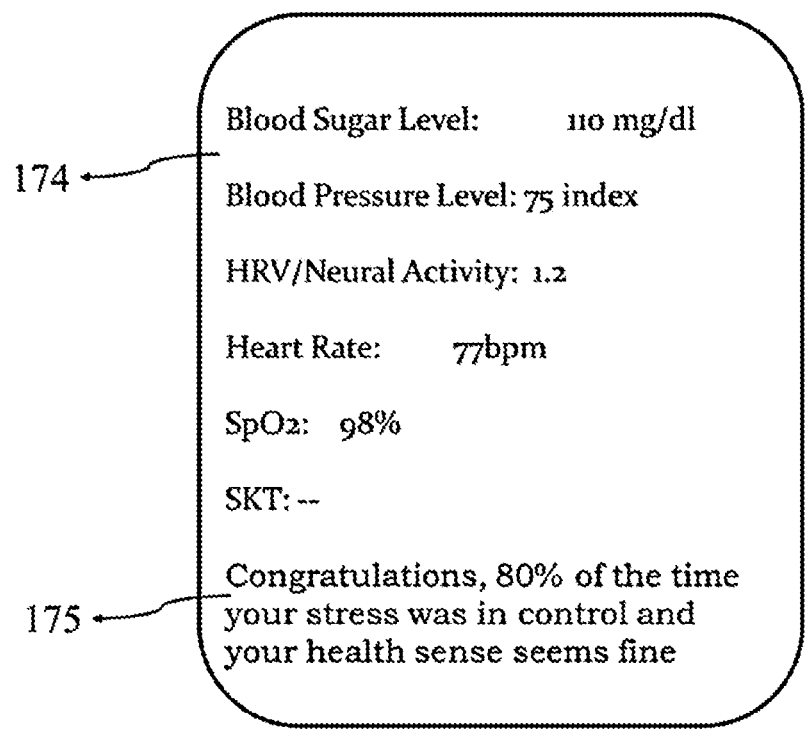
Figure 21B:
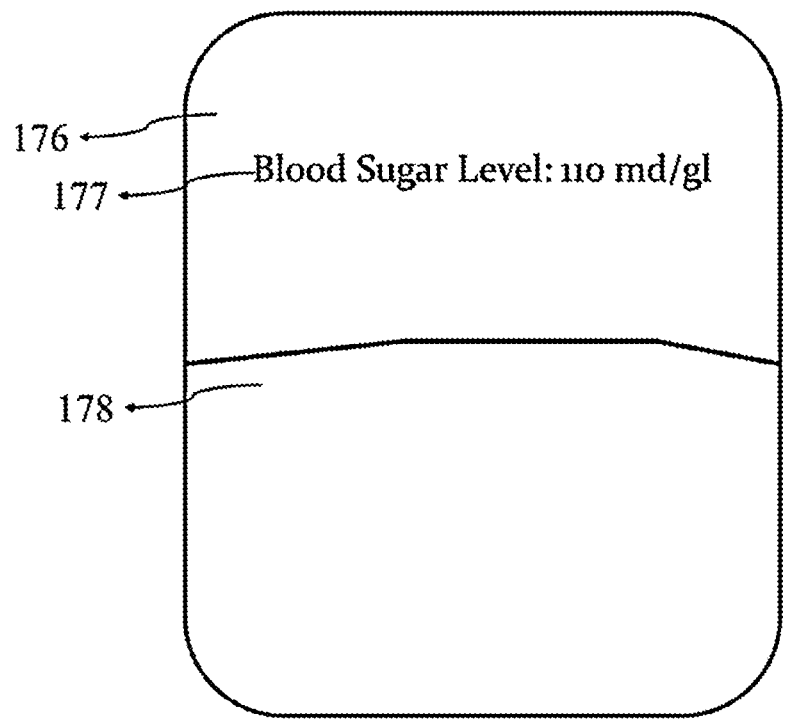
Figure 21C:
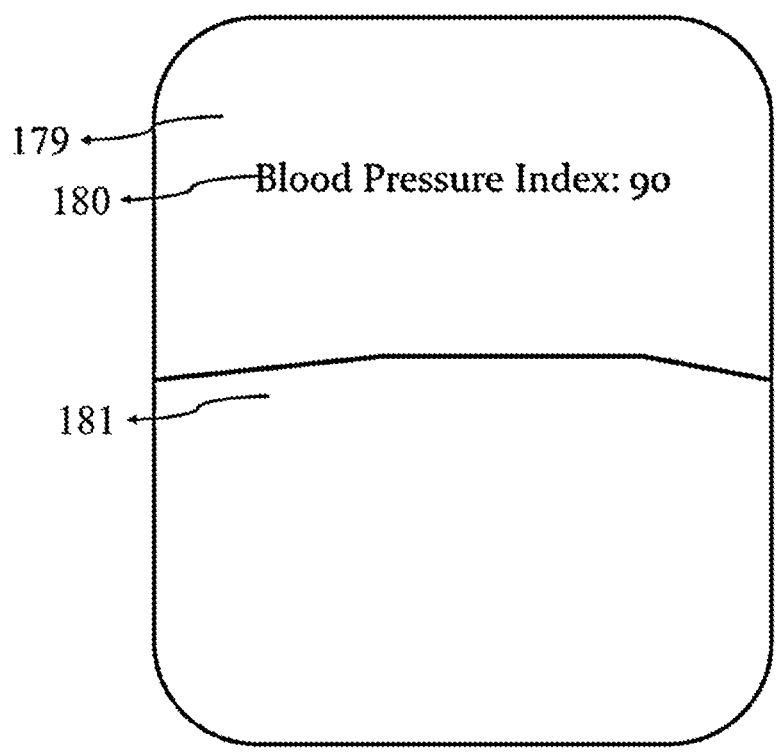
Figure 21D:
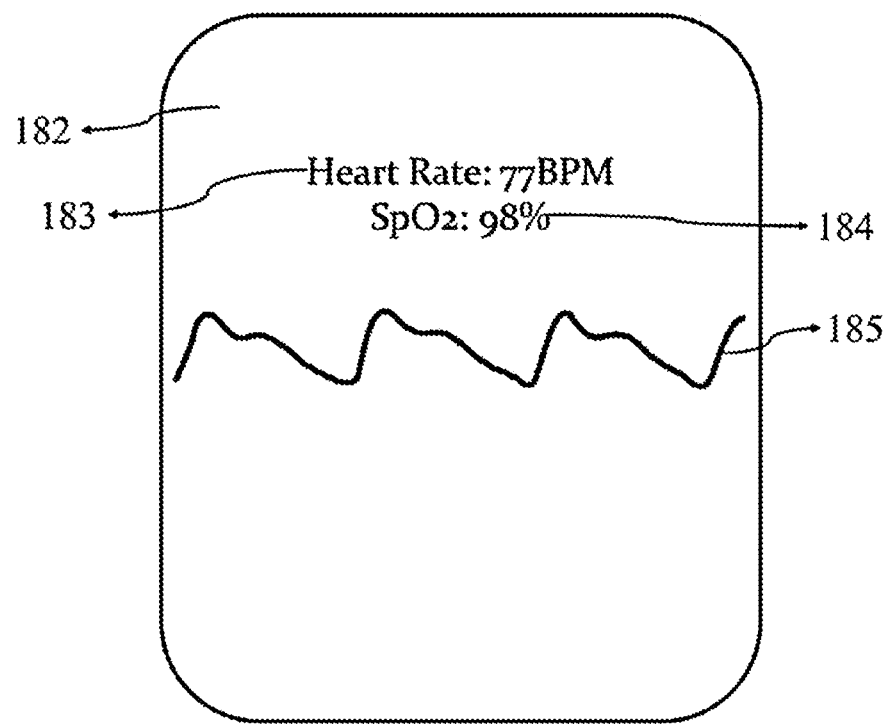
Figure 25A:
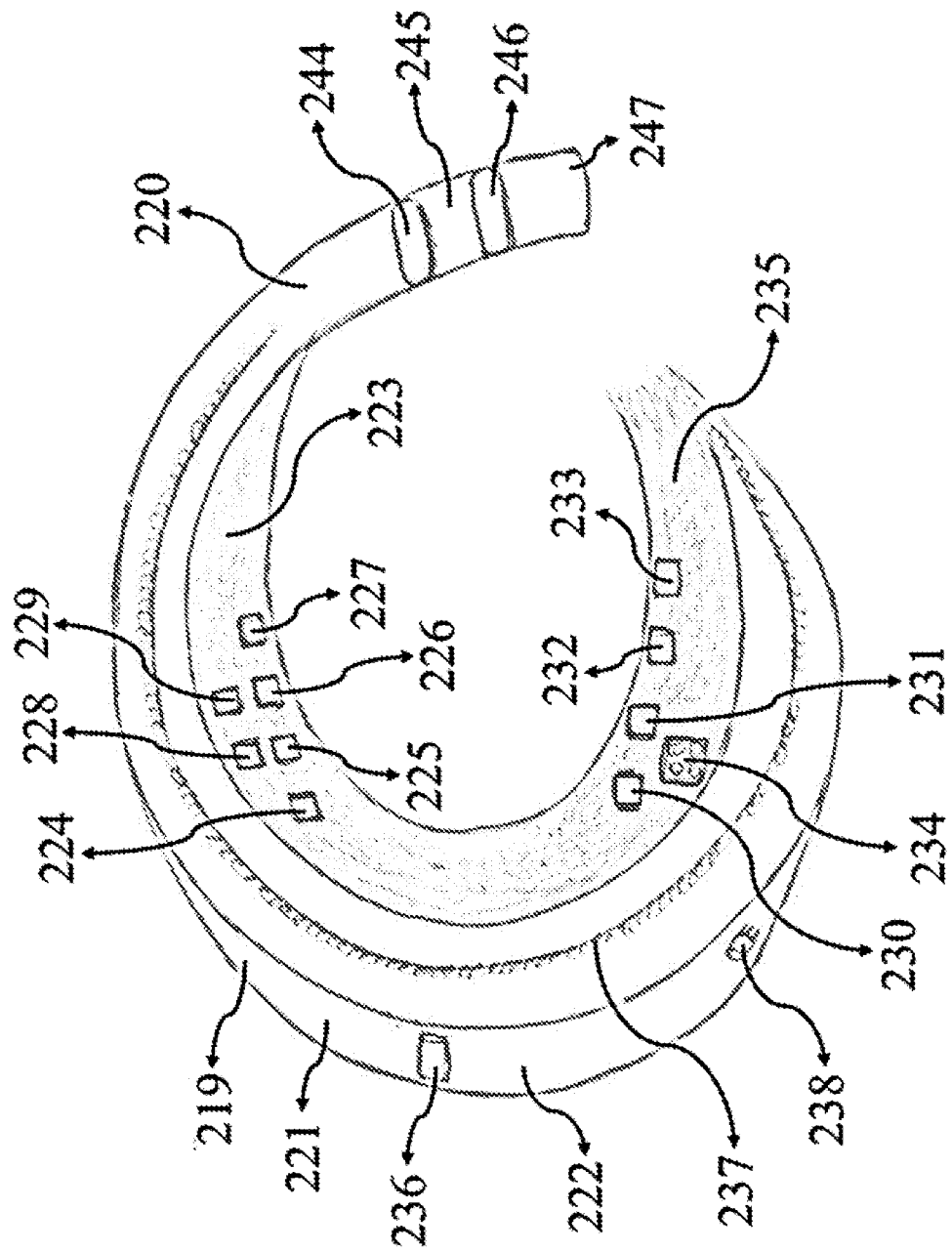
Figure 25B:
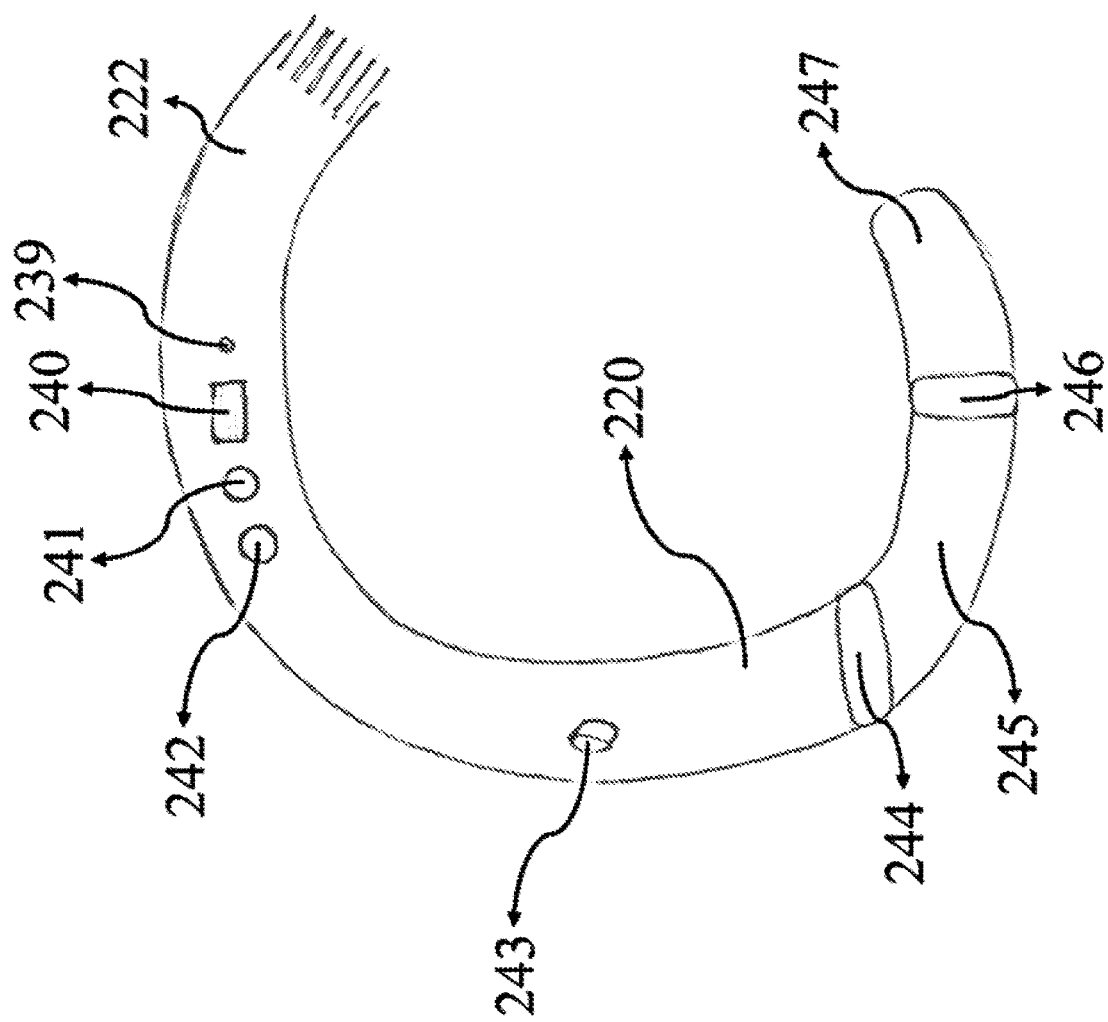
Figure 26:
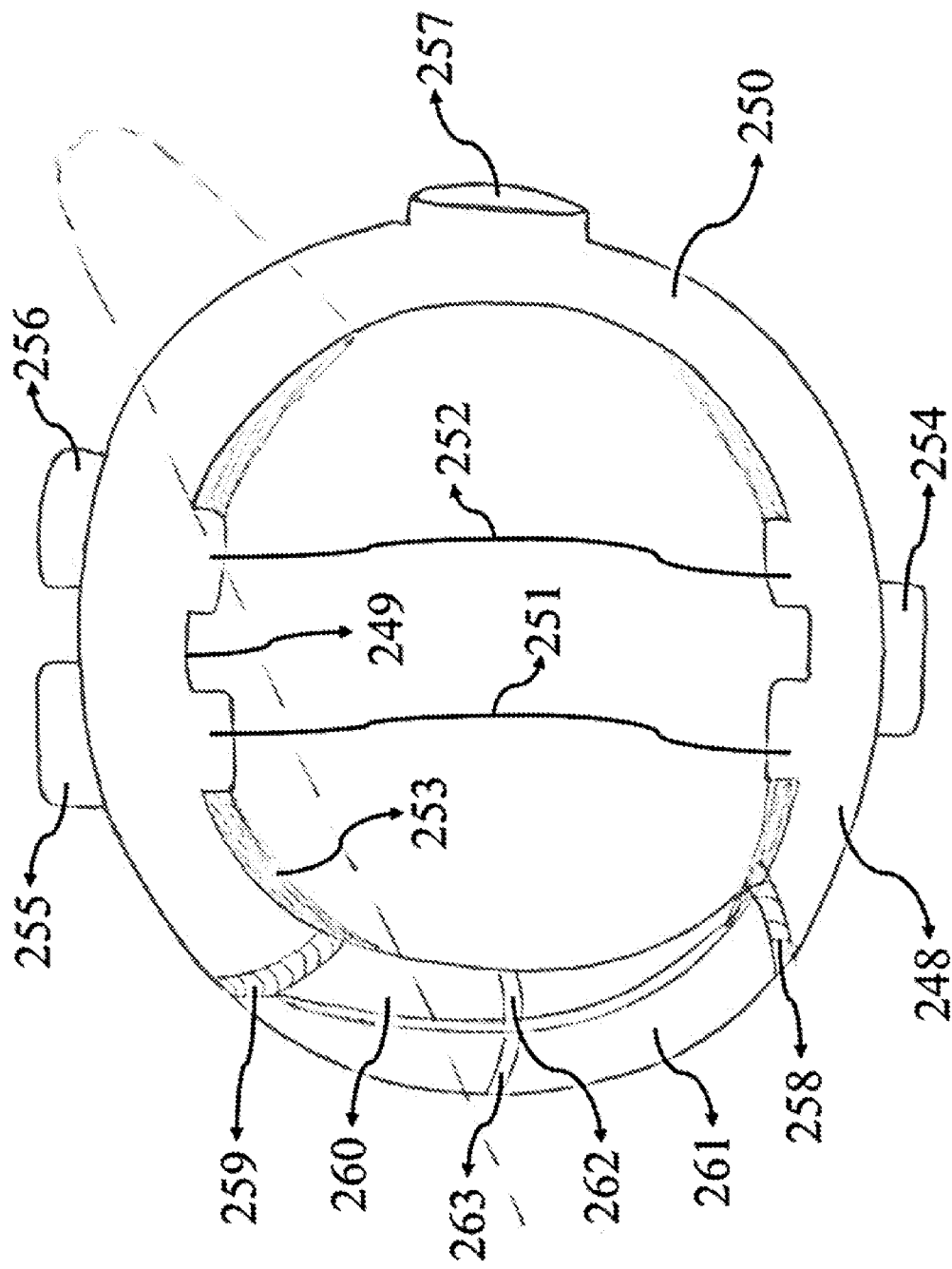
Figure 27A:
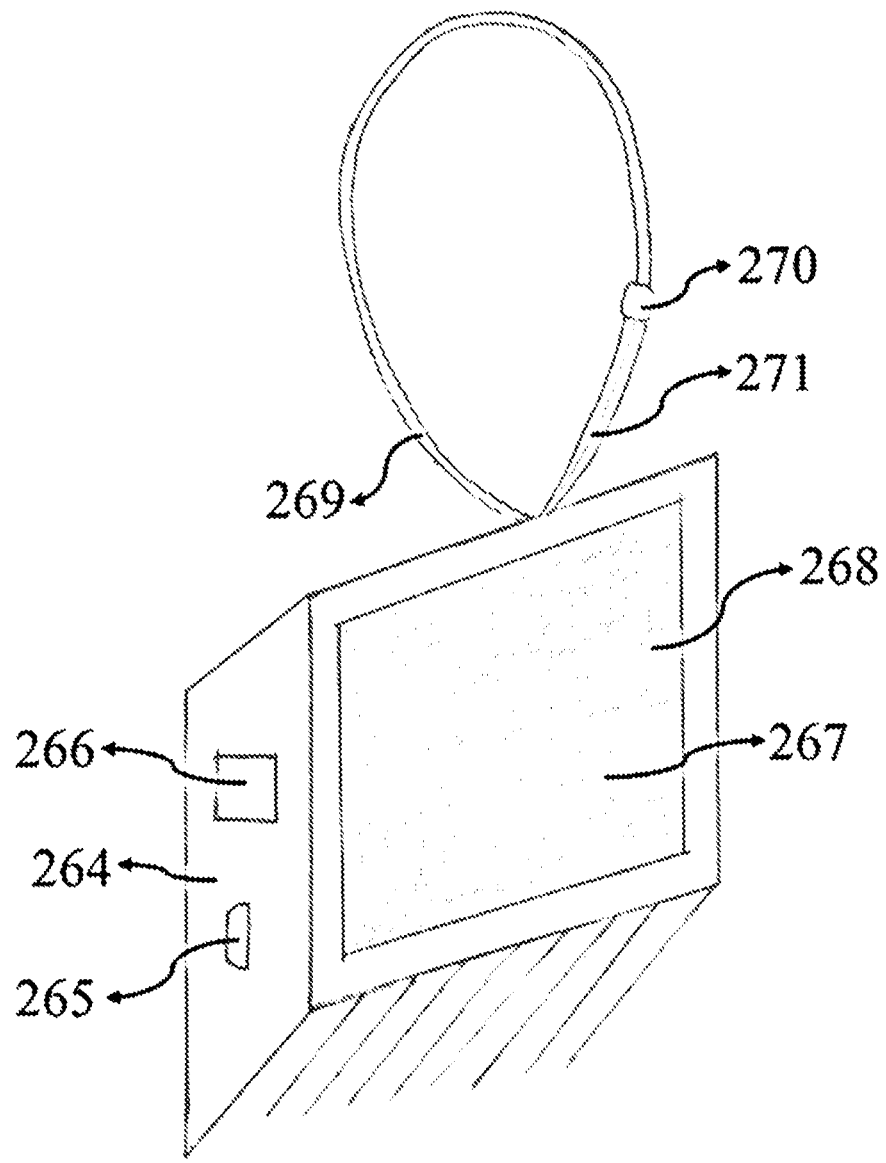
Figure 27B:
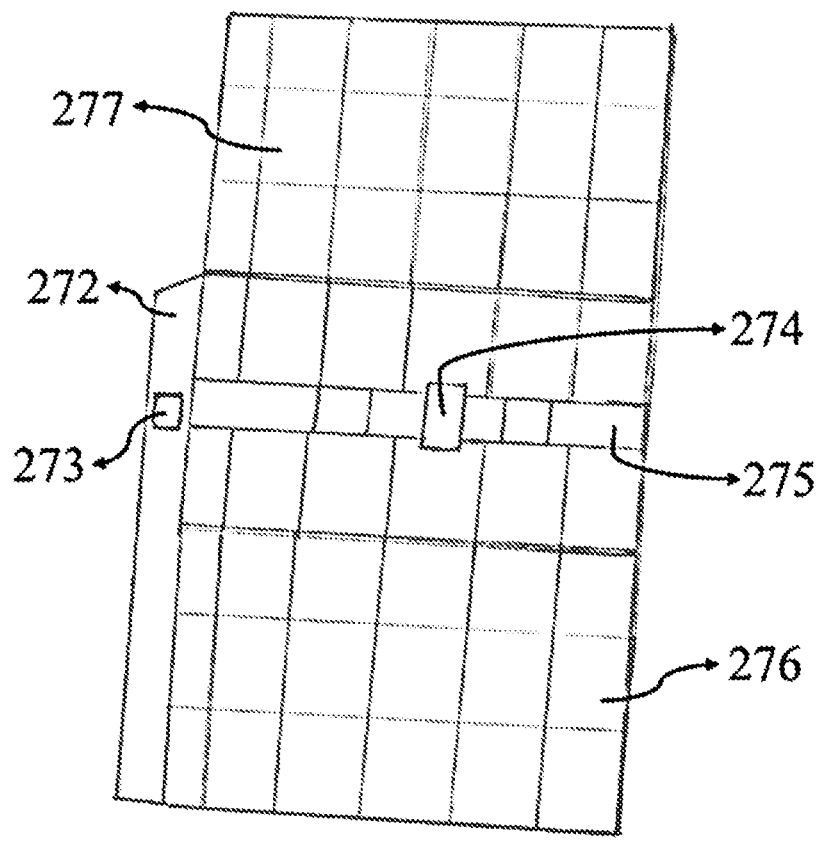
Figure 27C:
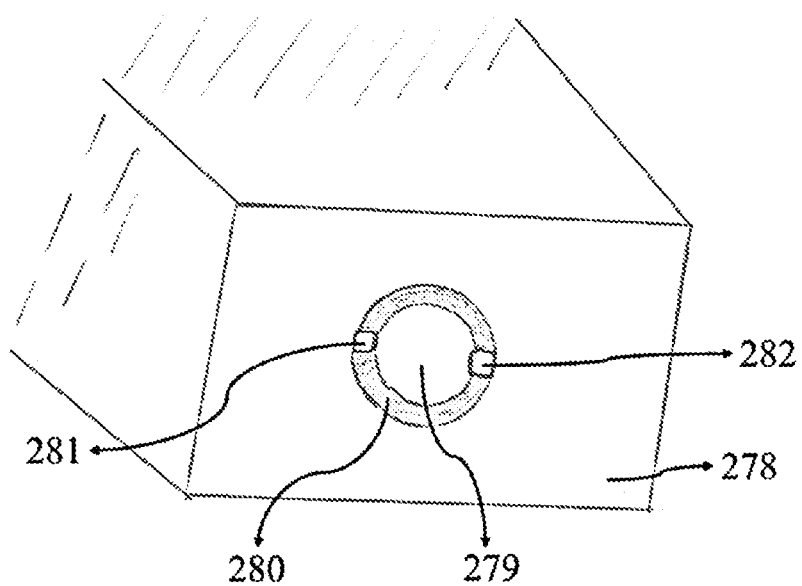
Figure 28:
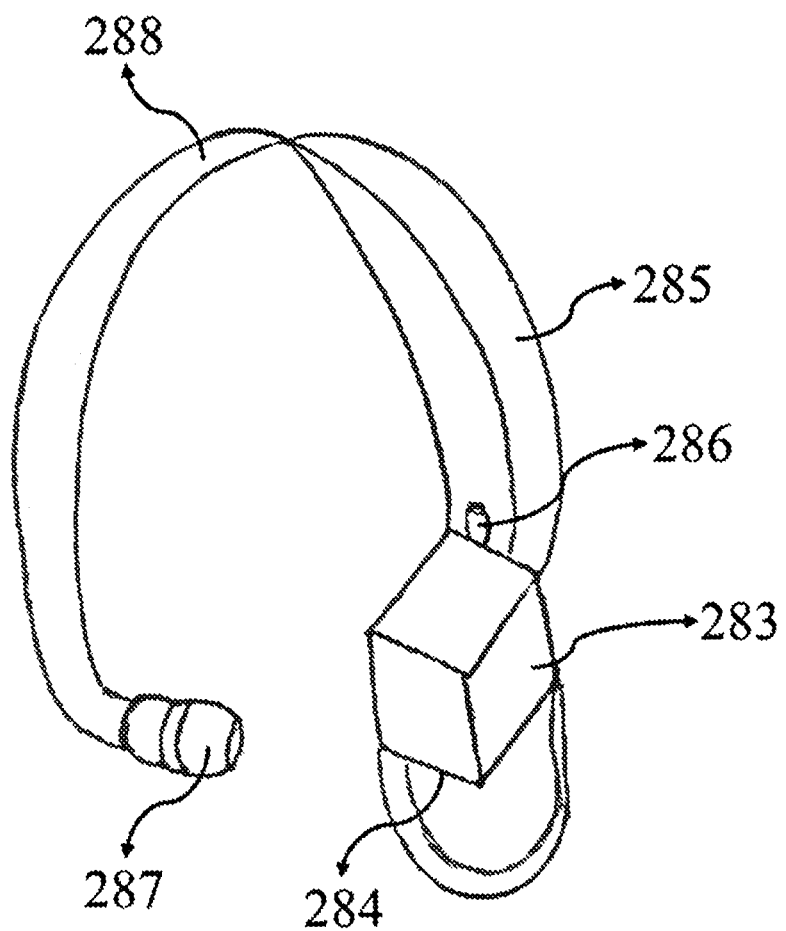

Series of FIG. 6 show the method to calibrate the telemetry apparatus;

Series of FIG. 7 show the processing method for initialization and normalization;

Series of FIG. 8 is the real-time system for monitoring the continuous blood sugar levels;

Series of FIG. 9 is the method of blood sugar analysis for recognizing the hypoglycaemia, hyperglycaemia and unusual blood sugar fluctuations;

FIG. 10 is the real-time system for monitoring continuous blood pressure levels;

Series of FIG. 11 is the method of blood pressure analysis for recognizing the hypertension, hypotension, and unusual blood pressure fluctuations;

FIG. 12 is the automated real-time system for monitoring emotional stress levels;

FIG. 13 is the real-time and automated sleep tracking system;

FIG. 14 shows a program for operating the telemetry apparatus using the buttons and navigator;

FIG. 15 is a learning method for estimating processing parameters from the user database;

FIG. 16 is the design of automated emergency response system;

FIG. 17 shows the network of devices based parallel computational and storage method;

FIG. 18 is the design of fancy LED apparatus;

Series of FIG. 19 show automated interface for recording user information and calibration values;

FIG. 20 is the automated interface for recording and accessing detailed diet information;

Series of FIG. 21 show the automated interface for accessing real-time biological information;

Series of FIG. 22 show the interface of the automated real-time alerting system;

Series of FIG. 23 show the real-time medication reminders;

Series of FIG. 24 show the sample interface of the automated recommendation system;

FIG. 25A and FIG. 25B show a single clipper based smart ring embodiment form of the telemetry apparatus;

FIG. 26 shows a dual clipper smart ring embodiment form of the telemetry apparatus;

FIG. 27A, FIG. 27B and FIG. 27C show the solar powered handheld monitoring embodiment form of the telemetry apparatus; and FIG. 28 is the ear attachment embodiment form of the telemetry apparatus.

DETAILED DESCRIPTION OF THE INVENTION

The principle of the described invention is not intended to limit to the specific device or instrumentation application. The disclosure can be chiefly classified into live clinical diagnostic instrument, telemetry medical apparatus, mobile wellness management device, automated recommendation system, real-time intelligent medical reminder, software medical device and other forms of health management devices.

Figure 1:
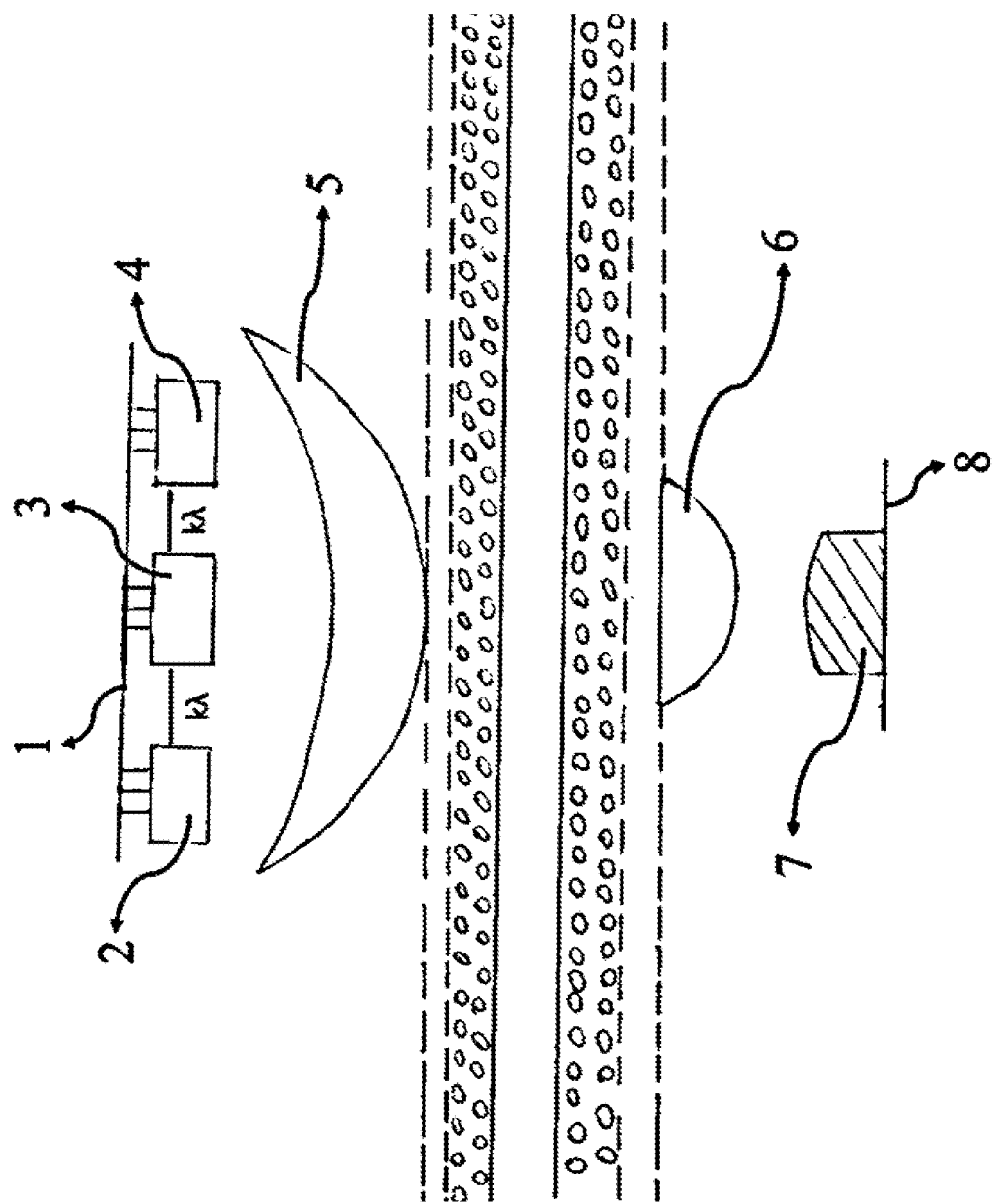
FIG. 1 is the transmittive near-infrared optical spectrometer apparatus.

FIG. 1 is the design of infrared spectrometer apparatus for transmittive sensing. The set Near-infrared light sources of 2-3-4 are embedded on the signal source board 1 at a quantum distance of $k\lambda$ between the light sources. The light emitted by the 2-3-4 are constructively focused by a near-infrared optical lens system 5 on the sensing spot. The quantum distance of wavelength number is maintained between the LDs and the light source objects to obtain a constructive interference (i.e. the distance can vary depending on the relative angle between the light sources or any coherent sources such as slits, etc). The transmitted optical response is focused by the near-infrared optical lens system 6 on the near-infrared photodetector 7 placed on the photodetector board 8. The set of lens system of 5-6 are used to facilitate the transmission of near-infrared through the sensing spot, which would be otherwise lost due to lossy nature of the near-infrared radiations.

Figure 2:
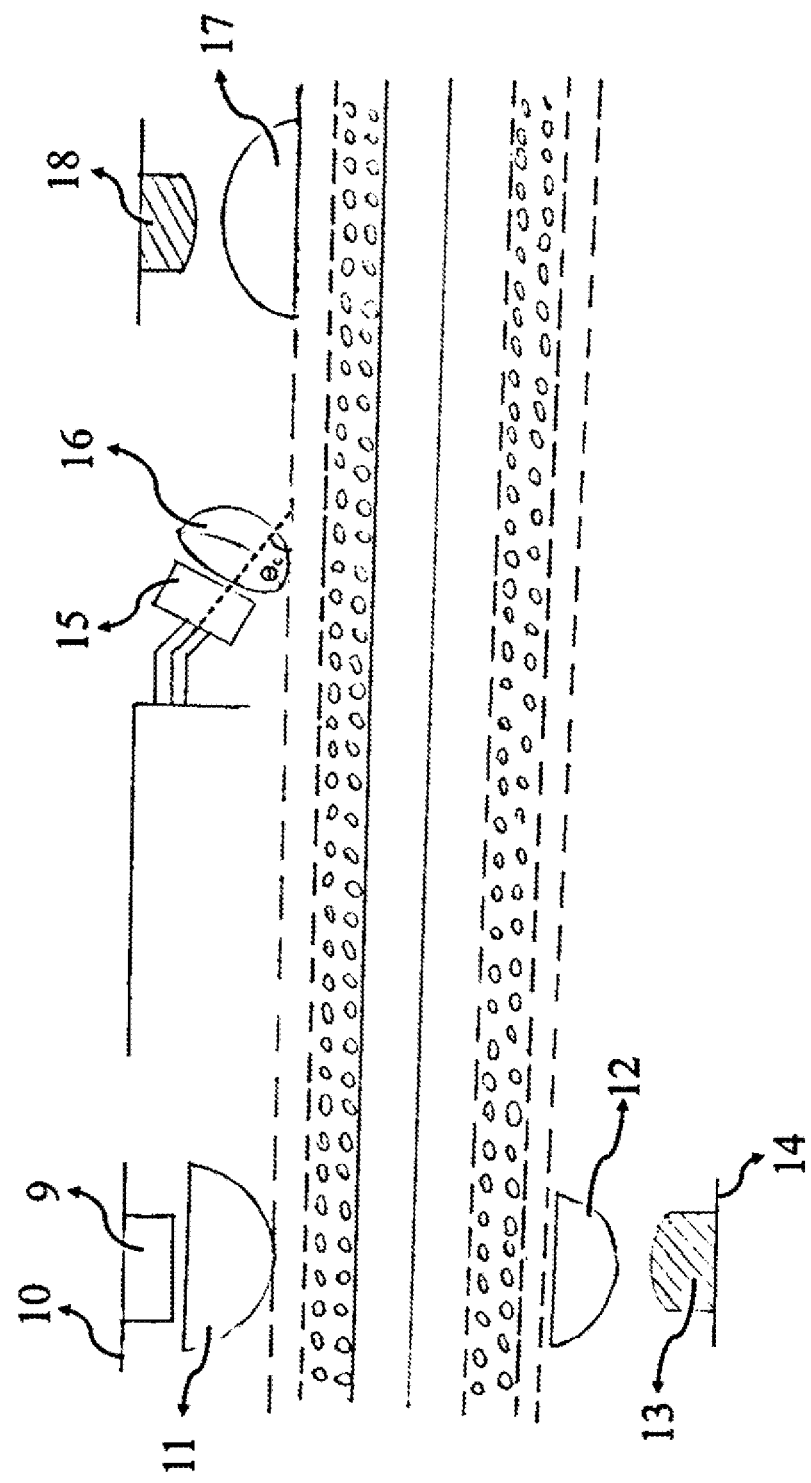
FIG. 2 is the green optical spectrometer apparatus.

FIG. 2 shows the green optical spectrometer apparatus. The apparatus comprises of both the transmittive and reflective arrangement to precisely extract the green response and the relevant physiological parameters. The transmittive green spectrometer apparatus comprises of green LED signal probe 9 embedded on the signal probe board 10. The light emitted by the green light source 9 is captured and focused by the signal probe end green optical lens system 11. The transmitted green optical response is concentrated and focused by the optical lens system 12 on the green photodetector 13 placed on the green photodetector board 14. The reflective green spectrometer comprises set of green LED 15 and green optical lens system 16 at signal probe end, which are tilted at $\theta_c$ angles. The input light signal injected by the green LED 15 and the optical lens system 16 at the critical angle bounces from the skin boundary. The reflected response is captured and focused by the optical lens 17 on the green photodetector 18, which are embedded at an optimal noise-free response recording spot.

Figure 3:
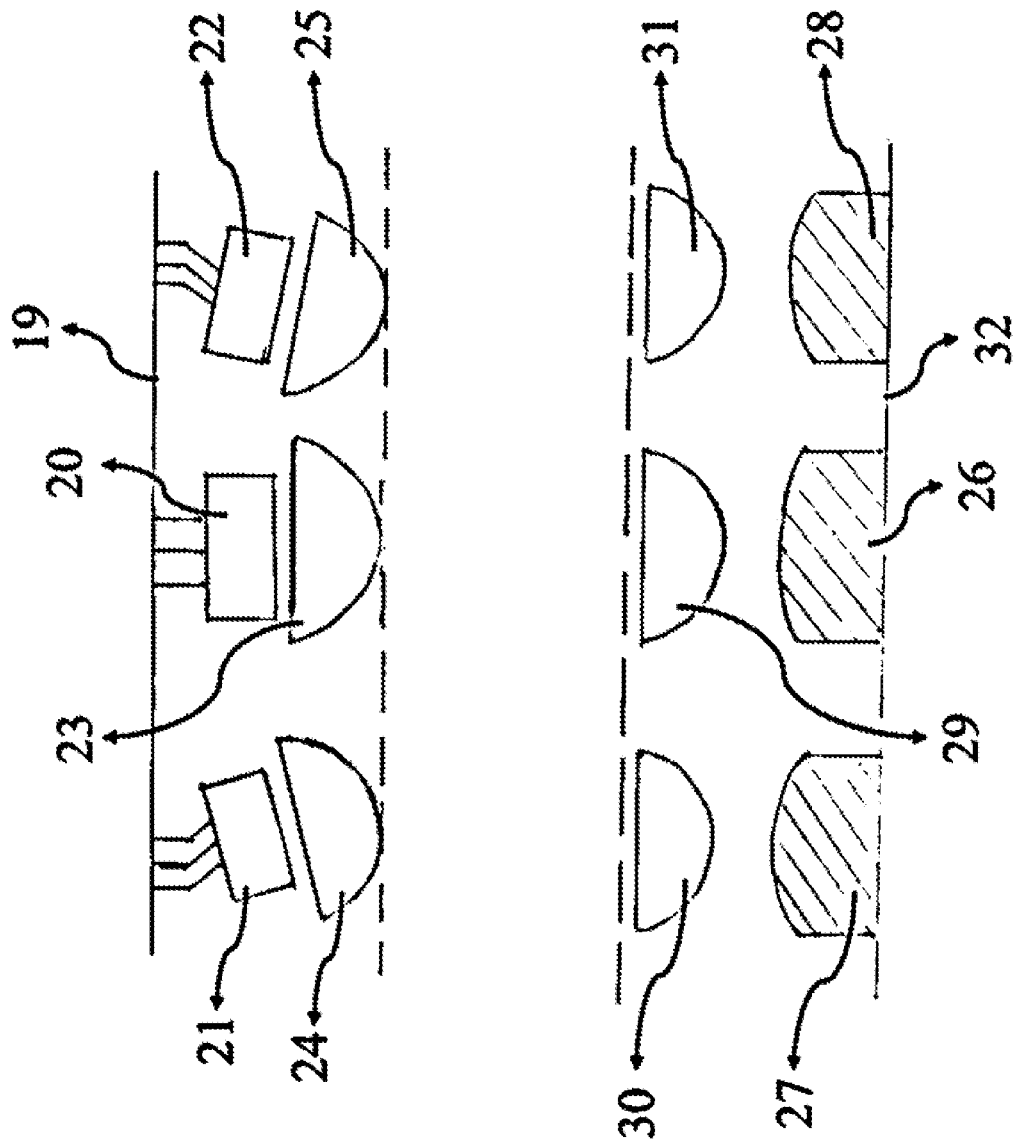
FIG. 3 is the transmittive red optical spectrometer apparatus.

FIG. 3 shows the red indicator apparatus for transmittive red dispersion analysis. The apparatus comprises of three red LED signal probes 20-21-22 embedded on the LED signal probe board 19 and their corresponding red optical system of 23-24-25 are aligned in different directions. The central red LED signal probe 20 and its red optical lens system 23 are placed in the normal direction with its input focus on the central photodetection spot. The non-central red LED signal probes 21-22 and their corresponding red optical lens system 24-25 are embedded on the adjacent positions to the normal red signal probe system 20-23. The adjacent red LED 21 and its optical lens system 24, embedded on the left-side, are tilted to focus the input signal on the central photodetection spot. The non-central red LED 22 and its optical lens system 25, embedded on the right-side, are tilted to focus the input light on the central photodetection spot. The central photodetector of 26 and non-central photodetectors of 27-28 are embedded on the photodetector board 32 at different response recording spots. The central red photodetector 26 and its red optical lens system 29 are placed at the central response receiving position. The non-central red photodetector 27 and its red optical lens system 30 are placed on the adjacent left position to the central red photodetector 26 for recording the dispersion signals. The non-central red photodetector 28 and its red optical lens system 31 are placed on the adjacent right position to the central red photodetector 26 for recording the dispersion signals.

Figure 4:
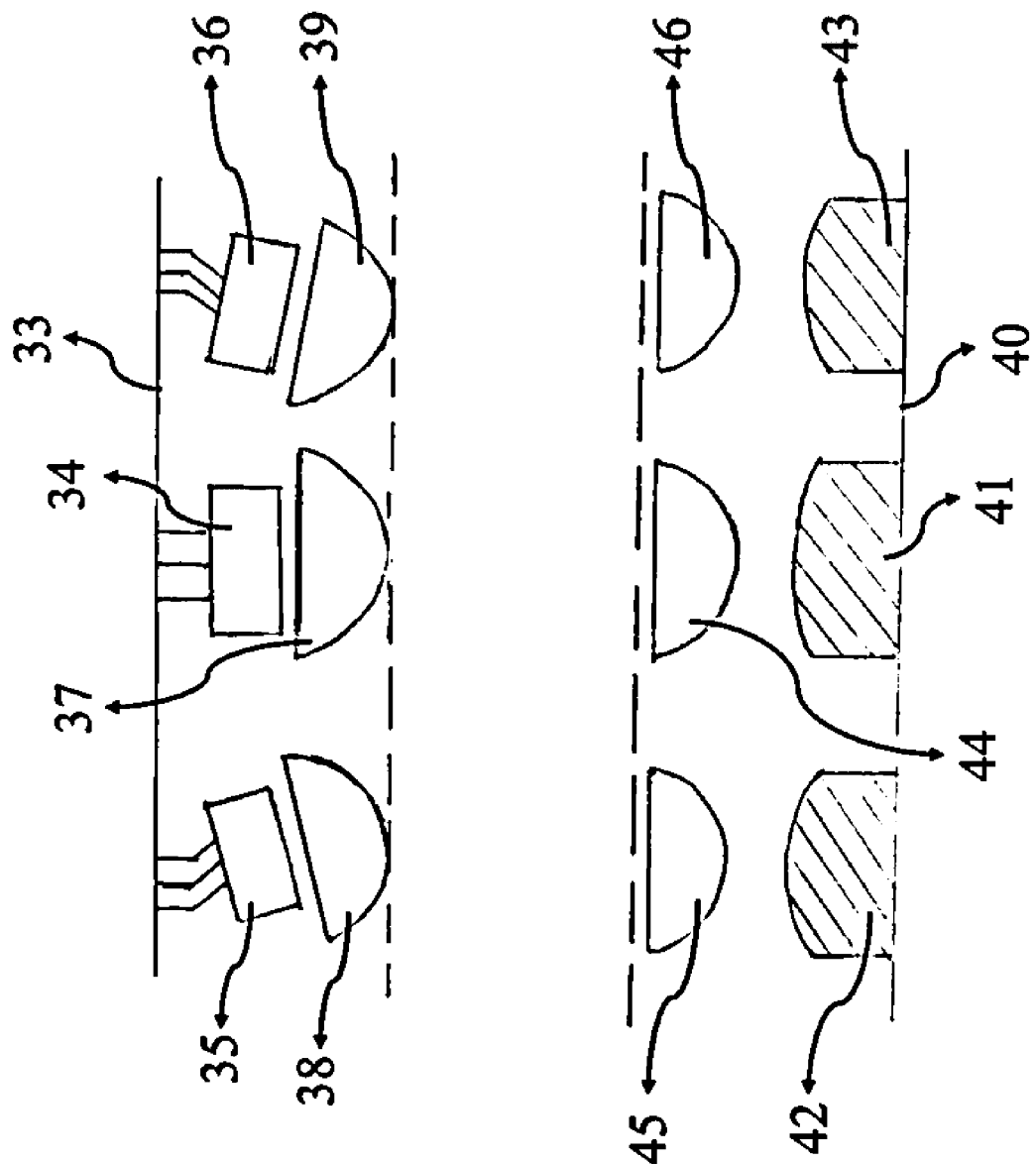
FIG. 4 is the transmittive infrared optical spectrometer apparatus.

FIG. 4 shows the infrared indicator apparatus for transmittive infrared dispersion analysis. The apparatus comprises of three infrared LED signal probes 34-35-36 embedded on the signal probe board 33 and their corresponding infrared optical system of 37-38-39 are aligned in different directions. The central infrared LED signal probe 34 and its infrared optical lens system 37 are placed in the normal direction with its input focus on the central photodetection spot. The non-central infrared LED signal probes 35-36 and their corresponding infrared optical lens system 38-39 are embedded on the adjacent positions to the normal infrared signal probe system 34-37. The adjacent infrared LED 35 and its optical lens system 38, embedded on the left-side, are tilted to focus the input signal on the central photodetection spot. The non-central infrared LED 36 and its optical lens system 39, embedded on the right-side, are tilted to focus the input light on the central photodetection spot. The central photodetector of 41 and non-central photodetectors of 42-43 are embedded on the photodetector board 40 at different response recording spots. The central infrared photodetector 41 and its infrared optical lens system 44 are placed at the central response receiving position. The non-central infrared photodetector 42 and its infrared optical lens system 45 are placed on the adjacent left position to the central infrared photodetector 41 for recording the dispersion signals. The non-central infrared photodetector 43 and its infrared optical lens system 46 are placed on the adjacent right position to the central infrared photodetector 41 for recording the dispersion signals. Similarly, light sources of different spectrum can be utilized for evaluating the real-time biological information and spectral dispersion data.

Figure 5A:
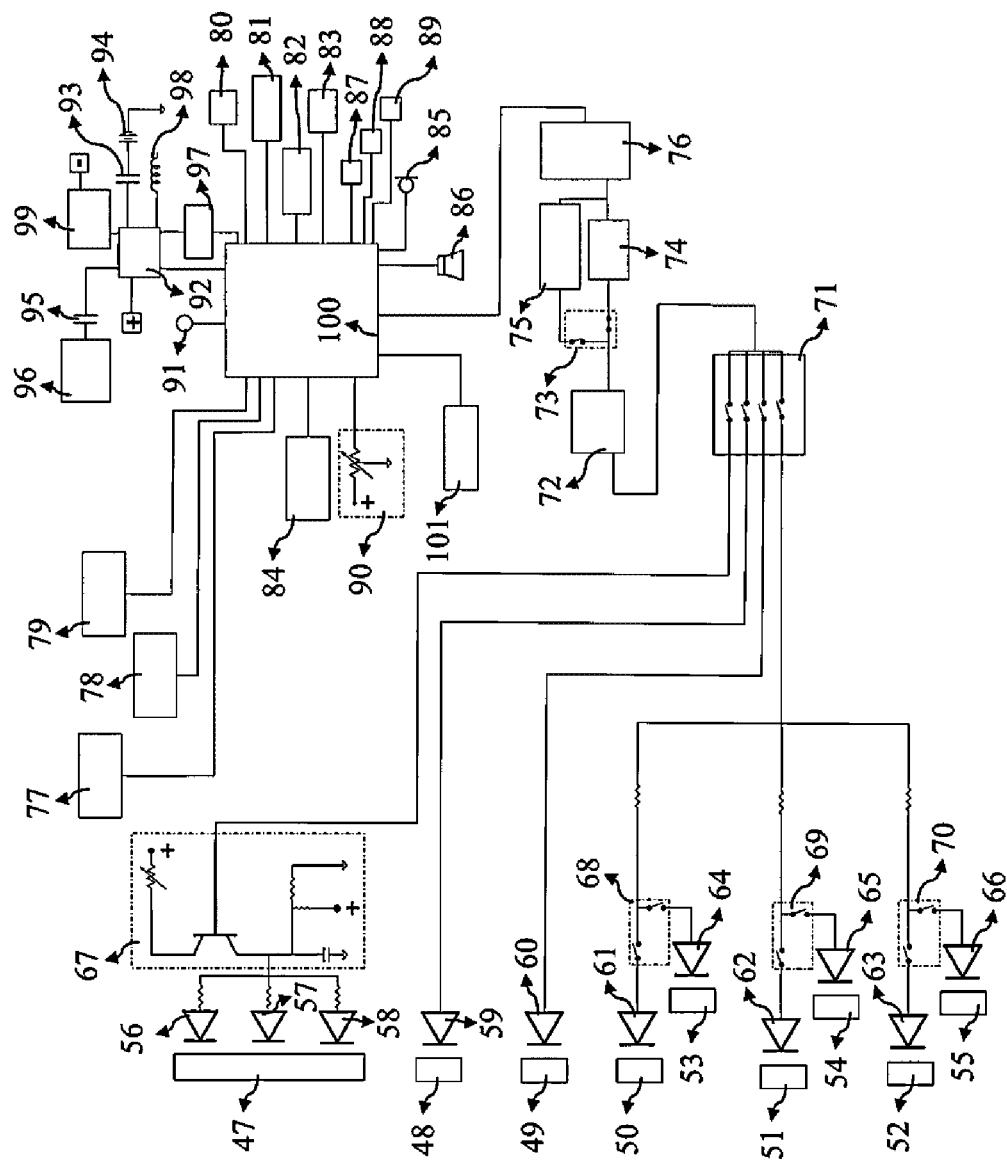
FIG. 5A shows the low powered electronic hardware design of the telemetry at the signal probe end.
Figure 5B:
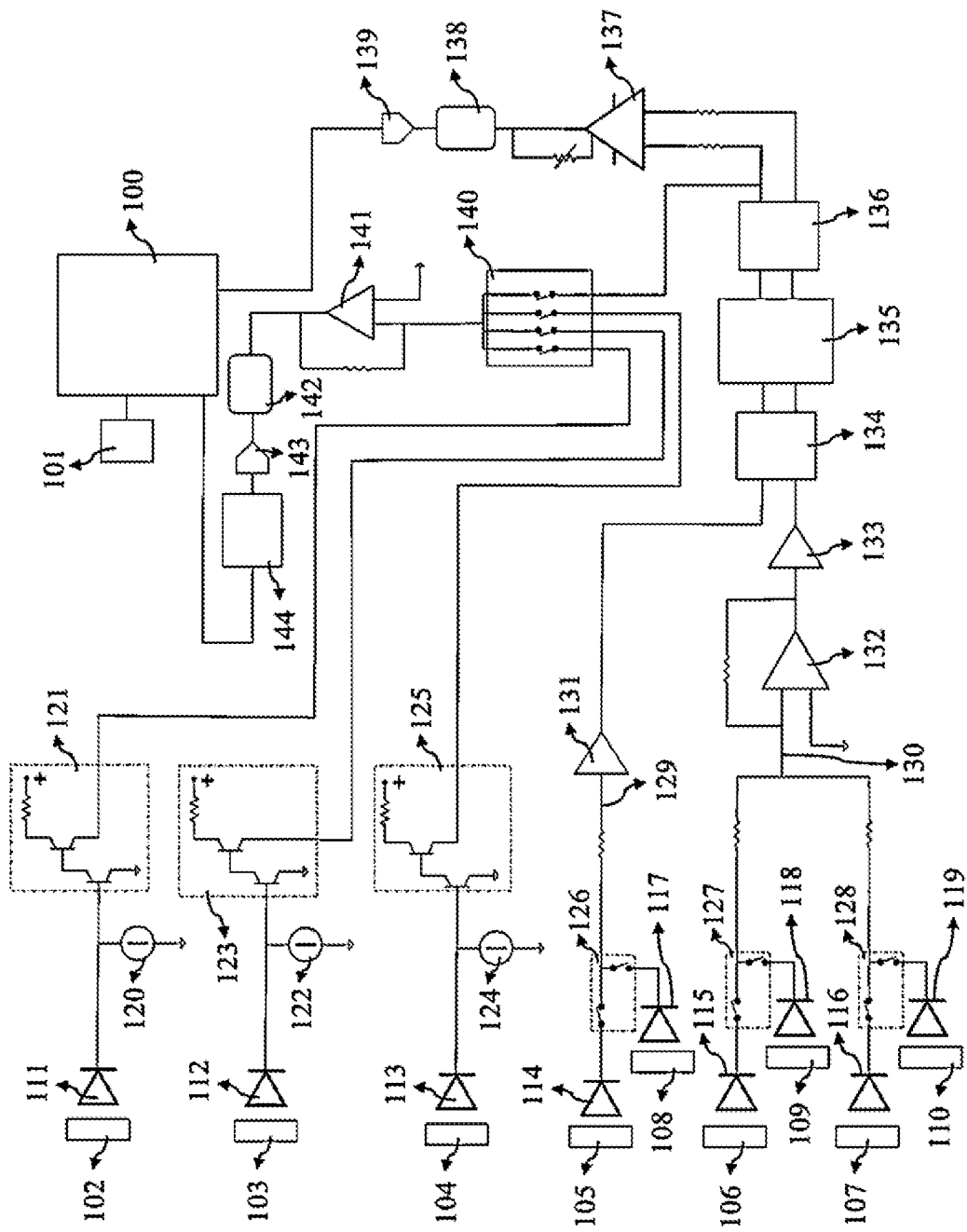
FIG. 5B shows the low powered electronic hardware design of the telemetry at the photodetector end.

FIG. 5A and FIG. 5B show the electronic hardware architecture of the telemetry to implement the spectrometer apparatuses.

FIG. 5A shows the signal probe end hardware design with micro-sensors, wireless antennae, user interaction system and power supply unit. The input to the near-infrared light sources of 56, 57 and 58 are coherently driven through a resistor line and a tuneable FET/BIT based active amplifier circuit 67. A set of switches 68-69-70 are placed between the corresponding red LED-infrared LED set of 61-64, 62-65 and 63-66, which are utilized to alternatively drive input to the red LED signal probes of 61-62-63 and infrared LED signal probes of 64-65-66. The signal input is variably triggered and sent through a LED frontend comprising of LED driver 72, PWM 74, switch set 73, LED controller 75 and clock controller 76. A signal probe end primary switch set 71 is utilized for connecting the LED frontend of 72-73-74-75-76 to the red-infrared signal input line, Green LED 59, tilted Green LED 60, and active amplifier circuit 67 attached to the near-infrared LDs 56-57-58. The primary switch set 71 reduces the overall component use, power consumption and electrical tracing efforts. The optical lens system of 47, 48, 49, 50, 51, 52, 53, 54 and 55 tunes and focuses the input radiation of corresponding light sources of 56-57-58, 59, 60, 61, 62, 63, 64, 65 and 66 on the sensing spot.

A MEMs/NEMs non-contact temperature biosensor 77 is attached to the hardware for extracting the real-time body temperature and temperature feedback. An ambient temperature sensor 78 of the hardware is utilized for extracting real-time environment temperature and feedback of the internal electronics. A MEMs/NEMs 9/6-axis accelerometer 79 is attached to the hardware, which is utilized as real-time motion feedback and as a means to compute movement signals. The wireless antennae set of GPS 80, GSM 83, WLAN 81 and BLE 82 of the hardware are used for communicating the information between the telemetry apparatus and external devices. The wireless antenna set of 80-81-82-83 is also utilized to compute the real-time location and movement data of steps taken, speed, phase, etc. The microprocessor 100 attached to memory 101, is used for communicating with the internal electronics and operating the internal electronic components. The microprocessor 100 with memory 101 is also utilized for computing and storing the required information.

A mini touch display 84 is attached to the hardware, which is utilized for viewing and accessing the real-time medical information, real-time medical alerts, automated recommendations, notifications, data trends, daily health check-up data and other essential information. The touch display 84 is also used for operating the telemetry apparatus and its in-built applications. Apart from the display unit 84, the hardware of the telemetry device is attached to a user interaction system of mic 85, speaker 86, button set B1-B2-B3 87-88-89 and potentiometer integrated navigator 90. The navigator crown 90 comprises of a potentiometer and a fixed impedance component. The set of interaction components of 85-87-88-89-90 are utilized for operating the telemetry apparatus and accessing the in-built applications. The set of user interaction hardware components of 85-86-87-88-89-90 are utilized as a means for interacting with the professional medical and health practitioners for clinical and health analysis. The speaker 86 is also used for perceiving the recorded and computed information. A fancy LED circuit 91 is attached to the hardware, which is utilized for automatically indicating the user condition, displaying decorative applications and representing different operating modes and device status.

The hardware of the telemetry apparatus is powered by a power supply unit comprising of power management IC 92, supercapacitor 93-battery set 94, supercapacitor 95-renewable energy harvester 96, wireless coil 98, USB module 97 and negative voltage converter 99. The power management IC 92 is used to regulate power supply. The supercapacitor 93-battery 94 is utilized for energy storage and powering the internal electronics. The supercapacitor 95-renewable energy harvester 96 is used as the auxiliary powering unit. The wireless coil 98 is used as the wireless method to charge the battery and power the internal electronics. The negative signal reference is generated by the negative voltage converter 99. The USB module 97 is used for powering the electronic circuit, charging the internal battery and communicating the data with the external devices.

FIG. 5B shows the photodetector probe end hardware design of the telemetry apparatus. The output response is focused by optical lens system of 102, 103, 104, 105, 106, 107, 108, 109 and 110 on the corresponding photodetector probes of 111, 112, 113, 114, 115, 116, 117, 118 and 119. The near-infrared output response recorded by the near-infrared photodetector probe 111 is shifted by small signal source 120 and amplified by the darlington pair 121. The transmittive green response recorded by the green photodetector probe of 112 is shifted by small signal source 122 and amplified by the darlington pair 123. The reflected green response recorded by the green photodetector probe of 113 is shifted by small signal source 124 and amplified by the darlington pair 125. A set of switches of 126, 127 and 128 are placed between the corresponding set of red photodetector-infrared photodetector of 114-117, 115-118 and 116-119. The set of switches of 126, 127 and 128 are utilized to alternatively record output response of the red photodetector probes of 114-115-116 and infrared photodetector probes of 117-118-119.

The response of red-infrared photodetectors set are taken through the output lines of central response line 129 and summed non-central response line 130. An op-amp IC 132 is utilized to sum the output response of the non-central photodetectors. The output line of central photodetector and non-central photodetectors are stabilized through a buffer circuit of 131 and 133. The summed non-central photodetector response and central photodetector responses are filtered and processed using a circuit line of ADC 134, ambient noise cancellation IC 135 and DAC 136. An Instrumental amplifier 137 with gain is attached to the output line of non-central photodetector response line and central photodetector line for extracting the real-time dispersion information. The real-time dispersion is further filtered and recorded through a circuit line of power notch 138 and ADC 139. The processed output response lines of the individual light sources are attached to the transimpedance amplifier circuit or op-amp circuit 141 through a photodetector end primary switch set 140. The photodetector end primary switch set 140 is utilized as a means to reduce the component use and overall power consumption. The output response through op-amp circuit 141 is filtered and processed through a circuit line of power notch 142, ADC 143 and ambient noise cancellation IC 144.

Figure 6A:
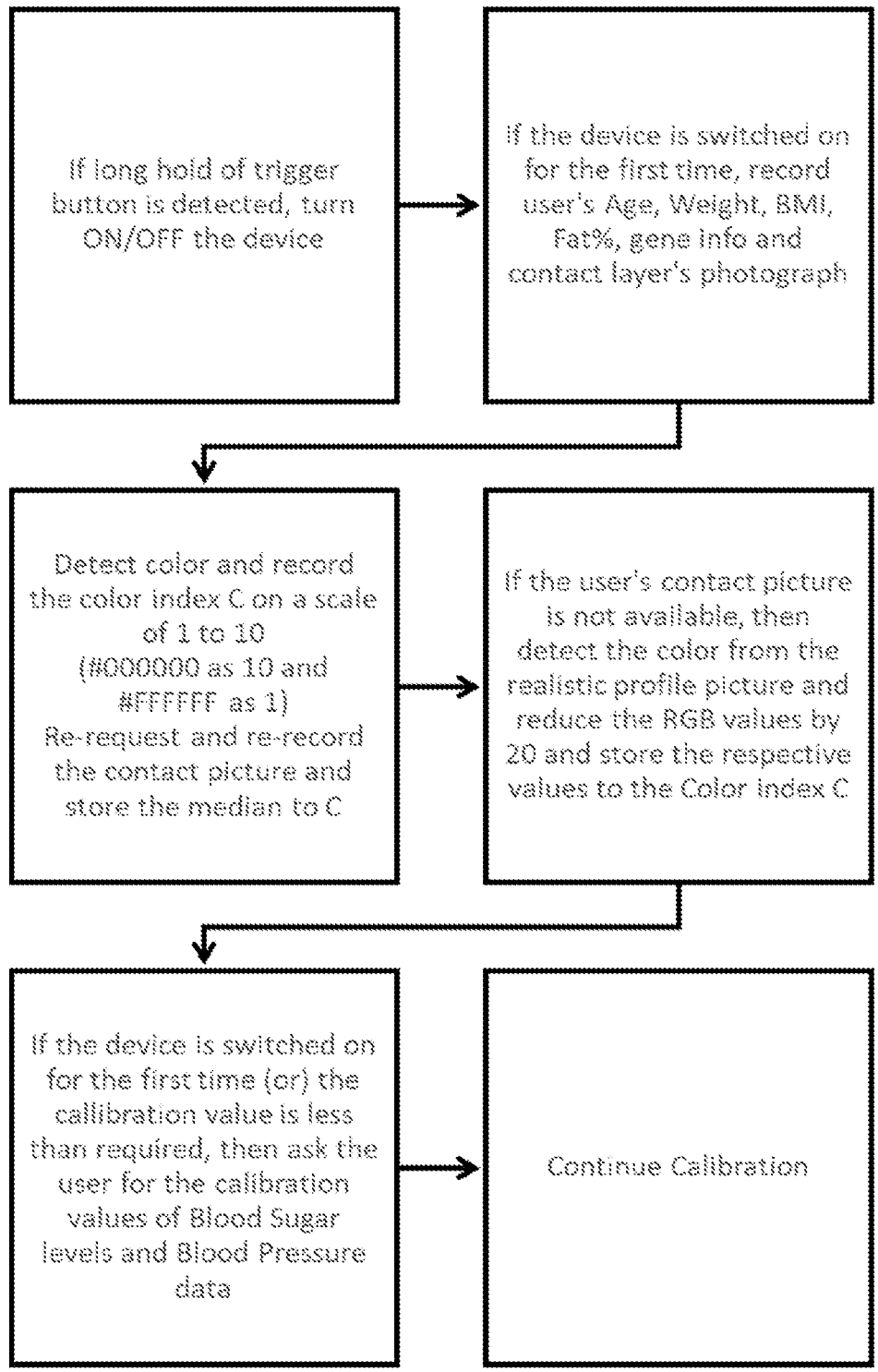
Figure 6B:
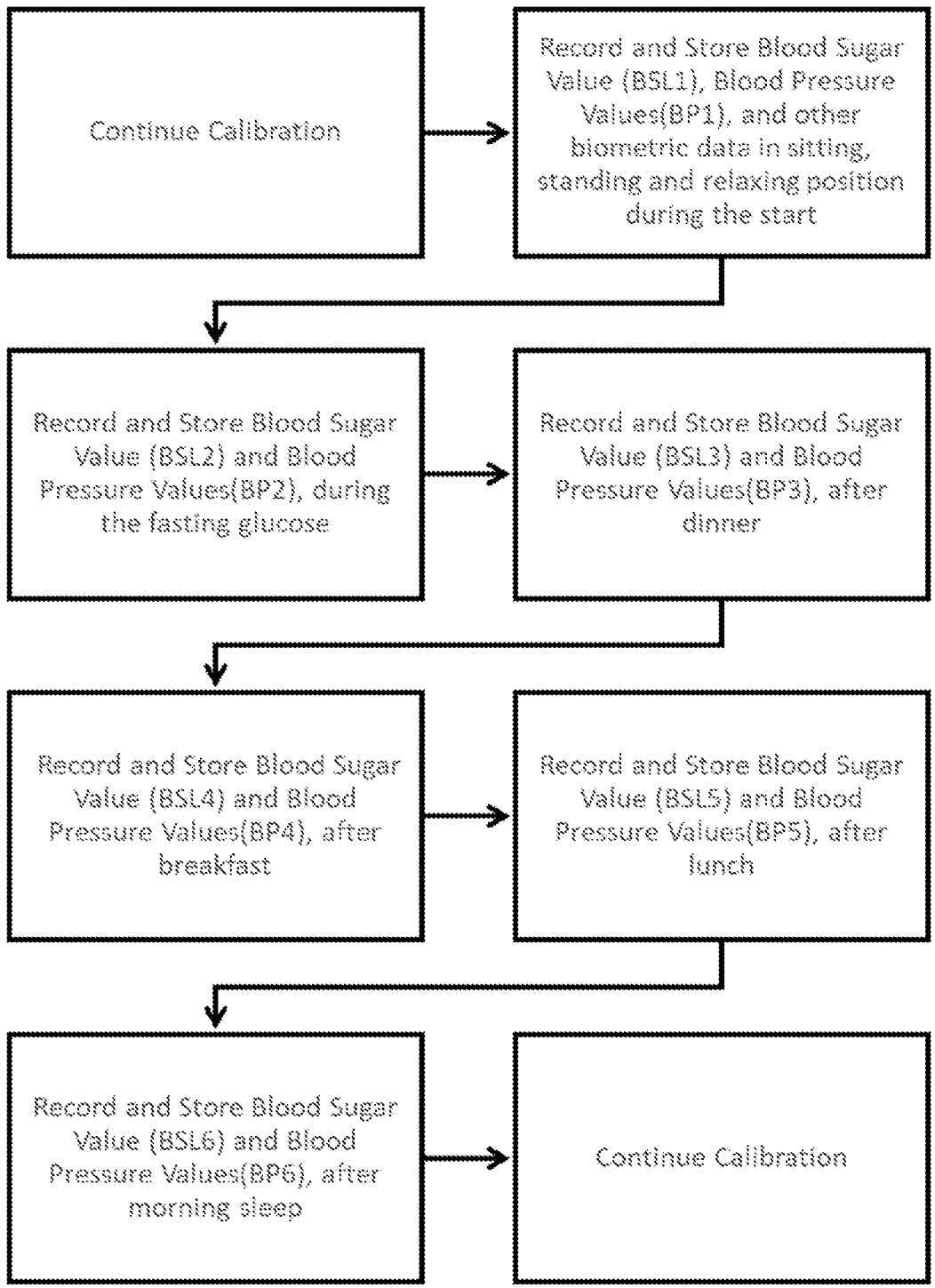
Figure 6C:
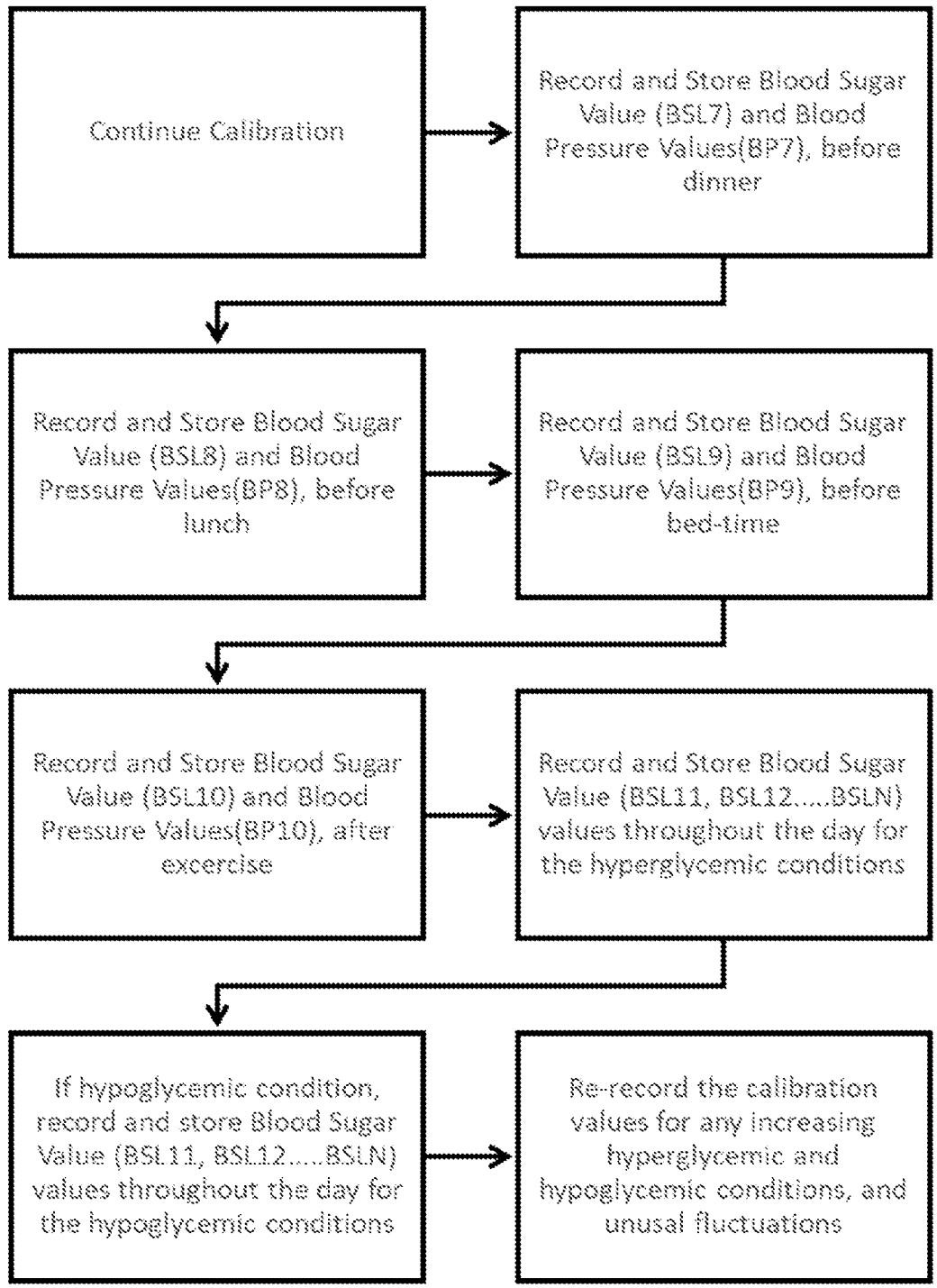

FIG. 6A, FIG. 6B and FIG. 6C show the method to calibrate the telemetry device. The user information of age, weight, BMI, fat %, gene info and contact layer's photograph are recorded during the initial device start-up. The recorded contact skin picture is analysed in the RGB hex code and deduced on a scale of 1 to 10. The device prompts the user to re-record the contact picture multiple times and the recorded contact skin picture is analysed to deduce the color of the contact surface. On unavailability of the contact surface picture, the realistic profile picture of the user is recognized, and the profile picture values are altered by an adjusting parameter to extract the contact layer skin color values. The blood sugar levels, blood pressure data and other real-time biological information of the user are recorded during the sitting position, standing position, relaxing position, fasting glucose, post-dinner, post-breakfast, post-lunch, post-morning sleep, post-exercise, pre-dinner, pre-breakfast, pre-lunch, before bed-time, hypoglycaemic state and hyperglycaemic state. The device prompts the user to re-record the blood sugar data, blood pressure levels and other real-time biological information for unusual fluctuations and increasing hyperglycaemic and hypoglycaemic conditions.

Figure 7A:
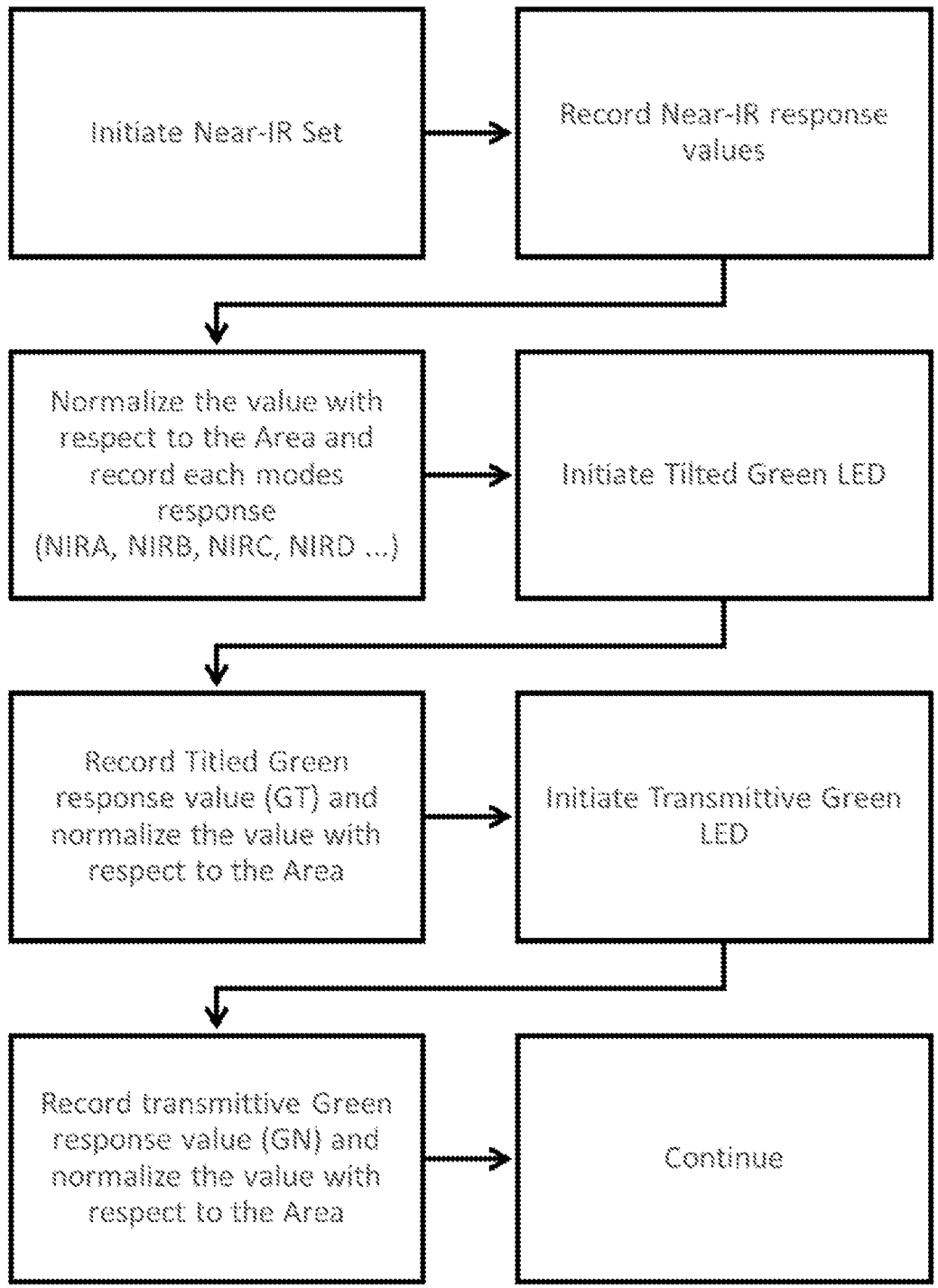
Figure 7B:
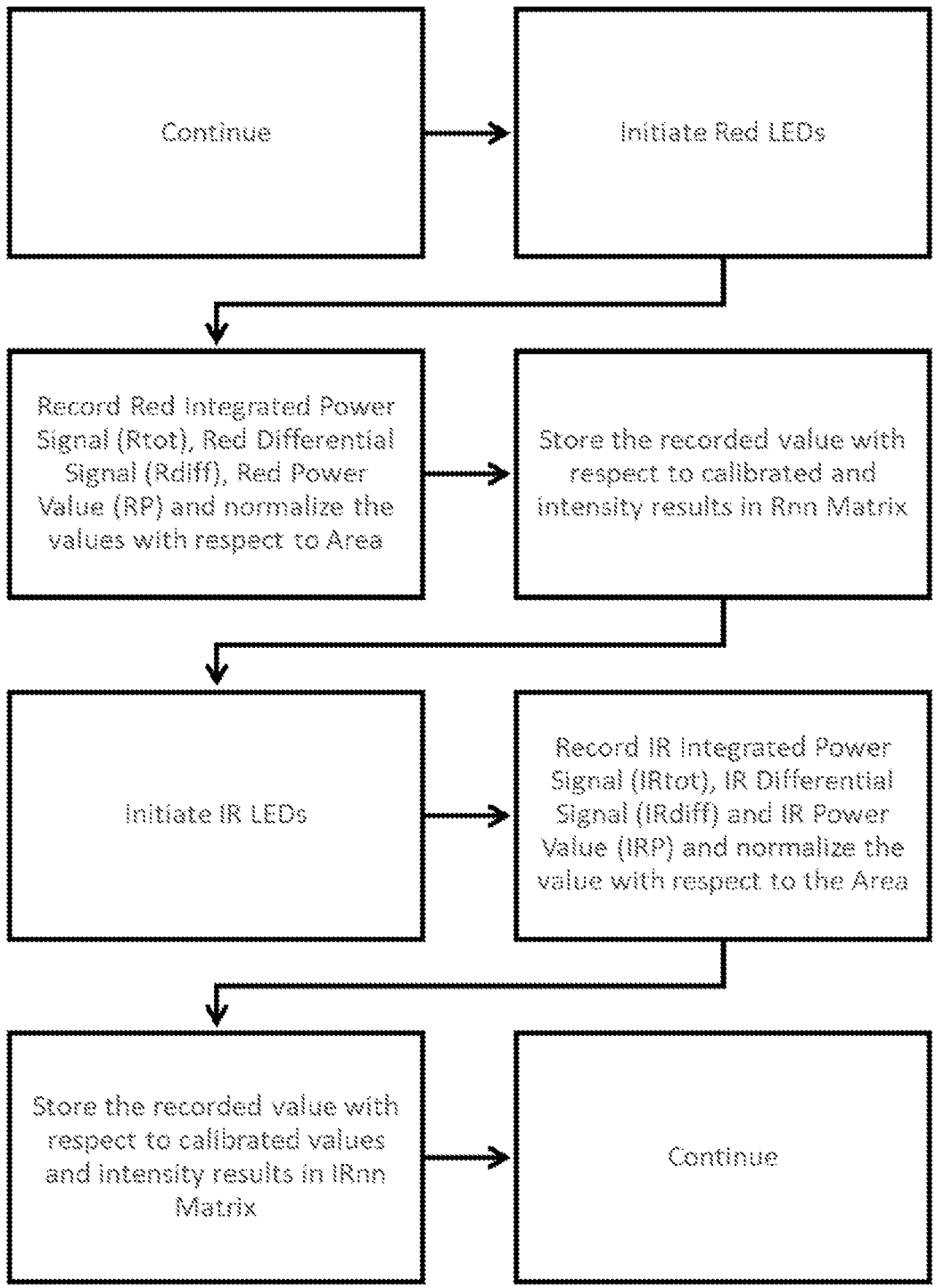
Figure 7C:
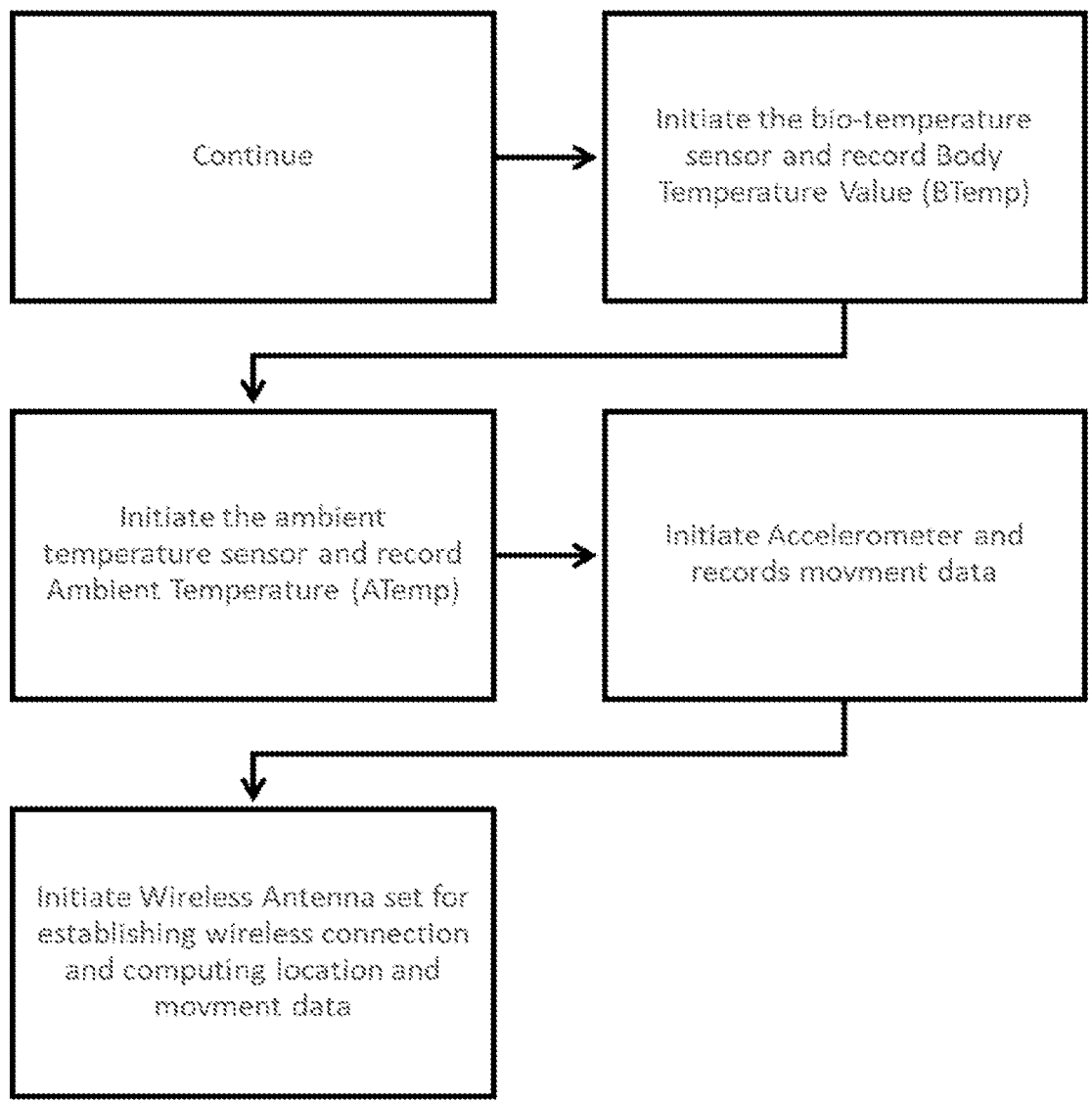

FIG. 7A, FIG. 7B and FIG. 7C show the process chart for sensor initialization and sensor response normalization. The near-infrared LDs, tilted green LED, transmittive green LED, red LEDs, infrared LEDs and biosensors are initialized in a cyclic manner. The near-infrared response of different modes are recorded and normalized with respect to the area (NIRA, NIRB, NIRC, NIRD and so till NIRN). The tilted green response and transmittive green response are recorded and normalized with respect to the area (GT and GN). The red response values of red Integrated Power Signal (Rtot), red Differential Signal (Rdiff) and Red Power Value (RP) are recorded and normalized with respect to the area. The values of the red signal response are stored with respect to calibrated values in the Rnn Matrix. The infrared response values of IR Integrated Power Signal (IRtot), IR Differential Signal (IRdiff) and IR Power Value (IRP) are recorded and normalized with respect to the area. The values of the infrared signal response are stored with respect to calibrated values in the IRnn Matrix. The system initializes the bio-temperature sensor and ambient temperature sensor for recording the real-time bio-temperature values (Btemp) and ambient temperature values (Atemp). The accelerometer and wireless antennae are initialized for recording the movement data, location data and establishing wireless communication.

Figure 8A:
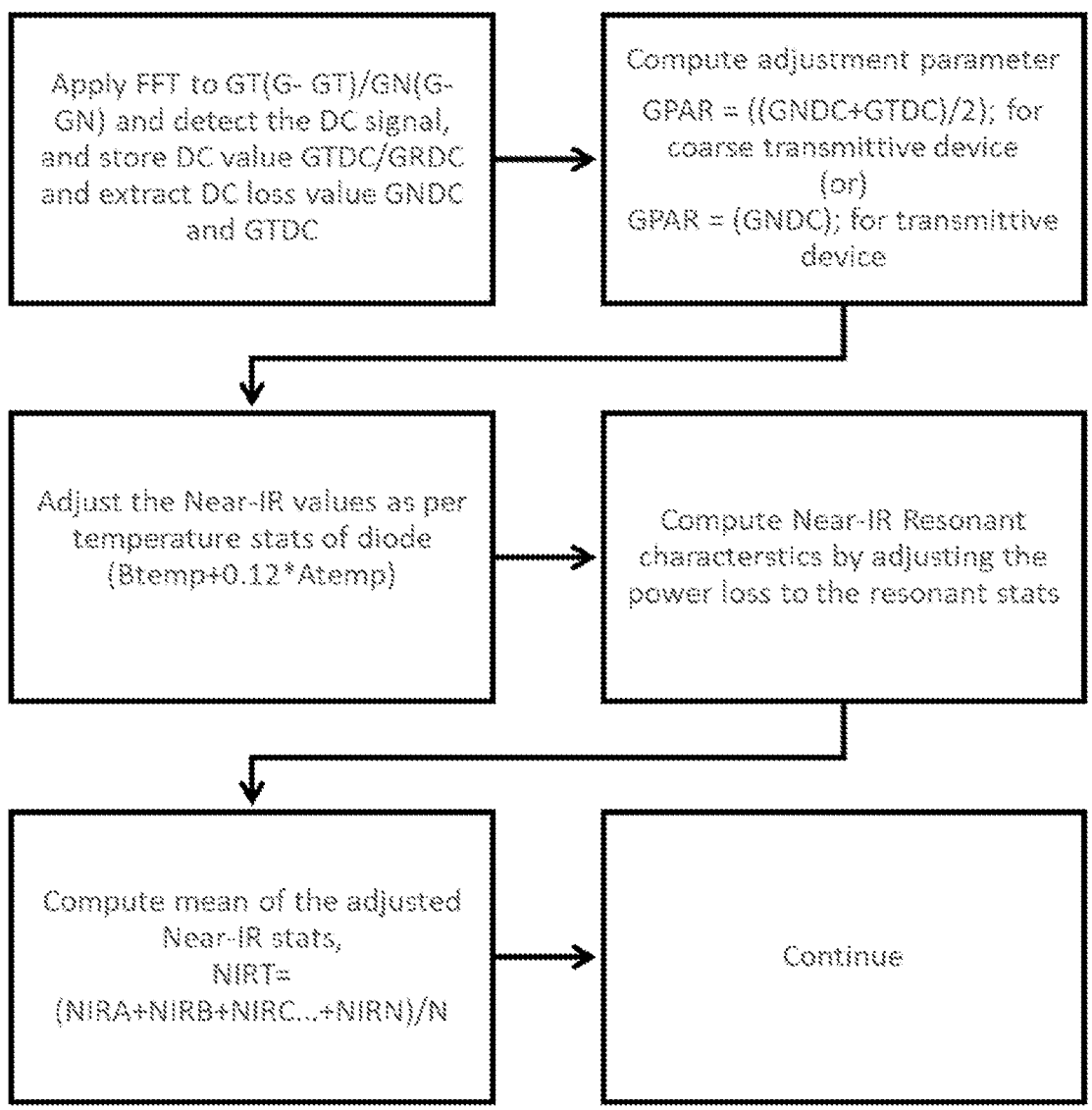
Figure 8B:
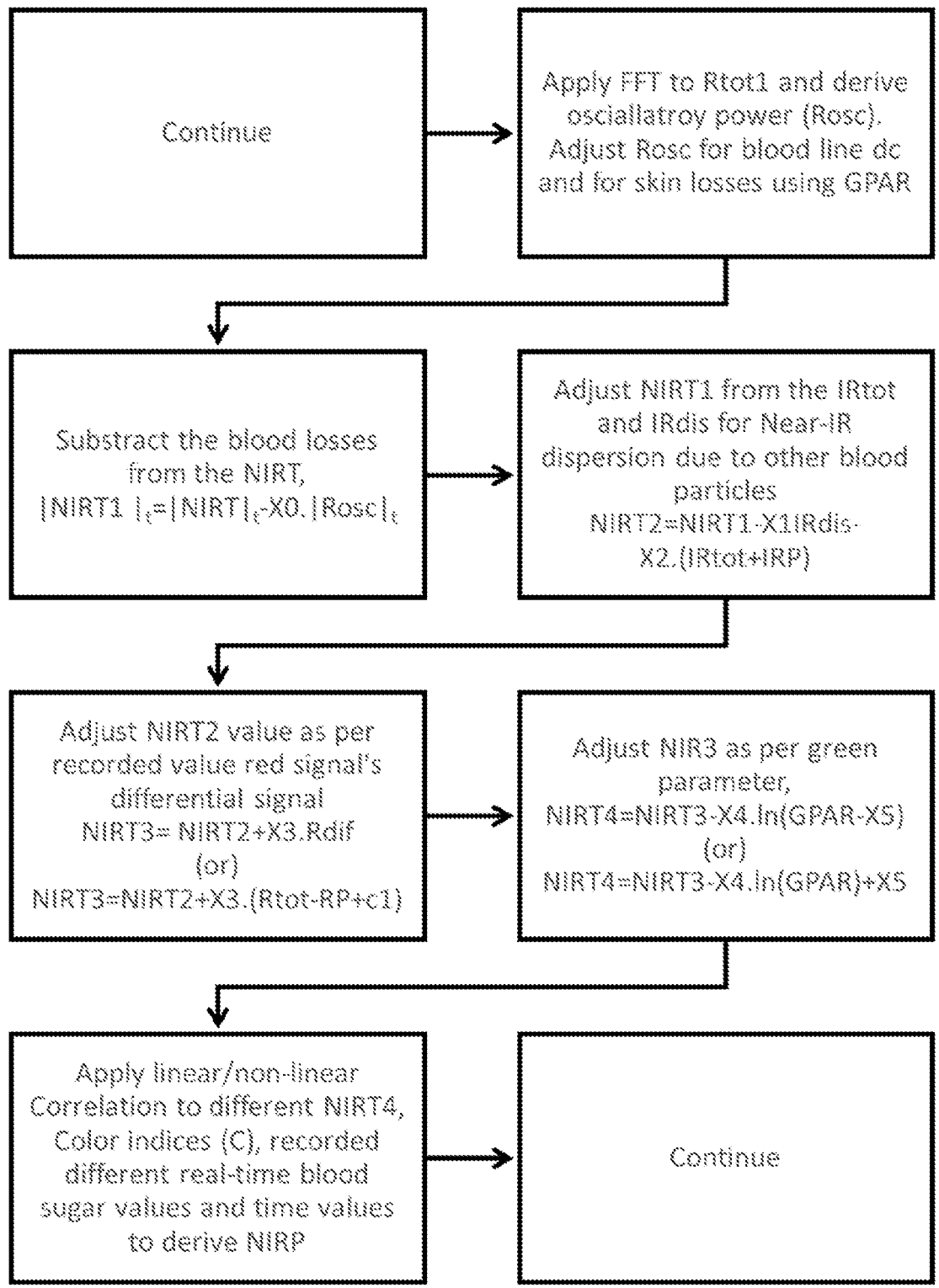
Figure 8C:
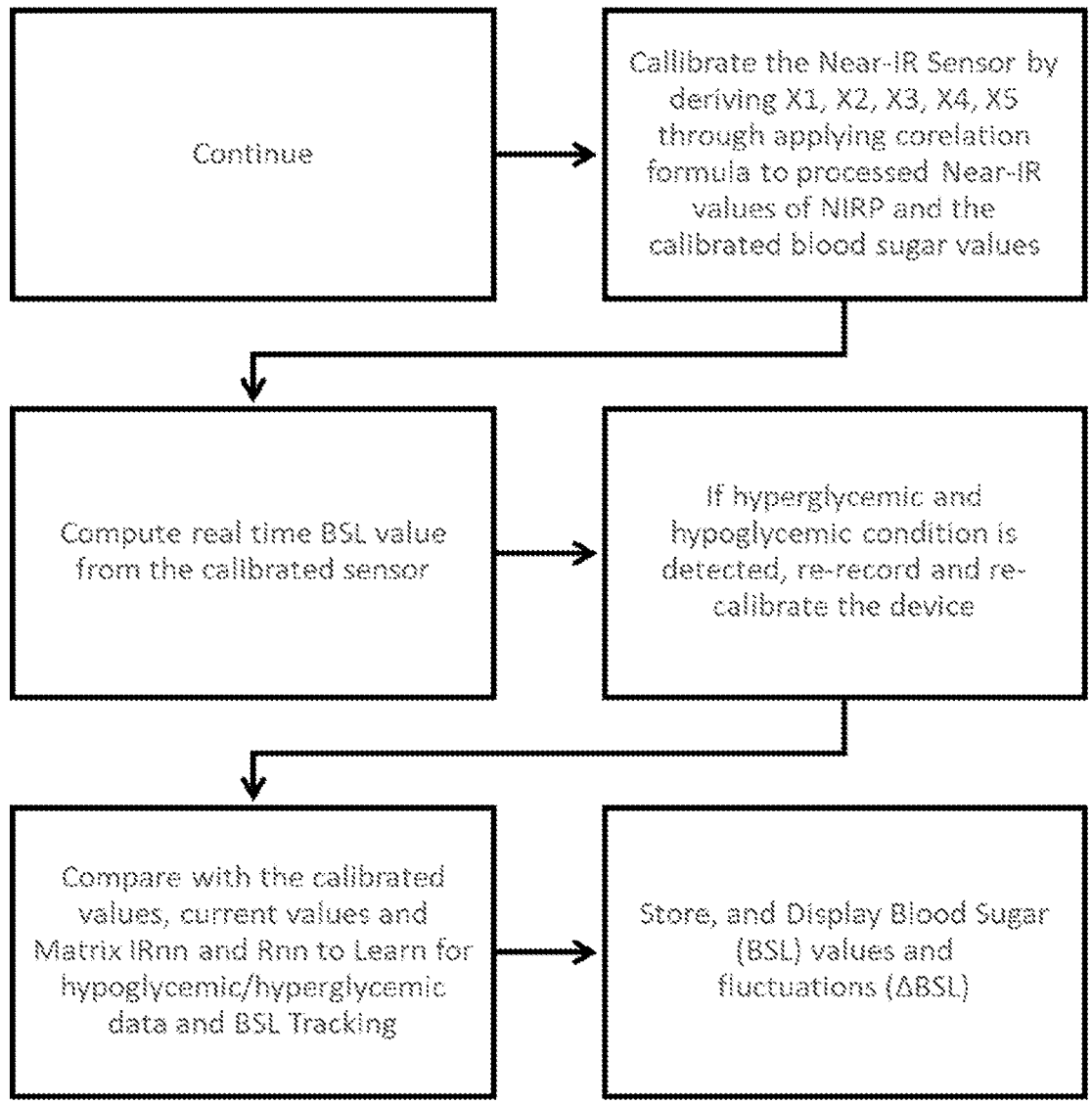

FIG. 8A, FIG. 8B and FIG. 8C show the real-time system for monitoring the continuous blood sugar levels. The recorded green sensor response of GT and GN are analyzed to recognize the green sensor DC parameter losses (GTDC and GNDC). The green parameter (GPAR) is deduced from green sensor DC parameter based on the type of the contact surface (GPAR=((GNDC+GTDC)/2); for coarse transmittive device (or) GPAR=GNDC; for transmittive device). The recorded near-infrared response values are adjusted as per the temperature stats of the bio-temperature and ambient temperature response and the mean of the adjusted near-infrared modes (NIRT) is deduced (NIRT=(NIRA +NIRB+ NIRC + so on till NIRN)/N). The real-time system processes the recorded red signal to deduce oscillatory red signal values (Rosc) and the oscillatory red response values (Rosc) are adjusted for skin losses using the green parameter (GPAR). The blood line losses free $1^{st}$ order near-infrared sensor value (NIRT1) is extracted from the oscillatory red response (Rosc) and normalized near-infrared response (NIRT) using linear and non-linear analysis method ($|NIRT1|_t=|NIRT|_t-X0.|Rosc|_t$). The first order near-infrared (NIRT1) is processed with the infrared response (of IRtot and IRdis) for adjusting the near-infrared response for non-haemoglobin particle and other blood particle losses (NIRT2=NIRT1−X1IRdis−X2.(IRtot+IRP)). The $2^{nd}$ order near-infrared response (NIRT2) response is further linearly or non-linearly correlated with the red differential value (Rdiff) for extracting the $3^{rd}$ order near-infrared response (NIRT3=NIRT2+X3.Rdif). The extracted $3^{rd}$ order near-infrared response (NIRT3) is analyzed with green parameter (GPAR) in the equation form of either power exponent or linear representation of unknown intercept and unknown coefficient for extracting the $4^{th}$ order near-infrared response (NIRT4=NIRT3−X4.ln(GPAR−5) (or) NIRT4=NIRT3−X4.ln(GPAR)+X5). The processed near-infrared response is adjusted for recorded color index C and real-time blood sugar values using non-linear and linear correlation. The processed near-infrared response is correlated with the recorded blood sugar calibration values utilizing non-linear and linear correlation for computing the real-time continuous blood sugar values. The real-time blood sugar values (BSL) and blood sugar fluctuations (ΔBSL) are stored and displayed. The real-time BSL values are further learnt with respect to the calibrated values, red response and infrared response for recognizing hypoglycemic and hyperglycemic data and blood sugar levels. The real-time system records additional calibration values for recognized conditions of hypoglycaemia, hyperglycemia and unusual blood sugar fluctuations.

Figure 9A:
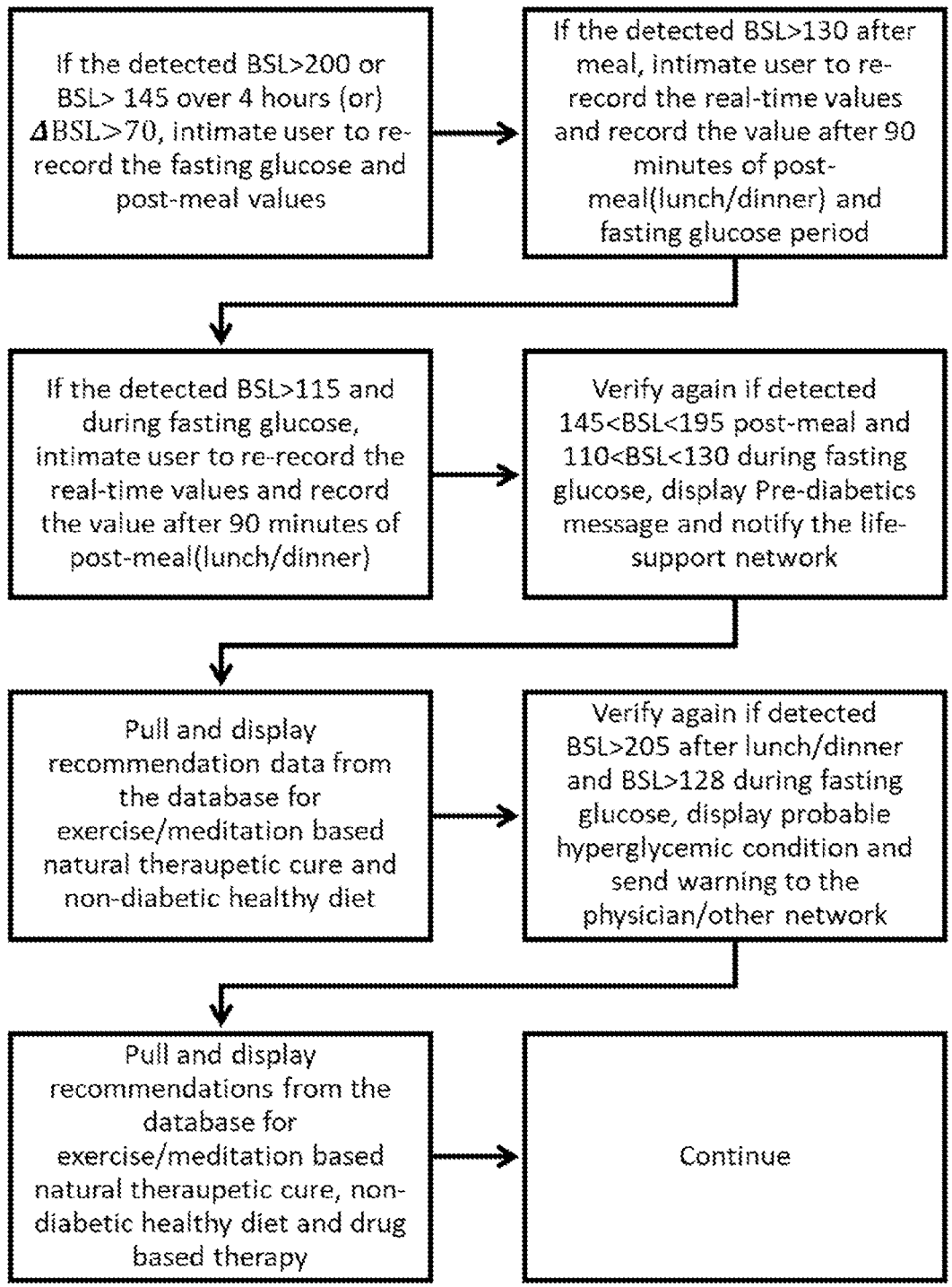
Figure 9B:
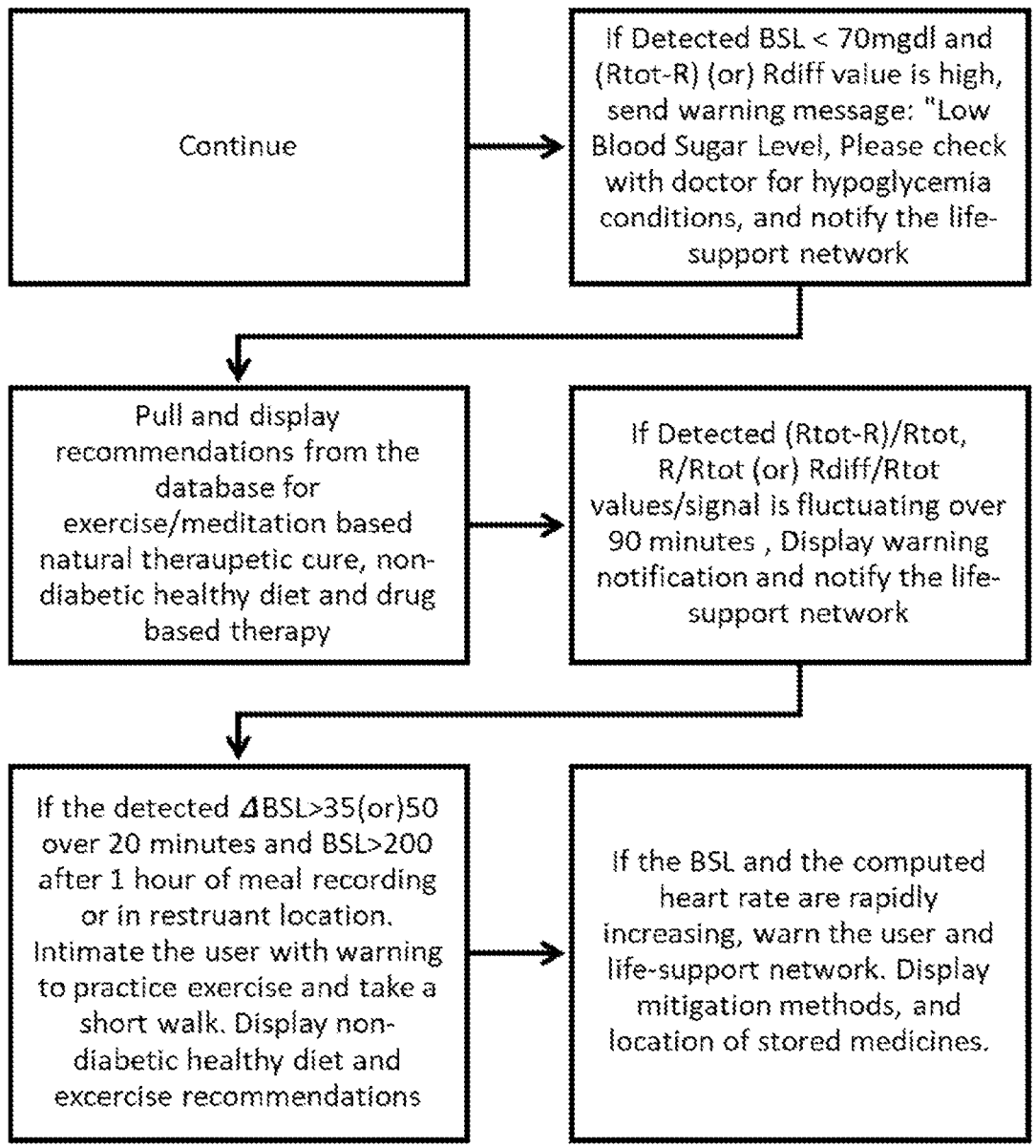

FIG. 9A and FIG. 9B show the method of blood sugar analysis for recognizing the hypoglycaemia, hyperglycemia and unusual blood sugar fluctuations. The values of continuous blood sugar values (BSL) and blood sugar fluctuations (ΔBSL) are analyzed during fasting glucose state, post-meal state, post-sleep condition, regular condition, and pre-meal state for recognizing prediabetic threshold condition, hyperglycemia threshold condition and hypoglycaemia threshold condition. The real-time system analyses BSL fluctuation values (ΔBSL) and real-time BSL values with respect to user location. The pulse rate and blood sugar data are evaluated for threshold blood sugar conditions and other health issues. The real-time system analyses and evaluates the red signal values, red signal dispersion values, infrared radiation dispersion values and visible signal values [(Rtot-R)/Rtot, R/Rtot, Rdiff/Rtot, IRdiff, and so on] for learning and recognizing unusual blood sugar fluctuations, hypergly-cemia, hypoglycaemia and prediabetes conditions. The system informs the user with information on the recognized health condition, present blood sugar levels and current blood sugar fluctuations. Subsequently, the system verifies probable symptoms, and automatically generates and displays recommendations from database on therapy methods, treatment centres, lifestyle practices, diet suggestions, required physical activities, mitigation methods and medication advice to treat and manage the recognized blood sugar conditions. The real-time system also automatically notifies and alerts the life-support network with a warning message and information on user data, user condition, user location, recognized health condition, present blood sugar levels, current blood sugar fluctuations and other essential data. Based on the real-time data and recognized health conditions, the user is automatically presented with real-time medical alert, medication reminder and information on location of the medication.

FIG. 10 shows the real-time system for monitoring continuous blood pressure levels. Initially, the recorded red signal response is adjusted according to the green signal response (Rtot1=Rtot−Y.ln(GPAR)). Then the oscillatory values of the red signal ($RT_{osc}$) are derived from the adjusted red signal values. Then, the peak to peak cycle of the red signal is analysed for a fixed time span for deriving the power of the red oscillatory signal (RP=$\Sigma f_0^{tpeak}$|RTosc|*|RTosc|). The linear and non-linear correlation is applied to the red signal power and calibrated blood pressure value to compute the real-time blood pressure (Ex: BP=X.RP). Then, the sensors are calibrated for tracking real-time blood pressure. The computed continuous blood pressure values are stored and displayed.

Figure 11A:
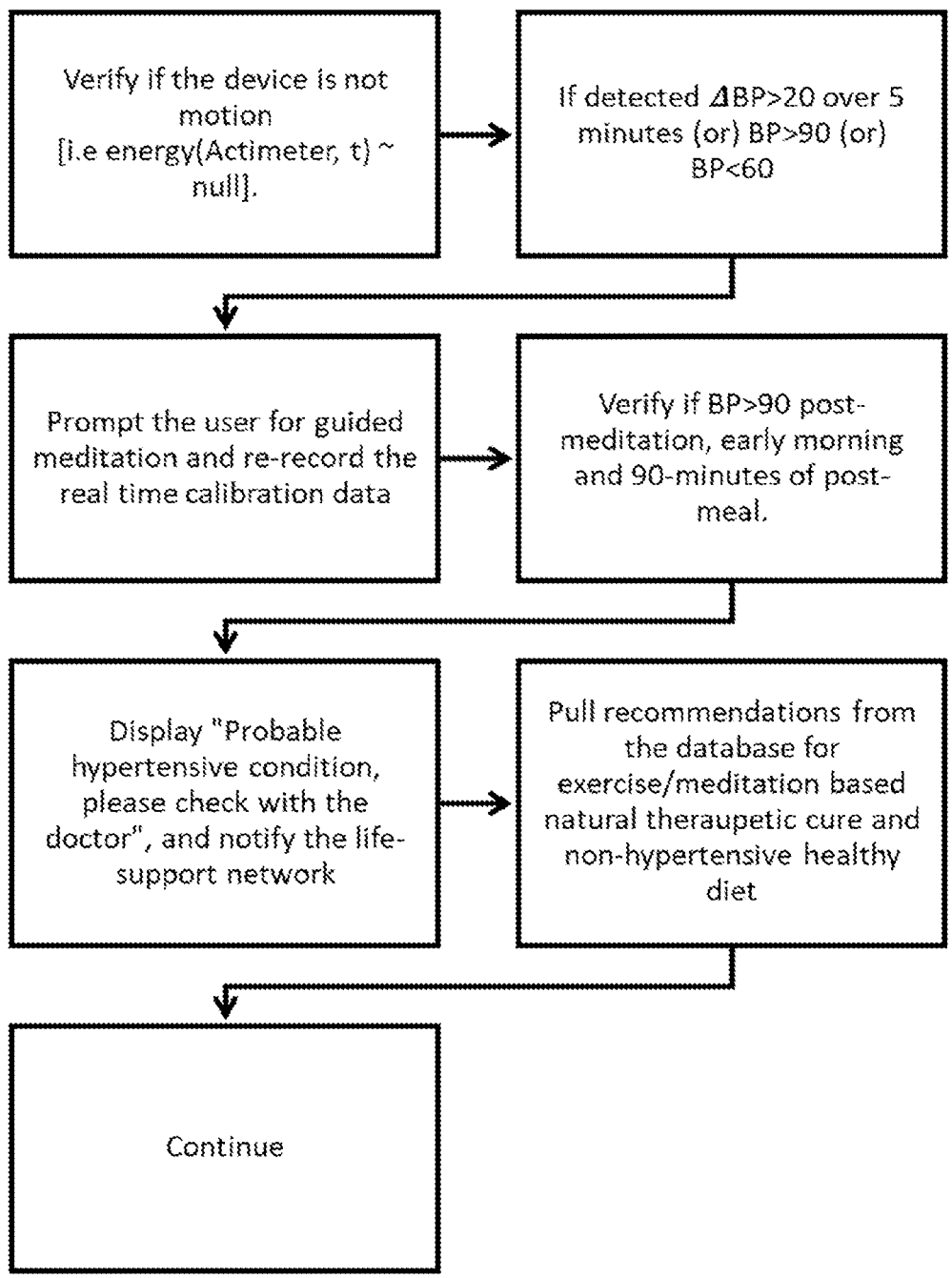
Figure 11B:
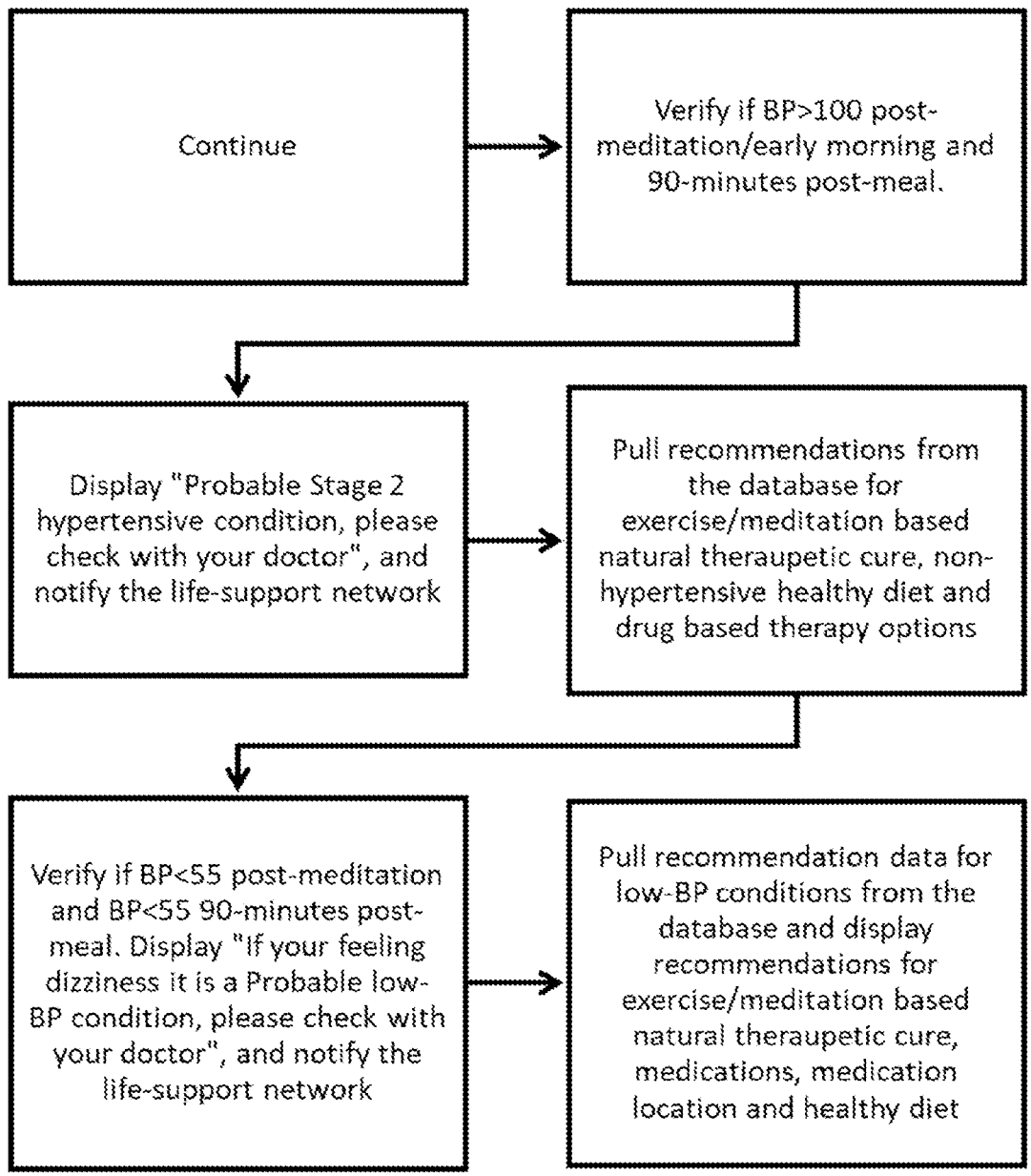

FIG. 11A and FIG. 11B show the method to analyse the continuous blood pressure data for recognizing the hypertension, hypotension, and unusual blood pressure fluctuations. The values of continuous blood pressure values (BP) and blood pressure fluctuations (ΔBP) are analyzed during fasting glucose state, post-meal state, post-sleep state, post-meditation state, regular condition, and pre-meal state for recognizing hypertension, hypertension stage 2, hypotension, and unusual blood pressure fluctuations. The system further analyses the blood pressure values (BP) and blood pressure fluctuations (ΔBP) for different locations. The system informs the user with information on the recognized health condition, present blood pressure levels and current blood pressure fluctuations. Subsequently, the system verifies probable symptoms, and automatically generates and displays recommendations from database on therapy methods, treatment centres, lifestyle practices, diet suggestions, physical activities, mitigation methods and medication advice to treat and manage the recognized blood pressure condition. Then, the real-time system also automatically notifies and alerts the life-support network with a warning message and information on user data, user condition, user location, recognized health condition, present blood pressure levels, current blood pressure fluctuations and other essential data. Based on the real-time data and recognized health condition, the user is automatically presented with real-time medical alert, a message to consult the doctor, medication reminder and information on location of the medication.

FIG. 12 shows the real-time system and automated method for recognizing psychological stress. The real-time system initially evaluates the real-time blood pressure and blood pressure fluctuations for verifying the state of psychological stress. Then, neural parameters of HP1, HP2 and HP3 are derived utilizing temporal analysis. The peak to peak temporal values of red signal response are evaluated for 0.05 s interval difference for deriving HP1. The peak to peak root mean square and mean values are evaluated for deriving HP2 and HP3. The derived parameters of HP1, HP2 and HP3 are compared with the resting values of HP1, HP2 and HP3 for recognizing the state of emotional stress. The system verifies the location data for verifying the state of emotional stress with respect to the relevant location (Ex: stress at work and home is common, else it is chronic stress condition). Then, the real-time system automatically notifies the user regarding the state of emotional stress and generates suggestions to manage the stress through exercise, guided meditation and diet and social networking platform. The real-time system also automatically alerts and notifies the life-support network with a warning message and information on user data, user condition, user location, recognized emotional condition.

FIG. 13 shows an automated sleep tracking system. The real-time system evaluates the movement data, body temperature, blood sugar levels, blood pressure data and bio-signal data of the user for recognizing the state of sleep. Then, the system assesses the values of blood pressure data, blood sugar levels and neural parameters (of HP1, HP2 and HP3) with sleep and wake data for recognizing REM sleep cycle and NREM sleep cycle. The REM cycle duration, NREM cycle duration, total sleep duration and sleep health are incremented and cached. The computed results are stored and displayed. The real-time system further analyses the actimeter data and sleep results to automatically recognize the sleep quality and the disturbed sleep condition. Based on the recognized sleep quality, the symptoms are verified, and the system automatically generates recommendations from database on recovery techniques, meditation methods, therapy methods, treatment centres, lifestyle practices, diet suggestions, physical activities, medications and health advice to manage the recognized sleep disorder. The real-time system also automatically alerts and notifies the life-support network with a warning message and information on user data, user condition, user location and recognized health condition. A learning method is applied on the derived parameters for reducing analysis parameters count, mode switching, complexity and power consumption of the processing method.

FIG. 14 shows a program for operating the telemetry apparatus using the buttons and navigator input. The long hold of button B1 turns on/off the device and short hold of button B1 swaps the operating modes of the device. The three short holds of the button B2 switches on/off the IOT parallel computational mode and wireless mode of the device. The long hold of button B2 facilitates the wireless synchronization and wireless data transfer between the telemetry apparatus and wireless devices. On recognizing long hold of the button B3, the device prompts the user to record the calibration values and real-time biometric values. The 5 short holds button B3 marks psychological stress levels of the user. Simultaneous long hold of B1/B3 and B2 silently triggers Emergency Alert in the wireless life-support network. Simultaneous long hold of B1 and B3, triggers alarm and medical emergency alert in the wireless life-support network. The rotation of the navigator crown swaps internal applications of the current mode in the direction of voltage shift or adjusts the intensity of the fancy LED.

FIG. 15 shows a user database based method for estimating calibration and health parameters. The color index, age, BMI, fat %, gene Info, sensor intensity, signal response and real-time calibration values are recorded from the individual user devices and sent to the central server. The values sent from the user device to the central server are analyzed and statically matched with the previously recorded parameters of the database. The optimization parameters of color index, sensor calibration data, healthy H.R. index, performance index and progress index are learnt and derived from the central database. The parameters are returned to user device, which is utilized for processing the real-time biological information and other health parameters.

FIG. 16 shows the design of the automated emergency response system. The emergency response system comprises of near-by synchronized mobile devices, SOS network, paired life-support devices and devices in the location of user's vicinity. On recognizing emergency trigger, the system checks for the status of the wireless antennae and the system automatically turns on the switched off wireless antennae. The location data and real-time biological information are recorded through the wireless antennae set and the internal sensors. The recorded information is transferred to the central server, SOS network, synchronized life-support device and the devices in the vicinity of user location. The set of life-support devices gets synchronized and receives the dataset. The life-support network triggers the primary network for transferring next dataset to the life-support network. The wireless data transfer occurs through directly via medium of central server and through other wireless methods.

FIG. 17 shows the network of wireless computational and storage devices. The Telemetry device 145 transfers the information to the server computer 146 and the other accessorial devices 147 through wireless methods. The accessorial mobile apparatus 147, server computer 146 and other network devices are utilized for parallelly computing and storing the information. This network of devices based method is used as a faster and efficient means to compute and store the required information. When necessary, the user device 145 retrieves the computed and stored information from the server 146 and accessorial devices network 147.

FIG. 18 shows the fancy LED apparatus. The fancy LED 148 emits multi-colored light in the line of branching multiple optical tubes 149. The light emitted to represent different device modes, device status and decorative application is perceived through the different branches of the multiple optical tubes 149.

Series of FIG. 19 show sample user interface of the telemetry apparatus and synchronized accessorial mobile device for recording user information and calibration values. FIG. 19A shows the user interface 150 for recording the essential user information. During the device startup, the profile picture 151, user name 152, age 153, basal metabolic index 154, fat % 155, weight 156, height 157 and gene info 158 of the user are recorded through the real-time telemetry or the accessorial mobile apparatus. FIG. 19B shows the interface 159 for recording contact picture. FIG. 19C is the interface 160 of the telemetry apparatus and the accessorial mobile apparatus for recording the calibration values of real-time blood sugar levels and blood pressure data during the device startup. FIG. 19D is the interface 161 of the telemetry apparatus and the accessorial mobile apparatus for recording the calibration values of real-time blood sugar levels and blood pressure data during the state of fasting glucose. FIG. 19E is the automated interface 162 of the telemetry apparatus and the accessorial mobile apparatus for recording the post morning sleep calibration values of real-time blood sugar levels and blood pressure data. FIG. 19F is the interface 163 of the telemetry apparatus and the accessorial mobile apparatus for recording the post-breakfast calibration values of real-time blood sugar levels and blood pressure data. FIG. 19G is the interface 164 of the telemetry apparatus and the accessorial mobile apparatus for recording the pre-lunch calibration values of real-time blood sugar levels and blood pressure data. FIG. 19H is the interface 165 of the telemetry apparatus and the accessorial mobile apparatus for recording the post-lunch calibration values of real-time blood sugar levels and blood pressure data. FIG. 19I is the interface 166 of the telemetry apparatus and the accessorial mobile apparatus for recording the post-exercise calibration values of real-time blood sugar levels and blood pressure data. FIG. 19J is the interface 167 of the telemetry apparatus and the accessorial mobile apparatus for recording the pre-dinner calibration values of real-time blood sugar levels and blood pressure data. FIG. 19K is the interface 168 of the telemetry apparatus and the accessorial mobile apparatus for recording the post-dinner calibration values of real-time blood sugar levels and blood pressure data. FIG. 19L is the interface 169 of the telemetry apparatus and the accessorial mobile apparatus for recording the before-bedtime calibration values of real-time blood sugar levels and blood pressure data.

FIG. 20 shows automated user interface 170 of the telemetry apparatus and synchronized accessorial mobile device for recording and accessing detailed diet information. The device automatically prompts the user to record detailed diet information of the meal name 171, meal quantity 172 and macronutrition and micronutrition 173.

Series of FIG. 21 show automated user interface of the telemetry apparatus and synchronized accessorial mobile device for accessing detailed real-time biological information. FIG. 21A is the automated interface 174 with real-time information on blood sugar levels, blood pressure data, neural activity, heart rate, oxygen saturation ratio and biotemperature with health sense message 175. The health sense message 175 shows the current status and progress of the stress management and other health disorder management. FIG. 21B is the sample interface 176, which shows real-time information on current blood sugar levels 177 and past blood sugar trend 178. FIG. 21C is the automated interface 179, which shows real-time information on current blood pressure levels 180 and past blood pressure trend 181. FIG. 21D is the automated interface 182, which shows real-time information on pulse rate 183 and oxygen saturation ratio 184 with real-time signal pattern 185. The automated user interfaces are automatically displayed on the user device in a timely manner.

Figure 22A:
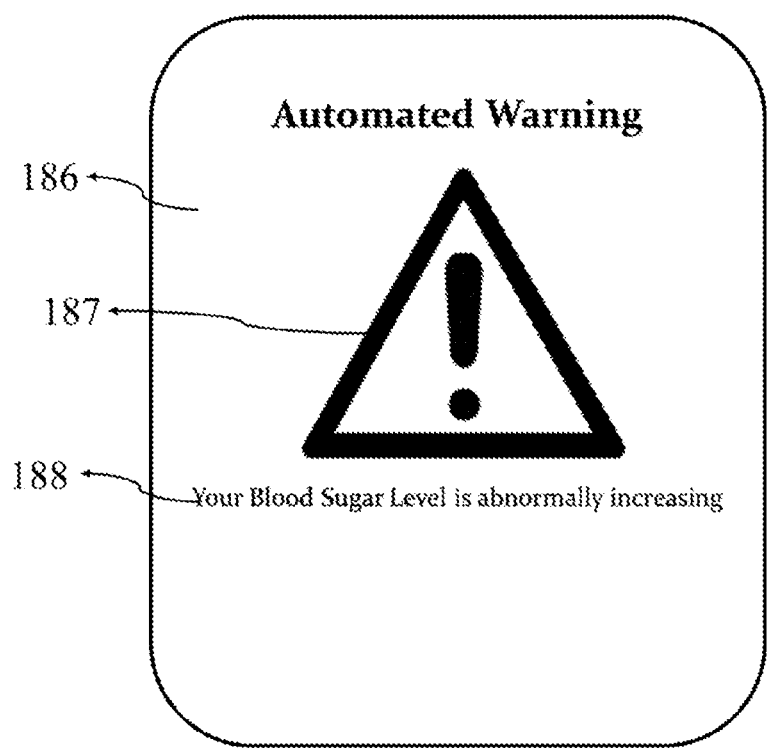
Figure 22B:
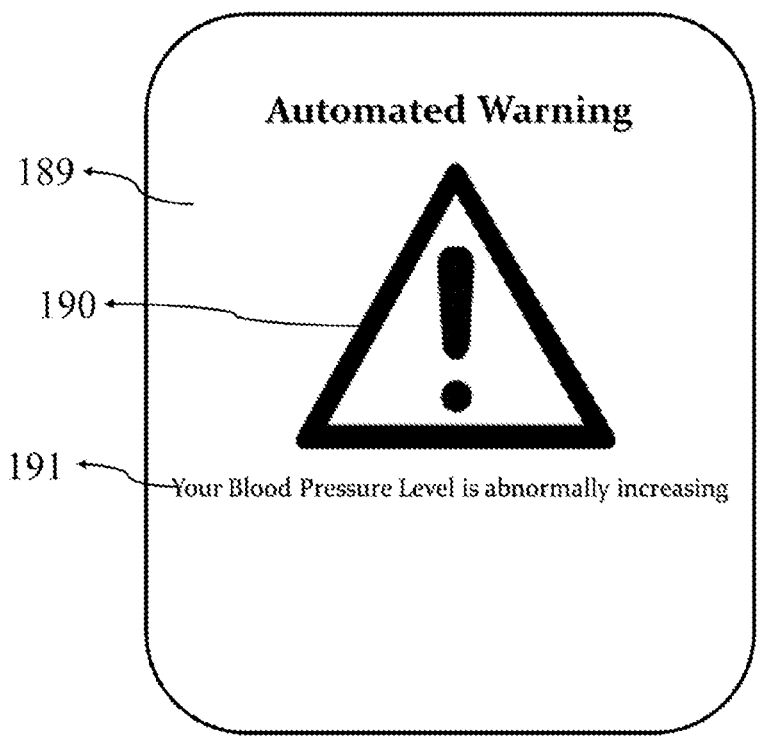
Figure 23A:
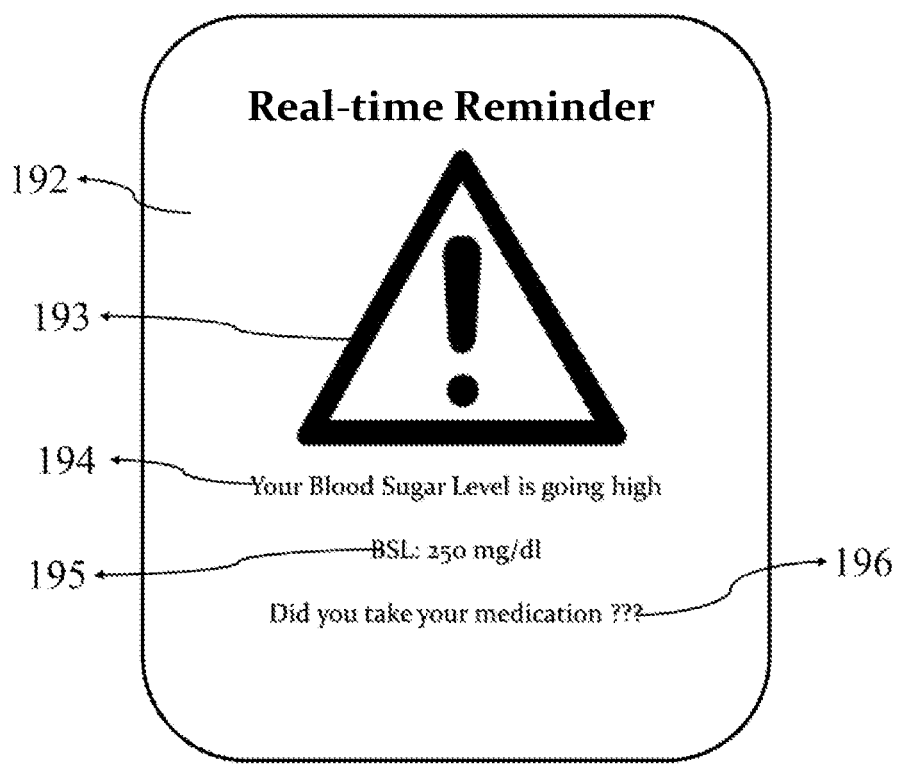
Figure 23B:
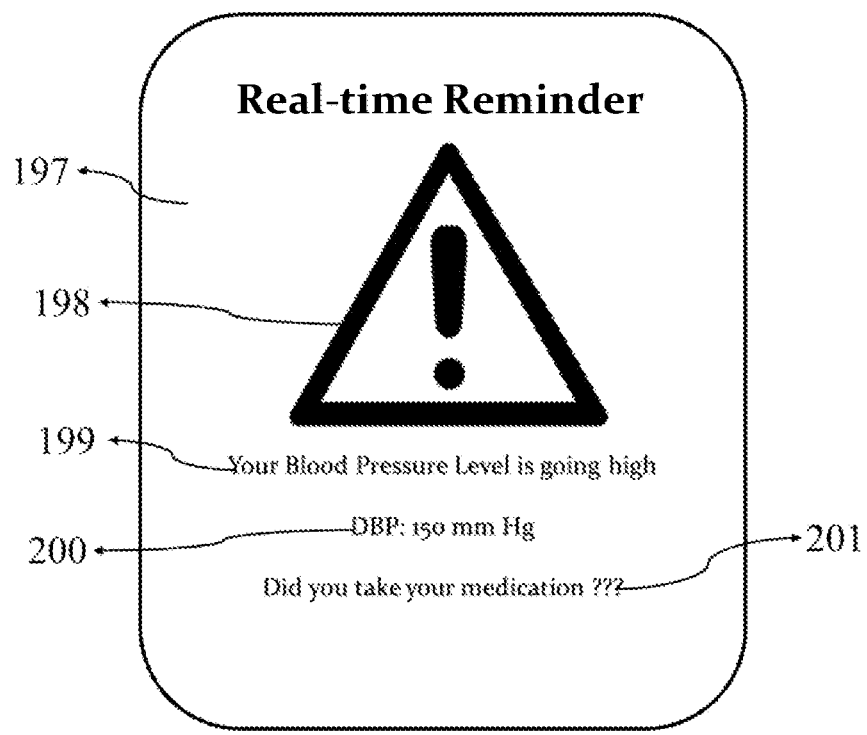
Figure 23C:
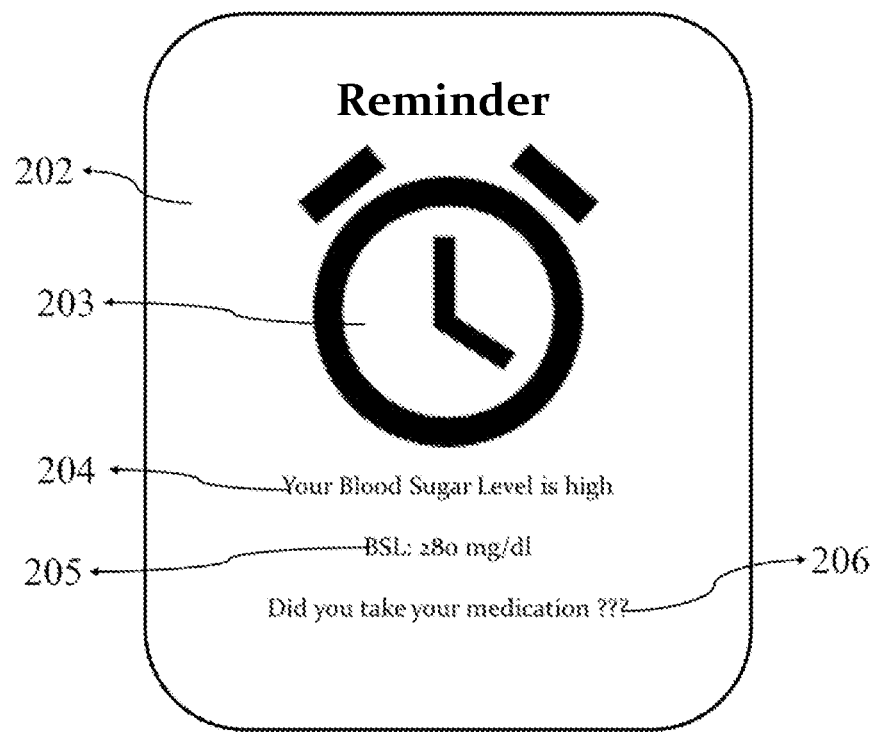
Figure 23D:
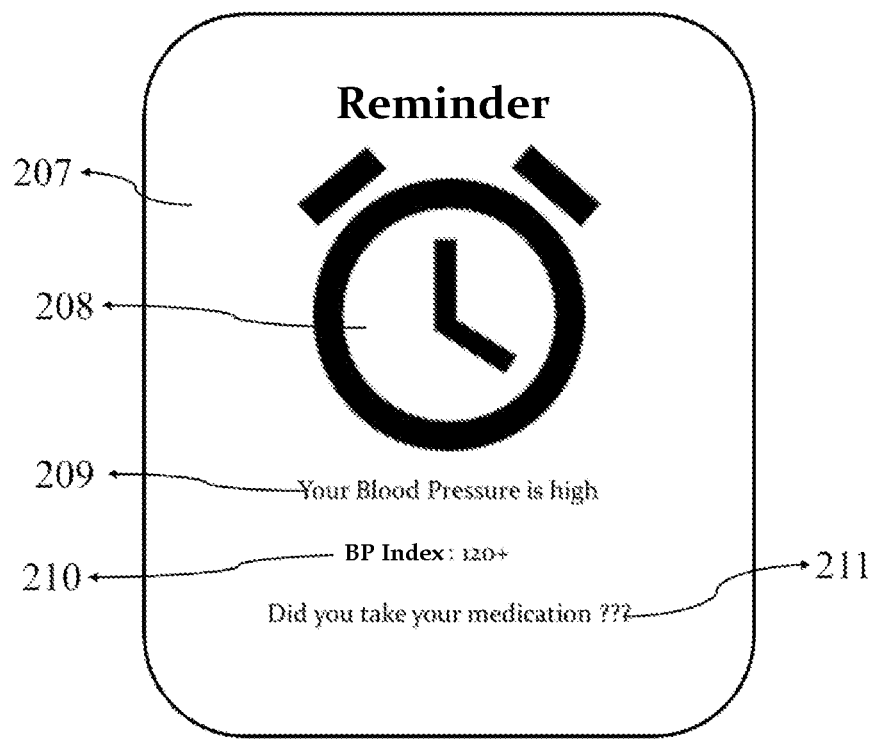

Series of FIG. 22 show sample interface of the automated real-time alerting system. FIG. 22A is the sample interface 186 that displays an automated warning 187 based on the real-time data with information on the unusual fluctuation (of the blood sugar levels 188). FIG. 22B is the sample interface 189 that displays an automated warning 190 based on the real-time data with information on the unusual fluctuation (of the blood pressure levels 191).

Series of FIG. 23 show the real-time medication reminders that is displayed for unusual real-time biological data fluctuations and unusual physiological state. FIG. 23A is the interface 192 that displays an automated warning 193, unusual fluctuation message 194 and a medication reminder message 196 with information on real-time blood sugar levels 195. FIG. 23B is the interface 197 that displays an automated warning 198, unusual fluctuation message 199 and a medication reminder message 201 with information on real-time blood pressure 200. FIG. 23C is the interface 202 that displays an automated reminder 203, notification on blood sugar abnormality 204 and a medication reminder message 206 with information on real-time blood sugar levels 205. FIG. 23D is the interface 207 that displays an automated reminder 208, notification on blood pressure abnormality 209 and a medication reminder message 211 with information on real-time blood pressure levels 210.

Figure 24A:
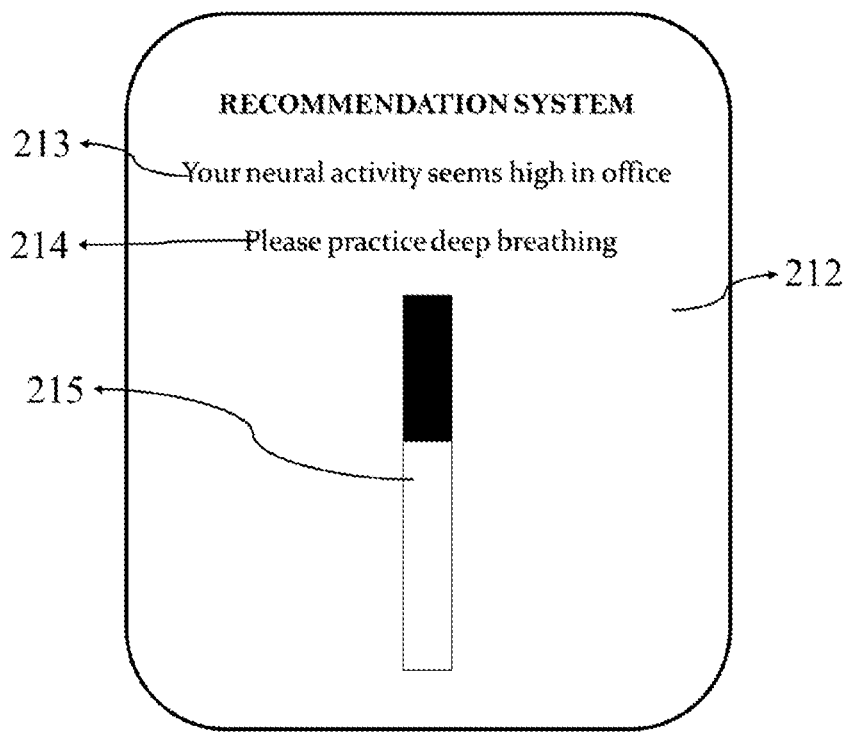
Figure 24B:
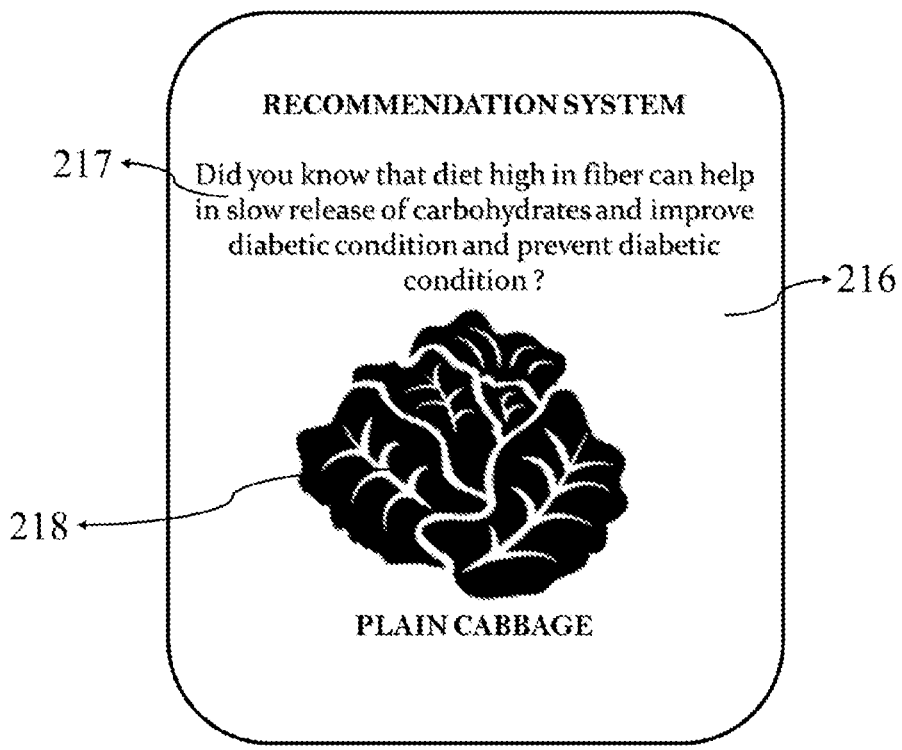

Series of FIG. 24 show the sample interface of the automated recommendation system. The automated recommendations are displayed on daily basis for specific health management purpose and also based on the real-time biological information. FIG. 24A is the sample interface 212 that displays unusual biological information with location 213, health management method 214 for the recognized health condition and real-time physiological data 215. FIG. 24B is the sample interface 216 that displays diet management technique 218 for recognized health condition with additional scientific and nutritional information about the recommended diet 217.

FIG. 25A and FIG. 25B show a size adjustable clipper embodiment form of the telemetry apparatus. The ring apparatus comprises of a main ring body 219 packaged with electronics and a mechanical gripping element 220. The near-infrared signal probe set 224, transmittive green signal probe set 225, infrared signal probe set 226 and red signal probe set 227 are placed on the upper side of the contact surface 223. The near-infrared detector probe set 230, green detector probe set 231, infrared detector probe set 232 and red detector probe set 233 are placed in alignment with their corresponding signal probes and on the bottom side of the contact surface 223. The green signal probe 228 and green photodetector probe 229 of the reflective green spectrometer are placed at an optimal adjacent sensing spot of the contact surface 223. A non-contact temperature bio-sensor 234 is embedded on the contact surface for extracting real-time bio-temperature signals and thermal feedback. The contact surface 223 is covered with foam base or sponge 235 around the biosensors, which is used as the mechanical means to enhance the grip and reduce the real-time movement errors. The micro-USB charging and data transfer port 236 and the set of user interaction system of mic 239, micro-speaker 240, buttons 241-242 and navigator crown 243 are embedded on the outer surface 222 of the main ring frame 219. A wireless charging coil 237 and the fancy LED apparatus 238 are embedded inside the ring. The mechanical clipping element 220, comprising of hinge1 244-clip1 245 and hinge2 246-clip2 247, is attached to the main ring frame 219. The clutching action of the hinge1 244-clip1 245 and hinge2 246-clip2 247 is used as a size adjustable method to grip and fasten the ring apparatus. The entire ring apparatus is further covered with waterproof coating 221.

FIG. 26 shows a dual clipper based ring embodiment form of the telemetry apparatus. The dual clipper comprises of near-infrared and green optical spectrometer apparatus 251 and infrared-red optical spectrometer apparatus 252 embedded on the contact surface 249. The non-sensor area of the contact surface 249 is covered with foam base or sponge like material 253. The button B1 254, button B2 255, button B3 256, navigator crown 257, micro-USB port and other set of user interaction components are embedded on the outer surface 250 of the ring frame 248. The set of upper holding clip 260 and bottom holding clip 261 are attached to the main ring frame 248 through their corresponding movable hinges of 259 and 258. The extender hinge 262 of upper holding clip 260 and extender hinge 263 of bottom holding clip 261 are used as the means to adjust the size of the holding clips. The clutching action of the holding clip 260 with extender hinge 262-holding clip 261 with extender hinge 263 and the movable hinges 259-258 are used as the means to securely fasten the ring device.

FIG. 27A, FIG. 27B and FIG. 27C show the solar powered handheld monitoring embodiment form of the telemetry apparatus.

FIG. 27A shows the front isometric view of the handheld monitoring embodiment form. The micro-USB 265 and a button 266 are embedded on the side surface 264 of the monitor. The mini-touch screen 268 is embedded on the front side of the monitor, which is utilized to operate the apparatus and its inbuilt applications. The monitoring device is covered with waterproof coating 267. The device further comprises of a detachable wearable chord 269. The detachable chord 269 has a chord adjusting element 270 and an extender chord 271 for altering the size of the chord 269.

FIG. 27B shows the back-isometric view of the handheld monitor. A button 273 is embedded on the other side surface 272 of the monitor. A set of a detachable auxiliary powering module comprising of solar module 1 276, solar module 2 277, actuator hinge 275 and actuator 274 are attached to the back surface of the device. The actuator 274 extends the solar module 2 277 through the actuator hinge 275 from plane of solar module 1 276 for harvesting more solar energy. The actuation of the solar module 2 277 occurs automatically or through control command.

FIG. 27C shows the bottom isometric view of the handheld monitor. The bottom surface 278 of the monitor has a finger placement area 279 embedded with bio-sensors in transmittive configuration. The signal probe 281 and detector probe 282 are aligned inside the finger placement area 279 in transmittive sensing configuration. The area around the bio-sensors of the finger placement area 279 is surrounded by foam base or sponge 280. The foam base or sponge 280 is utilized to enhance the grip and reduce the real-time movement errors.

FIG. 28 shows the earphone embodiment of the telemetry apparatus. The earphone apparatus comprises of a transmittive sensing apparatus 283 with an ear placement area 284. The transmittive sensing apparatus 283 is attached to the music ear-bud 287 through the ear hook clip 285. The fancy LED apparatus 286 is embedded inside the earphone near the ear hook 285. The device is covered with water proof coating 288. The ear-bud 287 and the ear hook 285 are used to securely hold the device on the sensing spot. The music ear-bud 287 is further utilized for perceiving audio output.

The above described invention disclosure is intended for illustration purposes, and for those skilled in the art may instantly perceive numerous suggestive modifications, variations and equivalents. Therefore, the disclosure is not exhaustive in broader aspects and the invention is not intended to limit to specific details, spectrometer instruments, illustrated hardware designs, described computational methods and embodiment forms. All equivalents and modifications are intended to be included within the scope of disclosure and attached claims. Accordingly, additional changes and modifications may be made without departing from the scope and the spirit of the invention disclosure appended in the document, claims and their equivalents.

INDUSTRIAL APPLICABILITY

The disclosure presents transmittive sensing based low-powered and totally non-invasive continuous glucose monitoring solution. The described intelligent technology can be utilized as telemetry clinical instrumentation, neo-natal medical device, gestational diabetes monitoring apparatus, real-time diagnostic technology, portable medical apparatus, in-vitro and in-vivo biosensing instrument, general wellness management device, smart wearable device, server based real-time clinical diagnosis system, life-support device, health tracking software device, real-time intelligent medical reminder, automated recommendation system and software medical device.

PRIOR ART AND CITATION LIST

EP 0160768 B1 (Kurabo Industries Ltd) 4 May 1984
U.S. Pat. No. 5,028,787 A (Futrex, Inc.) 19 Jan. 1989
WO 1992000513 A1 (Futrex, Inc.) 27 Jun. 1990
U.S. Pat. No. 4,953,552 A (Arthur P. DeMarzo) 4 Sep. 1990
U.S. Pat. No. 4,979,509 A (Northstar Res Inst Ltd) 25 Dec. 1990
U.S. Pat. No. 5,139,023 A (Actavis Laboratories UT Inc Stanley Res Foundation) 18 Aug. 1992
WO 1992017765 A1 (Johnson & Johnson Professional Products Limited) 15 Oct. 1992
US 20020123677 A1 (Bois Labs Inc) 28 Dec. 2000
US 006819950 B2 (Alexander K. Mills) 16 Nov. 2004
U.S. Pat. No. 6,675,030 B2 (Euroceltique SA) 6 Jan. 2004
CN 102217939 A (Shanghai Jiao Tong University) 19 Oct. 2011
U.S. Pat. No. 8,280,476 B2 (ArKal Medical Inc) 2 Oct. 2012

Hereto the following are claimed:

1. A telemetry apparatus, for monitoring physiological parameters, comprising:
a near-infrared optical spectrometer comprising:
a plurality of near-infrared light sources configured to provide a constructive interference of a near-infrared radiation;
a set of lens system comprising a first near-infrared optical lens system configured to constructively focus the near-infrared radiation on a sensing spot and a second near-infrared optical lens system configured to focus a near-infrared response on a near-infrared photodetector;
an infrared optical dispersion analyzer spectrometer comprising:
a central infrared LED configured to focus a first infrared light on a first central photodetection spot of the sensing spot;
one or more of a non-central infrared LED configured to focus one or more of a second infrared light on the first central photodetection spot;
a central infrared photodetector configured to record a first infrared optical response;
one or more of a non-central infrared photodetector configured to record one or more of a second infrared optical response, wherein the first infrared optical response and one or more of the second infrared optical response are configured to provide an infrared optical dispersion signal;
a red optical dispersion analyzer spectrometer comprising:
a central red LED configured to focus a first red light on a second central photodetection spot of the sensing spot;
one or more of a non-central red LED configured to focus one or more of a second red light on the second central photodetection spot;
a central red photodetector configured to record a first red optical response;
one or more of a non-central red photodetector configured to record one or more of a second red optical response, wherein the first red optical response and one or more of the second red optical response are configured to provide a red optical dispersion signal;
a green optical spectrometer configured to record a green optical response, wherein the green optical spectrometer comprises at least a transmittive arrangement or a reflective arrangement;
a telemetry hardware comprising a microprocessor with memory, circuits and electronics, wherein the telemetry hardware is configured to extract:
a real-time blood sugar level data by correlating the near-infrared response with the first infrared optical response, one or more of the second infrared optical response, the first red optical response, one or more of the second red optical response and the green optical response; and
a continuous blood pressure level data by correlating the first infrared optical response, one or more of the second infrared optical response, the first red optical response and one or more of the second red optical response with the green optical response.

2. The telemetry apparatus in claim 1, wherein the green optical spectrometer, selected in the transmittive arrangement, comprises:
a green LED and a first green optical lens system configured to focus a green light on the sensing spot in a transmittive direction; and
a second green optical lens system configured to focus a transmitted response of the green light on a green photodetector for recording the green optical response.

3. The telemetry apparatus in claim 1, wherein the green optical spectrometer, selected in the reflective arrangement, comprises:
a green LED and a first green optical lens system configured to inject a green light at least at a critical angle on the sensing spot to bounce back from a skin boundary; and
a second green optical lens system configured to focus a reflected response of the green light on a green photodetector for recording the green optical response, wherein the second green optical lens system and the green photodetector are embedded at a noise free response recording spot.

4. The telemetry apparatus in claim 1, wherein the infrared optical dispersion analyzer spectrometer further comprises:
a first infrared optical lens system configured to focus the first infrared light on the first central photodetection spot;
one or more of a second infrared optical lens system configured to focus one or more of the second infrared light on the first central photodetection spot;
a third infrared optical lens system configured to focus the first infrared optical response, at a central response receiving spot, on the central infrared photodetector; and
one or more of a fourth infrared optical lens system configured to focus one or more of the second infrared optical response on one or more of non-central infrared photodetector.

5. The telemetry apparatus in claim 4, wherein one or more of the second infrared optical lens system is tilted or one or more of the non-central infrared LED and one or more of the second infrared optical lens system are titled at one or more of an angle configured to focus one or more of the second infrared light on the first central photodetection spot.

6. The telemetry apparatus in claim 1, wherein the red optical dispersion analyzer spectrometer further comprises:
a first red optical lens system configured to focus the first red light on the second central photodetection spot;
one or more of a second red optical lens system configured to focus one or more of the second red light on the second central photodetection spot;
a third red optical lens system configured to focus the first red optical response, at a central response receiving spot, on the central red photodetector; and
one or more of a fourth red optical lens system configured to focus one or more of the second red optical response on one or more of the non-central red photodetector.

7. The telemetry apparatus in claim 6, wherein one or more of the second red optical lens system is tilted or one or more of the non-central red LED and one or more of the second red optical lens system are titled at one or more of an angle configured to focus one or more of the second red light on the second central photodetection spot.

8. The telemetry apparatus in claim 1, wherein the telemetry hardware further comprises:
a tuneable active amplifier circuit configured to coherently drive inputs to the plurality of near-infrared light sources;
a primary switch set configured to shift a plurality of input signals between a plurality of input lines of the near-infrared optical spectrometer, the green optical spectrometer, the infrared optical dispersion analyzer spectrometer and the red optical dispersion analyzer spectrometer to reduce a power consumption;
a set of switches configured to alternatively drive the plurality of input signals to, the central infrared LED and one or more of the non-central infrared LED of, the infrared optical dispersion analyzer spectrometer and to, the central red LED and one or more of the non-central red LED of, the red optical dispersion analyzer spectrometer;
a LED frontend, comprising a LED driver, a LED controller, a pulse width modulation unit (PWM) and a clock controller, configured to variably trigger and provide the plurality of input signals;
a set of photodetector switches configured to alternatively drive the first infrared optical response and one or more of the second infrared optical response of the infrared optical dispersion analyzer spectrometer and the first red optical response and one or more of the second red optical response of the red optical dispersion analyzer spectrometer respectively to a central photodetector response line and a non-central photodetector response line;
a primary photodetector switch set configured to shift a plurality of output responses, from the near-infrared optical spectrometer, the infrared optical dispersion analyzer spectrometer, the red optical dispersion analyzer spectrometer and the green optical spectrometer, to a photodetector circuit to reduce the power consumption;
one or more of a Darlington Pair circuit configured to amplify the plurality of output responses;
a circuit line, comprising an ADC, an ambient noise cancellation IC and a DAC, configured to filter noises in the central photodetector response line and the non-central photodetector response line;
a real-time dispersion analyser circuit, comprising an instrumental amplifier, configured to extract a real-time dispersion information from the central photodetector response line and the non-central photodetector response line;
the photodetector circuit, comprising a power notch, an ADC, an ambient noise cancellation IC and a transimpedance amplifier, configured to filter noises in and process the plurality of output responses;
an IC configured to extract a summed non-central photodetector response of two or more of the second infrared optical responses or two or more of the second red optical responses;
a temperature biosensor configured to extract a real-time body temperature and a temperature feedback to adjust the plurality of output responses;
an ambient temperature sensor configured to extract a real-time environment temperature and a feedback to adjust the plurality of output responses;
a 9/6-axis accelerometer configured to provide a real-time feedback to remove a motion noise and compute a plurality of movement data;
a touch display configured to provide an access to a plurality of calibrations, a plurality of real-time medical information, a plurality of medical alerts and a plurality of automated recommendations;
a mic and a speaker configured for interacting with a plurality of medical and health professionals for a clinical and health analysis and for operating the telemetry apparatus;
a navigator crown comprising a potentiometer and a fixed impedance component;
a plurality of buttons and the navigator crown configured to provide an access to the plurality of calibrations and to operate the telemetry apparatus;
a LED circuit configured to automatically indicate a user condition, display one or more of a decorative application and represent a plurality of operating modes and device status;
a wireless antennae set, comprising a Bluetooth connection, a wireless local area network connections (WLAN) and a global positioning system (GPS), configured to:

extract a location data and the plurality of movement data;
communicate to a life-support network and a network of external computational devices;
a power management IC configured to regulate a power supply;
a supercapacitor and a battery set configured to store energy and supply power;
a second supercapacitor and a renewable energy harvester configured to provide an auxiliary powering;
a negative voltage converter configured to generate a negative signal reference; and
a wireless coil configured to wirelessly charge the battery and to supply power.

9. The telemetry apparatus in claim 8, wherein the wireless antennae set of the telemetry hardware, further comprises a mobile communication module configured to:
extract the location data and the plurality of movement data; and
communicate to the life-support network and the network of external computational devices.

10. The telemetry apparatus in claim 1, wherein the telemetry hardware is configured to:
extract the real-time blood sugar level data by:
obtaining an area normalized value of the near-infrared response;
obtaining an area normalized value of an infrared power response, an integrated
infrared response and a differential infrared response that includes the infrared optical dispersion signal;
obtaining an area normalized value of a red power response, an integrated red response and a differential red response that includes the red optical dispersion signal;
obtaining an area normalized value of the green optical response;
deducing a green parameter from a DC parameter of the green optical response;
deducing a red oscillatory response from the integrated red response or the red power response;
deducing an infrared oscillatory response from the integrated infrared response or the infrared power response;
adjusting the near-infrared response as per temperature stats according to a bio-temperature response and an ambient temperature response;
obtaining a processed near-infrared response through a correlation of the near-infrared response with at least the infrared oscillatory response, the red oscillatory response, the green parameter, the differential red response, the integrated red response, the red power response, the differential infrared response, the integrated infrared response, the infrared power response or a color index to adjust for blood line losses, skin losses and dispersion losses;
correlating the processed near infrared response with one or more of a blood glucose calibration value comprising a regular condition value, a pre-meal value, a post-meal value, a post morning sleep value, a fasting glucose value, a post exercise value, a before bed time value, a sitting position value, a standing position value, a relaxing position value, a hyperglycemia state value and a hypoglycaemia state value;
extract a blood sugar fluctuation data from the real-time blood sugar level data;
recognize a hypoglycaemic condition, a hyperglycaemic condition and a prediabetes condition by analysing the real-time blood sugar level data and the blood sugar fluctuation data in a fasting glucose state, a post-meal state, a post-sleep state, a regular condition state and a pre-meal state;
recognize a blood sugar condition by analysing the real-time blood sugar level data and the blood sugar fluctuation data with respect to a user location that includes a restaurant location, wherein said blood sugar condition is the hypoglycaemic condition, the hyperglycaemic condition or the prediabetes condition;
recognize the blood sugar condition by analysing the real-time blood sugar level data and the blood sugar fluctuation data over a period of time that includes evaluating the blood sugar fluctuation data for a value of at least 70 over a 4 hour time period;
verify the blood sugar condition through a reverification in a same state and a cross verification in a different state that includes analysis in the fasting glucose state, the post-meal state and the regular condition state;
run a recalibration on recognizing the hypoglycaemic condition, the hyperglycaemic condition or an unusual fluctuation of blood sugar;
analyse and evaluate the differential red response, the integrated red response, the red power response, the differential infrared response, the integrated infrared response and the infrared power response to learn and recognize the hypoglycaemic condition, the hyperglycaemic condition and the prediabetes condition, wherein they comprise the first red optical response, one or more of the second red optical response, the first infrared optical response, one or more of the second infrared optical response, the infrared optical dispersion signal and the red optical dispersion signal;
verify symptoms and automatically provide a plurality of recommendations on a plurality of therapy methods, a plurality of treatment centres, a plurality of lifestyle practice, a plurality of diet suggestions, a plurality of required physical activities, a plurality of mitigation methods and a medication advice to treat and manage the blood sugar condition;
automatically present a real-time medical alert, a message to consult doctor, a medication reminder and a location of medication based on the blood sugar condition;
automatically alert a life-support network and a physician network, on recognizing the blood sugar condition, with a warning message and information on the blood sugar condition, the user location, user data, the blood sugar fluctuation data and the real-time blood sugar level data; and
automatically warn user and the life-support network, on recognizing a pattern of rapidly increasing values of the real-time blood sugar level data and a heart rate data, with the plurality of mitigation methods and the location of medication.

11. The telemetry apparatus in claim 1, wherein the telemetry hardware is configured to:
extract a the continuous blood pressure level data by:
obtaining an oscillatory signal adjusted according to a green parameter, wherein the green parameter is deduced from the green optical response and the oscillatory signal is deduced from the first infrared optical response, one or more of the second infrared optical response, the first red optical response and one or more of the second red optical response;

obtaining a power of the oscillatory signal for a fixed span of time;

correlating the power of the oscillatory signal with one or more of a blood pressure calibration value comprising a regular condition value, a pre-meal value, a post-meal value, a post morning sleep value, a fasting glucose value, a post exercise value, a before bed time value, a sitting position value, a standing position value, a relaxing position value, a hyperglycemia state value and a hypoglycaemia state value;

extract a blood pressure fluctuation data from the continuous blood pressure level data;

recognize a stage 1 hypertension condition, a stage 2 hypertension condition, a low blood pressure condition and a pre hypertension condition by analysing the continuous blood pressure level data and the blood pressure fluctuation data in a fasting glucose state, a post-meal state, a post-sleep state, a post-meditation state, a regular condition state and a pre-meal state;

recognize a blood pressure condition by analysing the continuous blood pressure level data and the blood pressure fluctuation data with respect to a user location, wherein said blood pressure condition is the stage 1 hypertension condition, the stage 2 hypertension condition, the low blood pressure condition or the pre hypertension condition;

verify the blood pressure condition through a reverification in a same state and a cross verification in a different state that includes analysis in an early morning state, the post-meal state, the post-meditation state and the regular condition state;

verify the blood pressure condition through a symptom verification that includes verifying a dizziness feeling for the low blood pressure condition;

verify symptoms and automatically provide a plurality of recommendations on a plurality of therapy methods, a plurality of treatment centres, a plurality of lifestyle practices, a plurality of diet suggestions, a plurality of required physical activities, a plurality of mitigation methods and a medication advice to treat and manage the blood pressure condition;

automatically present a real-time medical alert, a message to consult doctor, a medication reminder and a location of medication based on the blood pressure condition; and automatically alert a life-support network and a physician network, on recognizing the blood pressure condition, with a warning message and information on the blood pressure condition, the user location, user data, the continuous blood pressure level data and the blood pressure fluctuation data.

12. The telemetry apparatus in claim 1, wherein the telemetry hardware is configured to:
extract an emotional stress by:
verifying the continuous blood pressure level data and a blood pressure fluctuation data for a threshold of stress levels;
obtaining a HP1 parameter through an evaluation of an interval difference data, between a peak to peak temporal data of the first red optical response, with a fixed interval difference, wherein the fixed interval difference is at least a 0.05 seconds;
obtaining a HP2 parameter by taking a root of an average of a square of the interval difference data;
obtaining a HP3 parameter by taking an average of the peak to peak temporal data;

comparing a present data set of the HP1 parameter, the HP2 parameter and the HP3 parameter with a resting data set of the HP1 parameter, the HP2 parameter and the HP3 parameter;

verify a recognized state of the emotional stress through an assessment of a user location related to stress, wherein the user location related to stress includes a work location and a home location;

notify user on the recognized state of the emotional stress and automatically provide a plurality of recommendations on a plurality of exercises, a plurality of guided meditation methods, a plurality of diet and a plurality of social networking platforms to manage the recognized state of the emotional stress; and automatically alert a life-support network on recognizing the emotional stress with a warning message and information on the user location and user data.

13. The telemetry apparatus in claim 1, wherein the telemetry hardware is configured to:
recognize and record a sleep state, a rapid eye movement (REM) sleep cycle and a non-rapid eye movement (NREM) sleep cycle by:
evaluating a movement data, a body temperature, the continuous blood pressure level data and the real-time blood sugar level data for a realistic range and for the sleep state;
evaluating a real-time dataset of the continuous blood pressure level data, the real-time blood sugar level data, a HP1 parameter, a HP2 parameter and a HP3 parameter with a sleep dataset and a wake dataset to recognize the REM sleep cycle and the NREM sleep cycle;
storing a REM sleep cycle duration, a NREM sleep cycle duration and an overall sleep duration;
recognize a disturbed sleep state by analysing an actimeter data and a sleep results data of the sleep state, the REM sleep cycle and the NREM sleep cycle;
verify symptoms and automatically provide a plurality of recommendations on a plurality of recovery techniques, a plurality of meditation methods, a plurality of therapy methods, a plurality of treatment centres, a plurality of lifestyle practices, a plurality of diet suggestions, a plurality of physical activities, a plurality of medications and a health advice to treat and manage the disturbed sleep state;
automatically alert a life-support network on recognizing the disturbed sleep state with a warning message and information on a user location and user data; and
reduce a count of analysis parameters of sleep analysis.

14. The telemetry apparatus in claim 1 further comprises a plurality of user interaction components, comprising one or more of a button and a navigator crown, configured to:
swap operating modes and swap internal applications of a current mode;
facilitate a plurality of wireless synchronizations with a plurality of external devices and switch on an IOT parallel computational mode;
provide an access to calibration and enable marking of a psychological stress level; and
enable a silent trigger of an emergency alert and a trigger of a medical emergency alert in a life-support network.

15. The telemetry apparatus in claim 1 further comprises a plurality of user interaction components, comprising a button B1, a button B2, a button B3 and a navigator crown, wherein:
a long hold of the button B1 is configured to power on and off the telemetry apparatus;

a short hold of the button B1 is configured to swap an operating mode;

a long hold of the button B2 is configured to facilitate a plurality of wireless synchronizations with a plurality of external devices;

a multiple short hold of the button B2 is configured to switch on and off an IOT parallel computational mode, wherein a three short hold could be the multiple short hold;

a long hold of the button B3 is configured to provide an access to calibration;

a multiple short hold of the button B3 is configured to mark a psychological stress level, wherein a five short hold could be the multiple short hold of the button B3;

a simultaneous long hold of the button B1 and the button B2 is configured to enable a silent trigger of an emergency alert in a life-support network;

a simultaneous long hold of the button B1 and the button B3 is configured to enable a trigger of a medical emergency alert along with an alarm in the life-support network; and a rotation of the navigator crown is configured to swap between a plurality of internal applications of a current mode in a direction of rotation or a voltage shift.

16. The telemetry apparatus in claim 1, wherein the telemetry apparatus is configured to:

send an age, a color index, a BMI, a fat %, a plurality of calibration values and a plurality of sensor signal and intensity responses, comprising a plurality of output responses from the near-infrared optical spectrometer, the infrared optical dispersion analyzer spectrometer, the red optical dispersion analyzer spectrometer and the green optical spectrometer, of user to a central server;

receive a plurality of optimization parameters and health parameters comprising a sensor calibration data, a healthy H.R. index, a performance index and a progress index from a central database of the central server; and process a plurality of real-time biological information, that includes the real-time blood sugar level data, the continuous blood pressure level data, an emotional stress data, a sleep state data, a rapid eye movement sleep cycle data, a non-rapid eye movement sleep cycle data and a plurality of medical and health conditions, by implementing the plurality of optimization parameters.

17. A system comprising the telemetry apparatus in claim 1, and a plurality life-support network devices, wherein the system is configured to:

validate a status of a wireless antennae set of the telemetry apparatus and switch on the wireless antennae set in a switched off state on recognizing an emergency trigger;

record a location data from the wireless antennae set;

obtain a plurality of real-time biological information from the a plurality of sensors of the telemetry apparatus, wherein the plurality of sensors includes a temperature biosensor, an ambient temperature sensor, a 9/6-axis accelerometer, the near-infrared optical spectrometer, the infrared optical dispersion analyzer spectrometer, the red optical dispersion analyzer spectrometer and the green optical spectrometer; and transfer the location data and the plurality of real-time biological information to a central server, a plurality of SOS network devices and a plurality of near-by devices in a user location through a plurality of wireless connections established through the wireless antennae set the plurality of life-support network devices or through a medium of the central server.

18. The telemetry apparatus in claim 1, wherein the telemetry apparatus along with a network of computational and storage devices, comprising a server computer and a plurality of accessorial mobiles devices and external computers, are configured to execute a parallel computing to increase speed and efficiency of computations through, a plurality of wireless connections comprising, a Bluetooth connection, a wireless local area network connection (WLAN) and a mobile communication system connection.

19. A system comprising the telemetry apparatus of claim 1, and an accessorial mobile device, wherein the accessorial mobile device or the telemetry apparatus is configured to:

record a plurality of user information comprising a profile picture, a user name, an age, a basal metabolic index, a fat %, a weight, a height and a gene info;

record one or more of a contact picture;

record a plurality of blood sugar and blood pressure calibration values during a device startup stage, a fasting glucose state, a post morning sleep state, a post-meal state, a pre-meal state, a post-exercise state and a before-bedtime state;

record a macro-nutrition detail, a micro-nutrition detail and a meal information;

display a real-time information and a data trend on a plurality of real-time biological information, wherein the plurality of real-time biological information comprises the real-time blood sugar level data, the continuous blood pressure level data, a neural activity, a pulse rate, an oxygen saturation and a body temperature;

display a health sense message that shows a current status and a progress on stress management and health disorder management;

display an automated warning to indicate an unusual fluctuation of one or more of the plurality of real-time biological information;

automatically display a real-time reminder comprising a medication reminder message, one or more of the plurality of real-time biological information and a notification on abnormality of one or more of the plurality of real-time biological information; and display an automated recommendation comprising a recognized health condition along with a user location, one or more of the plurality of real-time biological information, a health management technique and a diet management technique with an additional scientific and nutritional information on recommended diet.

20. The telemetry apparatus in claim 1, wherein the telemetry apparatus, in an embodiment form, further comprises:

a LED device comprising a LED configured to emit multi-colored light in a line of multiple optical tubes to represent a plurality of device modes, device status and decorative applications.

21. The telemetry apparatus of claim 1, wherein the telemetry apparatus further comprises:

a main ring body configured to package sensors, circuits and electronics;

a temperature biosensor, on a contact surface of the main ring body, configured to extract a real-time bio-temperature signal and a thermal feedback;

a LED configured to display a plurality of device modes and decorative applications;

a wireless coil configured to wirelessly supply power and charge a battery of the telemetry apparatus;

a foam base, on the contact surface of the main ring body, configured to enhance a mechanical gripping and reduce a movement error;

a mechanical gripping element, comprising one or more of a hinge and a clip, configured to provide a size adjustable grip to securely fasten the telemetry apparatus on the sensing spot; and a waterproof coating.

22. The telemetry apparatus of claim 1, wherein the telemetry apparatus further comprises:

a main ring frame configured to package sensors, circuits and electronics;

a temperature biosensor, on a contact surface of the main ring frame, configured to extract a real-time bio-temperature signal and a thermal feedback;

a foam base, on the contact surface of the main ring frame, configured to enhance a mechanical gripping and reduce a movement error;

a dual clipper, comprising a bottom holding clip and an upper holding clip, configured to securely fasten the telemetry apparatus on the sensing spot;

a first extender hinge on the bottom holding clip and a second extender hinge on the upper holding clip, of the dual clipper, configured to provide an adjustable grip size; and a waterproof coating.

23. The telemetry apparatus of claim 1, wherein the telemetry apparatus further comprises:

an ear placement area configured to hold a plurality of sensors in a transmittive sensing configuration, wherein the plurality of sensors comprises the near-infrared optical spectrometer, the infrared optical dispersion analyzer spectrometer, the red optical dispersion analyzer spectrometer, the green optical spectrometer and a temperature biosensor;

a foam base, on a contact surface around the plurality of sensors, configured to reduce a movement error and enhance a mechanical gripping;

an ear hook clip configured to securely fasten the telemetry apparatus on the sensing spot;

a music ear bud configured to securely hold the telemetry apparatus on the sensing spot;

a LED, embedded near the ear hook clip, configured to display a plurality of device modes and decorative applications; and a waterproof coating.

24. The telemetry apparatus of claim 1, wherein the telemetry apparatus further comprises:

a touch screen configured to provide an access to a plurality of calibrations, a plurality of real-time medical information, a plurality of medical alerts and a plurality of automated recommendations;

a finger placement area configured to hold a plurality of sensors in a transmittive sensing configuration, wherein the plurality of sensors comprises the near-infrared optical spectrometer, the infrared optical dispersion analyzer spectrometer, the red optical dispersion analyzer spectrometer, the green optical spectrometer and a temperature biosensor;

a foam base, embedded on the finger placement area around the plurality of sensors, configured to enhance a mechanical gripping and reduce a movement error;

a detachable auxiliary powering module, comprising a first solar module and a second solar module, configured to harvest a solar energy;

an actuator configured to extend the second solar module from the first solar module to harvest more of the solar energy; and a waterproof coating.

* * * * *